(12) United States Patent
Dal Piaz et al.

(10) Patent No.: US 7,511,038 B2
(45) Date of Patent: Mar. 31, 2009

(54) PYRIDAZIN-3(2H)-ONE DERIVATIVES AND THEIR USE AS PDE4 INHIBITORS

(75) Inventors: Vittorio Dal Piaz, Impruneta (IT); Nuria Aguilar Izquierdo, Barcelona (ES); Maria Antonia Buil Albero, Barcelona (ES); Yolanda Garrido Rubio, Saragossa (ES); Maria Paola Giovannoni, Scandicci (IT); Jordi Gracia Ferrer, Barcelona (ES); Wenceslao Lumeras Amador, Sánt Just Desvern (ES); Claudia Vergelli, Grassina (IT)

(73) Assignee: Laboratorios Almirall S.A., Barcelona (ES)

( * ) Notice: Subject to any disclaimer, the term of this patent is extended or adjusted under 35 U.S.C. 154(b) by 30 days.

(21) Appl. No.: 10/578,594

(22) PCT Filed: Nov. 8, 2004

(86) PCT No.: PCT/EP2004/012604

§ 371 (c)(1),
(2), (4) Date: Feb. 15, 2007

(87) PCT Pub. No.: WO2005/049581

PCT Pub. Date: Jun. 2, 2005

(65) Prior Publication Data

US 2007/0197536 A1 Aug. 23, 2007

(30) Foreign Application Priority Data

Nov. 10, 2003 (ES) ................. 200302613

(51) Int. Cl.
C07D 237/04 (2006.01)
C07D 401/04 (2006.01)
C07D 401/06 (2006.01)
C07D 403/04 (2006.01)
C07D 403/06 (2006.01)
A61K 31/501 (2006.01)

(52) U.S. Cl. ............... 514/247; 544/238; 544/239; 514/252.01; 514/252.02; 514/252.03; 514/252.04; 514/252.06

(58) Field of Classification Search .......... 514/247, 514/252.01, 252.02, 252.03, 252.04, 252.05, 514/252.06; 544/238, 224, 239
See application file for complete search history.

(56) References Cited

FOREIGN PATENT DOCUMENTS

SU 405344 5/1984
WO WO 01/94391 A1 12/2001
WO WO 2004/058729 A1 7/2004

OTHER PUBLICATIONS

European Respiratory Society, Feb. 13, 2007, http://www.newtocopd.com/currentaffairsnews/list751_item17680.aspx, downloaded Jan. 16, 2008.*
Implications for Rheumatoid Arthritis http://www.medscape.com/viewarticle/464104, downloaded Jan. 17, 2008.*
Targan, et al., Inflammatory Bowel Disease: From Bench to Bedside, 2nd Edition, pp. 553-571, 2003.*
Prehn, et al., J. Clin. Immunol., vol. 21, No. 5, 2001, pp. 357-364.*
Barlocco, Daniela et al., Phenylpiperazinylalkylamino Substituted Pyridazinones as Potent $\alpha_1$ Adrenoceptor Antagonists, J. Med. Chem., 44:2403-2410 (2001).
Del Piaz, Virrorio et al., "5-Acyl-6-aryl-4-nitro-3(2H)pyridazinones and Related 4-Amino Compounds: Synthesis and Pharmacological Evaluation," Journal of Pharmaceutical Sciences, 34(60):341-348 (1991).
English Abstract for SU 405344.
Ciciani, Giovanna et al., "Synthesis and Evaluation of In Vitro Antitumor Activity of Some Substituted 5-Pyridazinyl-Styryletones", IL FARMACO, vol. 46 (7,8), pp. 873-885, 1991.
Bulka E., et al., Zeitschrift Für Chemie, 5(10):374-375 (1965).
Van der Mey, Margaretha et al., "Novel selective PDE4 Inhibitors. 1. Synthesis, structure-activity relationships, and molecular modeling of 4-(3,4-dimethoxyphenyl)-2H-phthalazin-1-ones and analogues," Journal of Medicinal Chemistry, 44(16):2511-2522 (2001).
International Search Report for PCT/EP2004/012604, dated Nov. 2, 2005.

* cited by examiner

*Primary Examiner*—Mark L Berch
*Assistant Examiner*—Cecilia M Jaisle
(74) *Attorney, Agent, or Firm*—Finnegan, Henderson, Farabow, Garrett & Dunner, LLP

(57) ABSTRACT

New pyridazin-e-(2H)-one derivatives having the chemical structure of general formula (I) are disclosed; as well as processes for their preparation, pharmaceutical compositions comprising them and their use in therapy as inhibitors of phosphodiesterase 4.

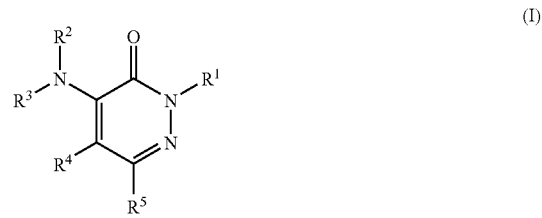

(I)

28 Claims, No Drawings

PYRIDAZIN-3(2H)-ONE DERIVATIVES AND THEIR USE AS PDE4 INHIBITORS

This application is a national stage filing under 35 U.S.C. § 371 of International Application No. PCT/EP2004/012604 filed on Nov. 8, 2004. This application claims priority of Spanish Patent Application No. P200302613, filed on Nov. 10, 2003.

The present invention relates to new therapeutically useful pyridazin-3(2H)-one derivatives, to processes for their preparation and to pharmaceutical compositions containing them. These compounds are potent and selective inhibitors of phosphodiesterase 4 (PDE4) and are thus useful in the treatment, prevention or suppression of pathological conditions, diseases and disorders known to be susceptible of being improved by inhibition of PDE4.

Phosphodiesterases (PDEs) comprise a superfamily of enzymes responsible for the hydrolysis and inactivation of the second messengers cyclic adenosine monophosphate (cAMP) and cyclic guanosine monophosphate (cGMP). Eleven different PDE families have been identified to date (PDE1 to PDE11) which differ in substrate preference, catalytic activity, sensitivity to endogenous activators and inhibitors, and encoding genes.

The PDE4 isoenzyme family exhibits a high affinity for cyclic AMP but has weak affinity for cyclic GMP. Increased cyclic AMP levels caused by PDE4 inhibition are associated with the suppression of cell activation in a wide range of inflammatory and immune cells, including lymphocytes, macrophages, basophils, neutrophils, and eosinophils. Moreover, PDE4 inhibition decreases the release of the cytokine Tumor Necrosis Factor α (TNFα). The biology of PDE4 is described in several recent reviews, for example M. D. Houslay, *Prog. Nucleic Acid Res. Mol. Biol.* 2001, 69, 249-315; J. E. Souness et al. *Immunopharmacol.* 2000 47, 127-162; or M. Conti and S. L. Jin, *Prog. Nucleic Acid Res. Mol. Biol.* 1999, 63, 1-38.

In view of these physiological effects, PDE4 inhibitors of varied chemical structures have been recently disclosed for the treatment or prevention of chronic and acute inflammatory diseases and of other pathological conditions, diseases and disorders known to be susceptible to amelioration by inhibition of PDE4. See, for example, U.S. Pat. No. 5,449,686, U.S. Pat. No. 5,710,170, WO 98/45268, WO 99/06404, WO 01/57025, WO 01/57036, WO 01/46184, WO 97/05105, WO 96/40636, U.S. Pat. No. 5,786,354, U.S. Pat. No. 5,773,467, U.S. Pat. No. 5,753,666, U.S. Pat. No. 5,728,712, U.S. Pat. No. 5,693,659, U.S. Pat. No. 5,679,696, U.S. Pat. No. 5,596,013, U.S. Pat. No. 5,541,219, U.S. Pat. No. 5,508,300, U.S. Pat. No. 5,502,072 or H. J. Dyke and J. G. Montana, *Exp. Opin. Invest Drugs* 1999, 8, 1301-1325.

A few compounds having the capacity to selectively inhibit phosphodiesterase 4 are in active development. Examples of these compounds are cipamfylline, arofyline, cilomilast, roflumilast, mesopram and pumafentrine.

We have now found that a novel series of pyridazin-3(2H)-one derivatives are potent and selective inhibitors of PDE4 and are therefore useful in the treatment or prevention of these pathological conditions, diseases and disorders, in particular asthma, chronic obstructive pulmonary disease, rheumatoid arthritis, atopic dermatitis, psoriasis or irritable bowel disease.

The compounds of the present invention can also be used in combination with other drugs known to be effective in the treatment of these diseases. For example, they can be used in combination with steroids or immunosuppressive agents, such as cyclosporin A, rapamycin or T-cell receptor blockers.

In this case the administration of the compounds allows a reduction of the dosage of the other drugs, thus preventing the appearance of the undesired side effects associated with both steroids and immunosuppressants.

Like other PDE4 inhibitors (see references above) the compounds of the invention can also be used for blocking the ulcerogenic effects induced by a variety of etiological agents, such as antiinflammatory drugs (steroidal or non-steroidal antiinflammatory agents), stress, ammonia, ethanol and concentrated acids. They can be used alone or in combination with antacids and/or antisecretory drugs in the preventive and/or curative treatment of gastrointestinal pathologies like drug-induced ulcers, peptic ulcers, *H. Pylori*-related ulcers, esophagitis and gastro-esophageal reflux disease.

They can also be used in the treatment of pathological situations where damage to the cells or tissues is produced through conditions like anoxia or the production of an excess of free radicals. Examples of such beneficial effects are the protection of cardiac tissue after coronary artery occlusion or the prolongation of cell and tissue viability when the compounds of the invention are added to preserving solutions intended for storage of transplant organs or fluids such as blood or sperm. They are also of benefit on tissue repair and wound healing.

Accordingly, the present invention provides novel compounds of formula (I):

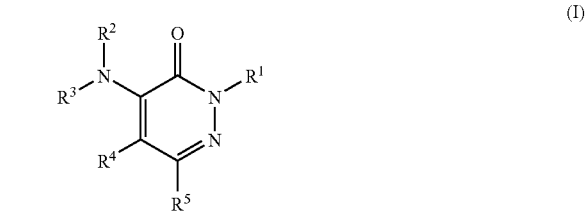

wherein

R¹ represents:
  a hydrogen atom;
  a group selected from acyl, alkoxycarbonyl, carbamoyl, monoalkylcarbamoyl or dialkylcarbamoyl;
  an alkyl, alkenyl or alkynyl group, which is optionally substituted by one or more substitutents selected from halogen atoms and hydroxy, alkoxy, aryloxy, alkylthio, arylthio, oxo, amino, mono- or di-alkylamino, acylamino, hydroxycarbonyl, alkoxycarbonyl, carbamoyl or mono- or di-alkylcarbamoyl groups;
  an aryl or heteroaryl group which is optionally substituted by one or more substitutents selected from halogen atoms and hydroxy, hydroxyalkyl, hydroxycarbonyl, alkoxy, alkylenedioxy, alkoxycarbonyl, aryloxy, acyl, acyloxy, alkylthio, arylthio, amino, nitro, cyano, mono- or di-alkylamino, acylamino, carbamoyl or mono- or di-alkylcarbamoyl, difluoromethyl, trifluoromethyl, difluoromethoxy or trifluoromethoxy groups;
  a saturated or unsaturated heterocyclic group which is optionally substituted by one or more substitutents selected from halogen atoms and hydroxy, hydroxyalkyl, hydroxycarbonyl, alkoxy, alkylenedioxy, alkoxycarbonyl, aryloxy, acyl, acyloxy, alkylthio, arylthio, oxo, amino, nitro, cyano, mono- or di-alkylamino, acylamino, carbamoyl or mono- or di-alkylcarbamoyl, difluoromethyl, trifluoromethyl, difluoromethoxy or trifluoromethoxy groups;

a group of formula

—(CH$_2$)$_n$—R$^6$ wherein n is an integer from 0 to 4 and R$^6$ represents:
  a cycloalkyl or cycloalkenyl group;
  an aryl group, which is optionally substituted by one or more substitutents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
  or a 3- to 7-membered ring comprising from 1 to 4 heteroatoms selected from nitrogen, oxygen and sulphur, which ring is optionally substituted by one or more substitutents selected from halogen atoms and alkyl, hydroxy, alkoxy, alkylenedioxy, amino, mono- or di-alkylamino, nitro, cyano or trifluoromethyl groups;

R$^2$ represents:
  a hydrogen atom;
  a group selected from acyl, alkoxycarbonyl, carbamoyl, monoalkylcarbamoyl or dialkylcarbamoyl;
  an alkyl, alkenyl or alkynyl group, which is optionally substituted by one or more substitutents selected from halogen atoms and hydroxy, alkoxy, hydroxycarbonyl, alkoxycarbonyl, aryloxy, alkylthio, arylthio, oxo, amino, mono- or di-alkylamino, acylamino, carbamoyl or mono- or di-alkylcarbamoyl groups;
  an aryl or heteroaryl group which is optionally substituted by one or more substitutents selected from halogen atoms and hydroxy, hydroxyalkyl, hydroxycarbonyl, alkoxy, alkylenedioxy, alkoxycarbonyl, aryloxy, acyl, acyloxy, alkylthio, arylthio, amino, nitro, cyano, mono- or di-alkylamino, acylamino, carbamoyl or mono- or di-alkylcarbamoyl, difluoromethyl, trifluoromethyl, difluoromethoxy or trifluoromethoxy groups;
  a saturated or unsaturated heterocyclic group which is optionally substituted by one or more substitutents selected from halogen atoms and hydroxy, hydroxyalkyl, hydroxycarbonyl, alkoxy, alkylenedioxy, alkoxycarbonyl, aryloxy, acyl, acyloxy, alkylthio, arylthio, oxo, amino, nitro, cyano, mono- or di-alkylamino, acylamino, carbamoyl or mono- or di-alkylcarbamoyl, difluoromethyl, trifluoromethyl, difluoromethoxy or trifluoromethoxy groups;
  a group of formula —(CH$_2$)$_n$—R$^6$ wherein n is an integer from 0 to 4 and R$^6$ represents:
  a cycloalkyl or cycloalkenyl group;
  an aryl group, which is optionally substituted by one or more substitutents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
  or a 3- to 7-membered ring comprising from 1 to 4 heteroatoms selected from nitrogen, oxygen and sulphur, which ring is optionally substituted by one or more substitutents selected from halogen atoms and alkyl, hydroxy, alkoxy, alkylenedioxy, amino, mono- or di-alkylamino, nitro, cyano or trifluoromethyl groups;

R$^3$ represents a monocyclic or polycyclic aryl or heteroaryl group, which is optionally substituted by one or more substitutents selected from:
  halogen atoms;
  alkyl and alkylene groups, which are optionally substituted by one or more substitutents selected from halogen atoms and phenyl, hydroxy, alkoxy, aryloxy, alkylthio, arylthio, oxo, amino, mono- or di-alkylamino, acylamino, hydroxycarbonyl, alkoxycarbonyl, carbamoyl or mono- or di-alkylcarbamoyl groups
  phenyl, hydroxy, hydroxycarbonyl, hydroxyalkyl, alkoxycarbonyl, alkoxy, cycloalkoxy, nitro, cyano, aryloxy, alkylthio, arylthio, alkylsulfinyl, alkylsulfonyl, alkylsulfamoyl, acyl, amino, mono- or di-alkylamino, acylamino, hydroxycarbonyl, alkoxycarbonyl, carbamoyl, mono- or di-alkylcarbamoyl, ureido, N'-alkylureido, N',N'-dialkylureido, alkylsulfamido, aminosuphonyl, mono- or di-alkylaminosulfonyl, cyano, difluoromethoxy or trifluoromethoxy groups;

R$^4$ represents:
  a hydrogen atom;
  a hydroxy, alkoxy, amino, monoalkylamino, dialkylamino or cyano group;
  an alkyl, alkenyl or alkynyl group which is optionally substituted by one or more substitutents selected from halogen atoms and hydroxy, acyloxy, alkoxy, aryloxy, alkylthio, arylthio, amino, mono- or di-alkylamino, acylamino, hydroxycarbonyl, alkoxycarbonyl, alkoxyimino, carbamoyl and mono- or di-alkylcarbamoyl groups;
  or a group of formula —(CH$_2$)$_n$—R$^6$ wherein n is an integer from 0 to 4 and R$^6$ represents:
  a cycloalkyl or cycloalkenyl group;
  an aryl group, which is optionally substituted by one or more substitutents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
  or a 3- to 7-membered ring comprising from 1 to 4 heteroatoms selected from nitrogen, oxygen and sulphur, which ring is optionally substituted by one or more substitutents selected from halogen atoms and alkyl, phenyl, alkoxyphenyl, halophenyl, pyridyl, alkoxycarbonyl, hydroxy, alkoxy, alkylenedioxy, amino, mono- or di-alkylamino, nitro, cyano or trifluoromethyl groups;

R$^5$ represents a group —COOR$^7$ or a monocyclic or polycyclic aryl or heteroaryl group, which is optionally substituted by one or more substitutents selected from:
  halogen atoms;
  alkyl and alkenyl groups, which are optionally substituted by one or more substitutents selected from halogen atoms and phenyl, hydroxy, hydroxyalkyl, alkoxy, aryloxy, alkylthio, arylthio, oxo, amino, mono- or di-alkylamino, acylamino, hydroxycarbonyl, alkoxycarbonyl, carbamoyl, mono- or di-alkylcarbamoyl groups; and
  phenyl, hydroxy, alkylenedioxy, alkoxy, cycloalkyloxy, alkylthio, alkylsulfinyl, alkylsulfonyl, alkylsulfamoyl, amino, mono- or di-alkylamino, acylamino, nitro, acyl, hydroxycarbonyl, alkoxycarbonyl, carbamoyl, mono- or di-alkylcarbamoyl, ureido, N'-alkylureido, N',N'-dialkylureido, alkylsulfamido, aminosuphonyl, mono- or di-alkylaminosulfonyl, cyano, difluoromethoxy or trifluoromethoxy groups;

wherein $R^7$ represents an alkyl group which is optionally substituted by one or more substituents selected from halogen atoms and hydroxy, alkoxy, aryloxy, alkylthio, arylthio, oxo, amino, mono- or di-alkylamino, acylamino, hydroxycarbonyl, alkoxycarbonyl, carbamoyl, mono- or di-alkylcarbamoyl groups or a group of formula

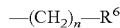

wherein n is an integer from 0 to 4 and $R^6$ represents:
a cycloalkyl or cycloalkenyl group;
an aryl group, which is optionally substituted by one or more substitutents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
or a 3- to 7-membered ring comprising from 1 to 4 heteroatoms selected from nitrogen, oxygen and sulphur, which ring is optionally substituted by one or more substitutents selected from halogen atoms and alkyl, phenyl, alkoxyphenyl, halophenyl, pyridyl, alkoxycarbonyl, hydroxy, alkoxy, alkylenedioxy, amino, mono- or di-alkylamino, nitro, cyano or trifluoromethyl groups;

with the proviso that when $R^1$ is methyl, $R^2$ is H, and both $R^3$ and $R^5$ are phenyl then $R^4$ is not a 1-hydroxyethyl group.

and the pharmaceutically acceptable salts or N-oxides thereof.

Certain pyridazin-3(2H)-one derivatives of similar structure, which do not fall within the scope of the present invention, have been disclosed in *J. Pharm. Sci.* 1991, 80, 341-348 and *J. Med. Chem.* 1999, 42, 1894-1900.

Further objectives of the present invention are to provide processes for preparing said compounds; pharmaceutical compositions comprising an effective amount of said compounds; the use of the compounds in the manufacture of a medicament for the treatment of diseases susceptible of being improved by inhibition of PDE4; and methods of treatment of diseases susceptible to amelioration by inhibition of PDE4, which methods comprise the administration of the compounds of the invention to a subject in need of treatment.

As used herein the term alkyl embraces optionally substituted, linear or branched radicals having 1 to 20 carbon atoms or, preferably 1 to 12 carbon atoms. More preferably alkyl radicals are "lower alkyl" radicals having 1 to 8, preferably 1 to 6 and more preferably 1 to 4 carbon atoms.

Examples include methyl, ethyl, n-propyl, i-propyl, n-butyl, sec-butyl, t-butyl, n-pentyl, 1-methylbutyl, 2-methylbutyl, isopentyl, 1-ethylpropyl, 1,1-dimethylpropyl, 1,2-dimethylpropyl, n-hexyl, 1-ethylbutyl, 2-ethylbutyl, 1,1-dimethylbutyl, 1,2-dimethylbutyl, 1,3-dimethylbutyl, 2,2-dimethylbutyl, 2,3-dimethylbutyl, 2-methylpentyl, 3-methylpentyl and iso-hexyl radicals.

As used herein, the term alkenyl embraces optionally substituted, linear or branched, mono or polyunsaturated radicals having 1 to 20 carbon atoms or, preferably, 1 to 12 carbon atoms. More preferably alkenyl radicals are "lower alkenyl" radicals having 2 to 8, preferably 2 to 6 and more preferably 2 to 4 carbon atoms. In particular it is preferred that the alkenyl radicals are mono or diunsaturated.

Examples include vinyl, allyl, 1-propenyl, isopropenyl, 1-butenyl, 2-butenyl, 3-butenyl, 1-pentenyl, 2-pentenyl, 3-pentenyl and 4-pentenyl radicals.

As used herein, the term alkynyl embraces optionally substituted, linear or branched, mono or polyunsaturated radicals having 1 to 20 carbon atoms or, preferably, 1 to 12 carbon atoms. More preferably, alkynyl radicals are "lower alkynyl" radicals having 2 to 8, preferably 2 to 6 and more preferably 2 to 4 carbon atoms. In particular, it is preferred that the alkynyl radicals are mono or diunsaturated.

Examples include 1-propynyl, 2-propynyl, 1-butynyl, 2-butynyl and 3-butynyl radicals.

When it is mentioned that alkyl, alkenyl or alkynyl radicals may be optionally substituted it is meant to include linear or branched alkyl, alkenyl or alkynyl radicals as defined above, which may be unsubstituted or substituted in any position by one or more substitutents, for example by 1, 2 or 3 substitutents. When two or more substitutents are present, each substitutent may be the same or different.

A said optionally substituted alkenyl group is typically unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, substitutents on an alkenyl group are themselves unsubstituted.

A said optionally substituted alkynyl group is typically unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, substitutents on an alkynyl group are themselves unsubstituted.

A said optionally substituted alkyl group is typically unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, substitutents on an alkyl group are themselves unsubstituted. Preferred optionally substituted alkyl groups are unsubstituted or substituted with 1, 2 or 3 fluorine atoms.

As used herein, the term alkylene embraces divalent alkyl moieties typically having from 1 to 6, for example from 1 to 4, carbon atoms. Examples of $C_1$-$C_4$ alkylene radicals include methylene, ethylene, propylene, butylene, pentylene and hexylene radicals.

A said optionally substituted alkylene group is typically unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms.

When an alkylene radical is present as a substituent on another radical it shall be deemed to be a single substitutent, rather than a radical formed by two substitutents.

As used herein, the term alkoxy (or alkyloxy) embraces optionally substituted, linear or branched oxy-containing radicals each having alkyl portions of 1 to 10 carbon atoms. More preferred alkoxy radicals are "lower alkoxy" radicals having 1 to 8, preferably 1 to 6 and more preferably 1 to 4 carbon atoms.

An alkoxy group is typically unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, the substitutents on an alkoxy group are themselves unsubstituted.

Preferred alkoxy radicals include methoxy, ethoxy, n-propoxy, i-propoxy, n-butoxy, sec-butoxy, t-butoxy, trifluoromethoxy, difluoromethoxy, hydroxymethoxy, 2-hydroxyethoxy and 2-hydroxypropoxy.

As used herein, the term alkylthio embraces radicals containing an optionally substituted, linear or branched alkyl radicals of 1 to 10 carbon atoms attached to a divalent sulfur atom. More preferred alkylthio radicals are "lower alkylthio" radicals having 1 to 8, preferably 1 to 6 and more preferably 1 to 4 carbon atoms.

An alkylthio group is typically unsubstituted or substituted with 1, 2 or 3 substituents which may be the same or different. The substitutents are preferably selected from halogen atoms, preferably fluorine atoms, hydroxy groups and alkoxy groups having from 1 to 4 carbon atoms. Typically, the substitutents on an alkythio group are themselves unsubstituted.

Preferred optionally substituted alkylthio radicals include methylthio, ethylthio, n-propylthio, i-propylthio, n-butylthio, sec-butylthio, t-butylthio, trifluoromethylthio, difluoromethylthio, hydroxymethylthio, 2-hydroxyethylthio and 2-hydroxypropylthio.

As used herein, the term monoalkylamino embraces radicals containing an optionally substituted, linear or branched alkyl radicals of 1 to 10 carbon atoms attached to a divalent —NH— radical. More preferred monoalkylamino radicals are "lower monoalkylamino" radicals having 1 to 8, preferably 1 to 6 and more preferably 1 to 4 carbon atoms.

A monoalkylamino group typically contains an alkyl group which is unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, the substitutents on a monoalkylamino group are themselves unsubstituted.

Preferred optionally substituted monoalkylamino radicals include methylamino, ethylamino, n-propylamino, i-propylamino, n-butylamino, sec-butylamino, t-butylamino, trifluoromethylamino, difluoromethylamino, hydroxymethylamino, 2-hydroxyethylamino and 2-hydroxypropylamino.

As used herein, the term dialkylamino embraces radicals containing a trivalent nitrogen atoms with two optionally substituted, linear or branched alkyl radicals of 1 to 10 carbon atoms attached thereto. More preferred dialkylamino radicals are "lower dialkylamino" radicals having 1 to 8, preferably 1 to 6 and more preferably 1 to 4 carbon atoms in each alkyl radical.

A dialkylamino group typically contains two alkyl groups, each of which is unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, the substitutents on a dialkylamino group are themselves unsubstituted.

Preferred optionally substituted dialkylamino radicals include dimethylamino, diethylamino, methyl(ethyl)amino, di(n-propyl)amino, n-propyl(methyl)amino, n-propyl(ethyl) amino, di(i-propyl)amino, i-propyl(methyl)amino, i-propyl (ethyl)amino, di(n-butyl)amino, n-butyl(methyl)amino, n-butyl(ethyl)amino, n-butyl(i-propyl)amino, di(sec-butyl) amino, sec-butyl(methyl)amino, sec-butyl(ethyl)amino, sec-butyl(n-propyl)amino, sec-butyl(i-propyl)amino, di(t-butyl) amino, t-butyl(methyl)amino, t-butyl(ethyl)amino, t-butyl(n-propyl)amino, t-butyl(i-propyl)amino, trifluoromethyl (methyl)amino, trifluoromethyl(ethyl)amino, trifluoromethyl(n-propyl)amino, trifluoromethyl(i-propyl) amino, trifluoromethyl(n-butyl)amino, trifluoromethyl(sec-butyl)amino, difluoromethyl(methyl)amino, difluoromethyl (ethyl)amino, difluoromethyl(n-propyl)amino, difluoromethyl(i-propyl)amino, difluoromethyl(n-butyl)) amino, difluoromethyl(sec-butyl)amino, difluoromethyl(t-butyl)amino, difluoromethyl(trifluoromethyl)amino, hydroxymethyl(methyl)amino, ethyl(hydroxymethyl)amino, hydroxymethyl(n-propyl)amino, hydroxymethyl(i-propyl) amino, n-butyl(hydroxymethyl)amino, sec-butyl(hydroxymethyl)amino, t-butyl(hydroxymethyl)amino, difluoromethyl (hydroxymethyl)amino, hydroxymethyl(trifluoromethyl) amino, hydroxyethyl(methyl)amino, ethyl(hydroxyethyl) amino, hydroxyethyl(n-propyl)amino, hydroxyethyl(i-propyl)amino, n-butyl(hydroxyethyl)amino, sec-butyl (hydroxyethyl)amino, t-butyl(hydroxyethyl)amino, difluoromethyl(hydroxyethyl)amino, hydroxyethyl(trifluoromethyl)amino, hydroxypropyl(methyl)amino, ethyl(hydroxypropyl)amino, hydroxypropyl(n-propyl)amino, hydroxypropyl(i-propyl)amino, n-butyl(hydroxypropyl) amino, sec-butyl(hydroxypropyl)amino, t-butyl(hydroxypropyl)amino, difluoromethyl(hydroxypropyl)amino, hydroxypropyl(trifluoromethyl)amino.

As used herein, the term hydroxyalkyl embraces linear or branched alkyl radicals having 1 to 10 carbon atoms, preferably 1 to 6 carbon atoms, any one of which may be substituted with one or more hydroxyl radicals.

Examples of such radicals include hydroxymethyl, hydroxyethyl, hydroxypropyl, hydroxybutyl and hydroxyhexyl.

As used herein, the term alkoxycarbonyl embraces optionally substituted, linear or branched radicals each having alkyl portions of 1 to 10 carbon atoms and attached to an oxycarbonyl radical. More preferred alkoxycarbonyl radicals are "lower alkoxycarbonyl" radicals, in which the alkyl moiety has 1 to 8, preferably 1 to 6 and more preferably 1 to 4 carbon atoms.

An alkoxycarbonyl group is typically unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, the substitutents on an alkoxycarbonyl group are themselves unsubstituted.

Preferred optionally substituted alkoxycarbonyl radicals include methoxycarbonyl, ethoxycarbonyl, n-propoxycarbonyl, i-propoxycarbonyl, n-butoxycarbonyl, sec-butoxycarbonyl, t-butoxycarbonyl, trifluoromethoxycarbonyl, difluoromethoxycarbonyl, hydroxymethoxycarbonyl, 2-hydroxyethoxycarbonyl and 2-hydroxypropoxycarbonyl.

As used herein, the term monoalkylcarbamoyl embraces radicals containing an optionally substituted, linear or branched alkyl radicals of 1 to 10 carbon atoms and attached to the nitrogen of a —NHCO— radical. More preferred monoalkylcarbamoyl radicals are "lower monoalkylcarbamoyl" radicals in which the alkyl moiety has 1 to 8, preferably 1 to 6 and more preferably 1 to 4 carbon atoms.

A monoalkylcarbamoyl group is typically unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, the substitutents on a monoalkylcarbamoyl group are themselves unsubstituted.

Preferred optionally substituted monoalkylcarbamoyl radicals include methylcarbamoyl, ethylcarbamoyl, n-propylcarbamoyl, i-propylcarbamoyl, n-butylcarbamoyl, sec-butylcarbamoyl, t-butylcarbamoyl, trifluoromethylcarbamoyl, difluoromethylcarbamoyl, hydroxymethylcarbamoyl, 2-hydroxyethylcarbamoyl and 2-hydroxypropylcarbamoyl.

As used herein, the term dialkylcarbamoyl embraces radicals containing a radical NCO— where the nitrogen is attached to two optionally substituted, linear or branched alkyl radicals of 1 to 10 carbon atoms. More preferred dialkylcarbamoyl radicals are "lower dialkylcarbamoyl" radicals having 1 to 8, preferably 1 to 6 and more preferably 1 to 4 carbon atoms in each alkyl radical.

A dialkylcarbamoyl group is typically unsubstituted or substituted with 1, 2 or 3 substituents which may be the same or different. The substitutents are preferably selected from halogen atoms, preferably fluorine atoms, hydroxy groups and alkoxy groups having from 1 to 4 carbon atoms. Typically, the substitutents on a dialkylcarbamoyl group are themselves unsubstituted.

Preferred optionally substituted dialkylcarbamoyl radicals include dimethylcarbamoyl, diethylcarbamoyl, methyl(ethyl)carbamoyl, di(n-propyl)carbamoyl, n-propyl(methyl)carbamoyl, n-propyl(ethyl)carbamoyl, di(i-propyl)carbamoyl, i-propyl(methyl)carbamoyl, i-propyl(ethyl)carbamoyl, di(n-butyl)carbamoyl, n-butyl(methyl)carbamoyl, n-butyl(ethyl)carbamoyl, n-butyl(i-propyl)carbamoyl, di(sec-butyl)carbamoyl, sec-butyl(methyl)carbamoyl, sec-butyl(ethyl)carbamoyl, sec-butyl(n-propyl)carbamoyl, sec-butyl(i-propyl)carbamoyl, di(t-butyl)carbamoyl, t-butyl(methyl)carbamoyl, t-butyl(ethyl)carbamoyl, t-butyl(n-propyl)carbamoyl, t-butyl(i-propyl)carbamoyl, trifluoromethyl(methyl)carbamoyl, trifluoromethyl(ethyl)carbamoyl, trifluoromethyl(n-propyl)carbamoyl, trifluoromethyl(i-propyl)carbamoyl, trifluoromethyl(n-butyl)carbamoyl, trifluoromethyl(sec-butyl)carbamoyl, difluoromethyl(methyl)carbamoyl, difluoromethyl(ethyl)carbamoyl, difluoromethyl(n-propyl)carbamoyl, difluoromethyl(i-propyl)carbamoyl, difluoromethyl(n-butyl)carbamoyl, difluoromethyl(sec-butyl)carbamoyl, difluoromethyl(t-butyl)carbamoyl, difluoromethyl(trifluoromethyl)carbamoyl, hydroxymethyl(methyl)carbamoyl, ethyl(hydroxymethyl)carbamoyl, hydroxymethyl(n-propyl)carbamoyl, hydroxymethyl(i-propyl)carbamoyl, n-butyl(hydroxymethyl)carbamoyl, sec-butyl(hydroxymethyl)carbamoyl, t-butyl(hydroxymethyl)carbamoyl, difluoromethyl(hydroxymethyl)carbamoyl, hydroxymethyl(trifluoromethyl)carbamoyl, hydroxyethyl(methyl)carbamoyl, ethyl(hydroxyethyl)carbamoyl, hydroxyethyl(n-propyl)carbamoyl, hydroxyethyl(i-propyl)carbamoyl, n-butyl(hydroxyethyl)carbamoyl, sec-butyl(hydroxyethyl)carbamoyl, t-butyl(hydroxyethyl)carbamoyl, difluoromethyl(hydroxyethyl)carbamoyl, hydroxyethyl(trifluoromethyl)carbamoyl, hydroxypropyl(methyl)carbamoyl, ethyl(hydroxypropyl)carbamoyl, hydroxypropyl(n-propyl)carbamoyl, hydroxypropyl(i-propyl)carbamoyl, n-butyl(hydroxypropyl)carbamoyl, sec-butyl(hydroxypropyl)carbamoyl, t-butyl(hydroxypropyl)carbamoyl, difluoromethyl(hydroxypropyl)carbamoyl, hydroxypropyl(trifluoromethyl)carbamoyl.

As used herein, the term alkylsulfinyl embraces radicals containing an optionally substituted, linear or branched alkyl radicals of 1 to 10 carbon atoms attached to a divalent —SO— radical. More preferred alkylsulfinyl radicals are "lower alkylsulfinyl" radicals having 1 to 8, preferably 1 to 6 and more preferably 1 to 4 carbon atoms.

An alkylsulfinyl group is typically unsubstituted or substituted with 1, 2 or 3 substituents which may be the same or different. The substitutents are preferably selected from halogen atoms, preferably fluorine atoms, hydroxy groups and alkoxy groups having from 1 to 4 carbon atoms. Typically, the substitutents on a alkylsulfinyl group are themselves unsubstituted.

Preferred optionally substituted alkylsulfinyl radicals include methylsulfinyl, ethylsulfinyl, n-propylsulfinyl, i-propylsulfinyl, n-butylsulfinyl, sec-butylsulfinyl, t-butylsulfinyl, trifluoromethylsulfinyl, difluoromethylsulfinyl, hydroxymethylsulfinyl, 2-hydroxyethylsulfinyl and 2-hydroxypropylsulfinyl.

As used herein, the term alkylsulfonyl embraces radicals containing an optionally substituted, linear or branched alkyl radicals of 1 to 10 carbon atoms attached to a divalent —$SO_2$— radical. More preferred alkylsulfonyl radicals are "lower alkylsulfonyl" radicals having 1 to 8, preferably 1 to 6 and more preferably 1 to 4 carbon atoms.

An alkylsulfonyl group is typically unsubstituted or substituted with 1, 2 or 3 substituents which may be the same or different. The substitutents are preferably selected from halogen atoms, preferably fluorine atoms, hydroxy groups and alkoxy groups having from 1 to 4 carbon atoms. Typically, the substituents on a monoalkylaminosulfonyl group are themselves unsubstituted.

As used herein, the term monoalkylaminosulfonyl embraces radicals containing an optionally substituted, linear or branched alkyl radicals of 1 to 10 carbon atoms and attached to the nitrogen of a —$NHSO_2$— radical. More preferred monoalkylaminosulfonyl radicals are "lower monoalkylaminosulfonyl" radicals having 1 to 8, preferably 1 to 6 and more preferably 1 to 4 carbon atoms.

A monoalkylaminosulfonyl group is typically unsubstituted or substituted with 1, 2 or 3 substituents which may be the same or different. The substitutents are preferably selected from halogen atoms, preferably fluorine atoms, hydroxy groups and alkoxy groups having from 1 to 4 carbon atoms. Typically, the substitutents on a monoalkylaminosulfonyl group are themselves unsubstituted.

Preferred optionally substituted monoalkylaminosulfonyl radicals include methylaminosulfonyl, ethylaminosulfonyl, n-propylaminosulfonyl, i-propylaminosulfonyl, n-butylaminosulfonyl, sec-butylaminosulfonyl, t-butylaminosulfonyl, trifluoromethylaminosulfonyl, difluoromethylaminosulfonyl, hydroxymethylaminosulfonyl, 2-hydroxyethylaminosulfonyl and 2-hydroxypropylaminosulfonyl.

As used herein, the term dialkylaminosulfonyl embraces radicals containing a radical $NSO_2$— where the nitrogen is attached to two optionally substituted, linear or branched alkyl radicals of 1 to 10 carbon atoms. More preferred dialkylaminosulfonyl radicals are "lower dialkylaminosulfonyl" radicals having 1 to 8, preferably 1 to 6 and more preferably 1 to 4 carbon atoms in each alkyl radical.

A dialkylaminosulfonyl group is typically unsubstituted or substituted with 1, 2 or 3 substituents which may be the same or different. The substitutents are preferably selected from halogen atoms, preferably fluorine atoms, hydroxy groups and alkoxy groups having from 1 to 4 carbon atoms. Typically, the substitutents on a dialkylaminosulfonyl group are themselves unsubstituted.

Preferred optionally substituted dialkylaminosulfonyl radicals include dimethylaminosulfonyl, diethylaminosulfonyl, methyl(ethyl)aminosulfonyl, di(n-propyl)aminosulfonyl, n-propyl(methyl)aminosulfonyl, n-propyl(ethyl)aminosulfonyl, di(i-propyl)aminosulfonyl, i-propyl(methyl)aminosulfonyl, i-propyl(ethyl)aminosulfonyl, di(n-butyl)aminosulfonyl, n-butyl(methyl)aminosulfonyl, n-butyl(ethyl)aminosulfonyl, n-butyl(i-propyl)aminosulfonyl, di(sec-butyl)aminosulfonyl, sec-butyl(methyl)aminosulfonyl, sec-butyl(ethyl)aminosulfonyl, sec-butyl(n-propyl)aminosulfonyl, sec-butyl(i-propyl)aminosulfonyl, di(t-butyl) aminosulfonyl, t-butyl(methyl)aminosulfonyl, t-butyl(ethyl) aminosulfonyl, t-butyl(n-propyl)aminosulfonyl, t-butyl(i-propyl)aminosulfonyl, trifluoromethyl(methyl) aminosulfonyl, trifluoromethyl(ethyl)aminosulfonyl, trifluoromethyl(n-propyl)aminosulfonyl, trifluoromethyl(i-propyl)aminosulfonyl, trifluoromethyl(n-butyl)aminosulfonyl, trifluoromethyl(sec-butyl)aminosulfonyl, difluoromethyl(methyl)aminosulfonyl, difluoromethyl(ethyl) aminosulfonyl, difluoromethyl(n-propyl)aminosulfonyl, difluoromethyl(i-propyl)aminosulfonyl, difluoromethyl(n-butyl))aminosulfonyl, difluoromethyl(sec-butyl)aminosulfonyl, difluoromethyl(t-butyl)aminosulfonyl, difluoromethyl (trifluoromethyl)aminosulfonyl, hydroxymethyl(methyl) aminosulfonyl, ethyl(hydroxymethyl)aminosulfonyl, hydroxymethyl(n-propyl)aminosulfonyl, hydroxymethyl(i-propyl)aminosulfonyl, n-butyl(hydroxymethyl)aminosulfonyl, sec-butyl(hydroxymethyl)aminosulfonyl, t-butyl(hydroxymethyl)aminosulfonyl, difluoromethyl (hydroxymethyl)aminosulfonyl, hydroxymethyl (trifluoromethyl)aminosulfonyl, hydroxyethyl(methyl) aminosulfonyl, ethyl(hydroxyethyl)aminosulfonyl, hydroxyethyl(n-propyl)aminosulfonyl, hydroxyethyl(i-propyl)aminosulfonyl, n-butyl(hydroxyethyl)aminosulfonyl, sec-butyl(hydroxyethyl)aminosulfonyl, t-butyl(hydroxyethyl)aminosulfonyl, difluoromethyl(hydroxyethyl)aminosulfonyl, hydroxyethyl(trifluoromethyl)aminosulfonyl, hydroxypropyl(methyl)aminosulfonyl, ethyl(hydroxypropyl)aminosulfonyl, hydroxypropyl(n-propyl)aminosulfonyl, hydroxypropyl(i-propyl)aminosulfonyl, n-butyl(hydroxypropyl)aminosulfonyl, sec-butyl(hydroxypropyl)aminosulfonyl, t-butyl(hydroxypropyl)aminosulfonyl, difluoromethyl (hydroxypropyl)aminosulfonyl and hydroxypropyl (trifluoromethyl)aminosulfonyl.

As used herein, the term alkylsulfamoyl embraces radicals containing an optionally substituted, linear or branched alkyl radical of 1 to 10 carbon atoms and attached to the nitrogen of a —NSO$_2$— radical. More preferred alkylsulfamoyl radicals are "lower alkylsulfamoyl" radicals having 1 to 8, preferably 1 to 6 and more preferably 1 to 4 carbon atoms.

An alkylsulfamoyl group is typically unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, the substitutents on an alkylsulfamoyl group are themselves unsubstituted.

Preferred optionally substituted alkylsulfamoyl radicals include methylsulfamoyl, ethylsulfamoyl, n-propylsulfamoyl, i-propylsulfamoyl, n-butylsulfamoyl, sec-butylsulfamoyl, t-butylsulfamoyl, trifluoromethylsulfamoyl, difluoromethylsulfamoyl, hydroxymethylsulfamoyl, 2-hydroxyethylsulfamoyl and 2-hydroxypropylsulfamoyl.

As used herein, the term alkylsulfamido embraces radicals containing an optionally substituted, linear or branched alkyl radicals of 1 to 10 carbon atoms and attached to one of the nitrogen atoms of a —NHSO$_2$NH— radical. More preferred alkylsulfamido radicals are "lower alkylsulfamido" radicals having 1 to 8, preferably 1 to 6 and more preferably 1 to 4 carbon atoms.

An alkylsulfamido group is typically unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, the substitutents on an alkylsulfamido group are themselves unsubstituted.

Preferred optionally substituted alkylsulfamido radicals include methylsulfamido, ethylsulfamido, n-propylsulfamido, i-propylsulfamido, n-butylsulfamido, sec-butylsulfamido, t-butylsulfamido, trifluoromethylsulfamido, difluoromethylsulfamido, hydroxymethylsulfamido, 2-hydroxyethylsulfamido and 2-hydroxysulfamido.

As used herein, the term N'-alkylureido embraces radicals containing an optionally substituted, linear or branched alkyl radical of 1 to 10 carbon atoms attached to the terminal nitrogen of a —NHCONH— radical. More preferred N'-alkylureido radicals are "lower N'-alkylureido" radicals in which the alkyl moiety has 1 to 8, preferably 1 to 6 and more preferably 1 to 4 carbon atoms.

An N'-alkylureido group is typically unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, the substitutents on an N'-alkylureido group are themselves unsubstituted.

Preferred optionally substituted N'-alkylureido radicals include N'-methylureido, N'-ethylureido, N'-n-propylureido, N'-i-propylureido, N'-n-butylureido, N'-sec-butylureido, N'-t-butylureido, N'-trifluoromethylureido, N'-difluoromethylureido, N'-hydroxymethylureido, N'-2-hydroxyethylureido and N'-2-hydroxypropylureido.

As used herein, the term N',N'-dialkylureido embraces radicals containing a radical —NHCON where the terminal nitrogen is attached to two optionally substituted, linear or branched alkyl radicals of 1 to 10 carbon atoms. More preferred N',N'-dialkylureido radicals are "lower N',N'-dialkylureido" radicals having 1 to 8, preferably 1 to 6 and more preferably 1 to 4 carbon atoms in each alkyl radical.

A N',N'-dialkylureido group is typically unsubstituted or substituted with 1, 2 or 3 substitutents which may be the same or different. The substitutents are preferably selected from halogen atoms, preferably fluorine atoms, hydroxy groups and alkoxy groups having from 1 to 4 carbon atoms. Typically, the substitutents on an N',N'-dialkylureido group are themselves unsubstituted.

Preferred optionally substituted N',N'-dialkylureido radicals include N',N'-dimethylureido, N',N'-diethylureido, N'-methyl,N'-ethylureido, N',N'-di(n-propyl)ureido, N'-n-propyl,N'-methylureido, N'-n-propyl,N'-ethylureido, N',N'-di(i-propyl)ureido, N'-i-propyl, N'-methylureido, N'-i-propyl,N'-ethylureido, N',N'-di(n-butyl)ureido, N'-n-butyl, N'-methylureido, N'-n-butyl,N'-ethylureido, N'-n-butyl, N'-(i-propyl)ureido, N',N'-di(sec-butyl)ureido, N'-sec-butyl,N'-methylureido, N'-sec-butyl,N'-ethylureido, N'-sec-butyl,N'-(n-propyl)ureido, N'-sec-butyl,N'(i-propyl)ureido, N',N'di(t-butyl)ureido, N'-t-butyl,N'-methylureido, N'-t-butyl,N'-ethylureido, N'-t-butyl,N'-(n-propyl)ureido, N'-t-butyl, N'-(i-propyl)ureido, N'-trifluoromethyl,N'-methylureido, N'-trifluoromethyl,N'-ethylureido, N'-trifluoromethyl,N'-(n-propyl)ureido, N'-trifluoromethyl,N'-(i-propyl)ureido, N'-trifluoromethyl,N'-(n-butyl)ureido, N'-trifluoromethyl,N'-(sec-butyl)ureido, N'-difluoromethyl,N'-methylureido, N'-difluoromethyl,N'-ethylureido, N'-difluoromethyl,N'(n-propyl)ureido, N'-difluoromethyl,N'-(i-propyl)ureido, N'-difluoromethyl,N'-(n-butyl)ureido, N'-difluoromethyl,N'-(sec-butyl)ureido, N'-difluoromethyl,N'-(t-butyl)ureido, N'-difluoromethyl,N'-trifluoromethylureido, N'-hydroxymethyl,N'-methylureido, N'-ethyl,N'-hydroxymethylureido, N'-hydroxymethyl,N'-(n-propyl)ureido, N'-hydroxymethyl, N'-(i-propyl)ureido, N'-n-butyl,N'-hydroxymethylureido, N'-sec-butyl,N'-hydroxymethylureido, N'-t-butyl,N'-hydroxymethylureido, N'-difluoromethyl,N'-hydroxymethylureido, N'-hydroxymethyl,N'-trifluoromethylureido, N'-hydroxyethyl,N'-methylureido, N'-ethyl,N'-hydroxyethylureido, N'-hydroxyethyl,N'-(n-propyl)ureido, N'-hydroxyethyl,N'-(i-propyl)ureido, N'-(n-butyl),N'-hydroxyethylureido, N'(sec-butyl),N'-hydroxyethylureido, N'-(t-butyl),N'-hydroxyethylureido, N'-difluoromethyl,N'-hydroxyethylureido, N'-hydroxyethyl,N'-trifluoromethylureido, N'-hydroxypropyl,N'-methylureido, N'-ethyl,N'-hydroxypropylureido, N'-hydroxypropyl,N'-(n-propyl)ureido, N'-hydroxypropyl,N'-(i-propyl)ureido, N'-(n-butyl),N'-hydroxypropylureido, N'(sec-butyl),N'-hydroxypropylureido, N'(t-butyl),N'-hydroxypropylureido, N'-difluoromethyl,N'-hydroxypropylureido y N'-hydroxypropyl,N'-trifluoromethylureido.

As used herein, the term acyl embraces optionally substituted, linear or branched radicals having 2 to 20 carbon atoms or, preferably 2 to 12 carbon atoms attached to a carbonyl radical. More preferably acyl radicals are "lower acyl" radicals of formula —COR, wherein R is a hydrocarbon group, preferably an alkyl group, having 2 to 8, preferably 2 to 6 and more preferably 2 to 4 carbon atoms.

An acyl group is typically unsubstituted or substituted with 1, 2 or 3 substituents which may be the same or different. The substitutents are preferably selected from halogen atoms, preferably fluorine atoms, hydroxy groups and alkoxy groups having from 1 to 4 carbon atoms. Typically, the substituents on an acyl group are themselves unsubstituted. Preferred optionally substituted acyl radicals include acetyl, propionyl, butiryl, isobutiryl, isovaleryl, pivaloyil, valeryl, lauryl, myristyl, stearyl and palmityl, As used herein, the term aryl radical embraces typically a $C_5$-$C_{14}$ monocyclic or polycyclic aryl radical such as phenyl, naphthyl, anthranyl and phenanthryl. Phenyl is preferred.

A said optionally substituted aryl radical is typically unsubstituted or substituted with 1, 2 or 3 substituents which may be the same or different. The substitutents are preferably selected from halogen atoms, preferably fluorine atoms, hydroxy groups, alkoxycarbonyl groups in which the alkyl moiety has from 1 to 4 carbon atoms, hydroxycarbonyl groups, carbamoyl groups, nitro groups, cyano groups, $C_1$-$C_4$ alkyl groups, $C_1$-$C_4$ alkoxy groups and $C_1$-$C_4$ hydroxyalkyl groups. When an aryl radical carries 2 or more substituents, the substituents may be the same or different. Unless otherwise specified, the substitutents on an aryl group are typically themselves unsubstituted.

As used herein, the term heteroaryl radical embraces typically a 5- to 14-membered ring system, preferably a 5- to 10-membered ring system, comprising at least one heteroaromatic ring and containing at least one heteroatom selected from O, S and N. A heteroaryl radical may be a single ring or two or more fused rings wherein at least one ring contains a heteroatom.

A said optionally substituted heteroaryl radical is typically unsubstituted or substituted with 1, 2 or 3 substituents which may be the same or different. The substitutents are preferably selected from halogen atoms, preferably fluorine, chlorine or bromine atoms, alkoxycarbonyl groups in which the alkyl moiety has from 1 to 4 carbon atoms, nitro groups, hydroxy groups, $C_1$-$C_4$ alkyl groups and $C_1$-$C_4$ alkoxy groups. When an heteroaryl radical carries 2 or more substituents, the substituents may be the same or different. Unless otherwise specified, the substitutents on a heteroaryl radical are typically themselves unsubstituted.

Examples include pyridyl, pyrazinyl, pyrimidinyl, pyridazinyl, furyl, benzofuranyl, oxadiazolyl, oxazolyl, isoxazolyl, benzoxazolyl, imidazolyl, benzimidazolyl, thiazolyl, thiadiazolyl, thienyl, pyrrolyl, pyridinyl, benzothiazolyl, indolyl, indazolyl, purinyl, quinolyl, isoquinolyl, phthalazinyl, naphthyridinyl, quinoxalinyl, quinazolinyl, quinolizinyl, cinnolinyl, triazolyl, indolizinyl, indolinyl, isoindolinyl, isoindolyl, imidazolidinyl, pteridinyl, thianthrenyl, pyrazolyl, 2H-pyrazolo[3,4-d]pyrimidinyl, 1H-pyrazolo[3,4-d]pyrimidinyl, thieno[2,3-d]pyrimidinyl, thieno[2,3-c]pyridinyl, the various pyrrolopyridyl radicals and the N-oxides thereof.

Oxadiazolyl, oxazolyl, pyridyl, pyrrolyl, imidazolyl, thiazolyl, thiadiazolyl, thienyl, furanyl, quinolinyl, isoquinolinyl, indolyl, benzoxazolyl, naphthyridinyl, benzofuranyl, pyrazinyl, pyrimidinyl, thieno[2,3-c]pyridinyl and the various pyrrolopyridyl radicals are preferred. Quinolin-5-yl, pyrydin3-yl, isoquinolinyl-4yl, 1,7-naphthyridinyl, thieno[2,3-c]pyridine-3-yl and the N-oxides thereof are particularly preferred.

As used herein, the term cycloalkyl embraces saturated carbocyclic radicals and, unless otherwise specified, a cycloalkyl radical typically has from 3 to 7 carbon atoms.

A cycloalkyl radical is typically unsubstituted or substituted with 1, 2 or 3 substituents which may be the same or different. The substitutents are preferably selected from halogen atoms, preferably fluorine atoms, hydroxy groups and alkoxy groups having from 1 to 4 carbon atoms. When a cycloalkyl radical carries 2 or more substitutents, the substitutents may be the same or different. Typically the substitutents on a cycloalkyl group are themselves unsubstituted.

Examples include cyclopropyl, cyclobutyl, cyclopentyl, cyclohexyl and cycloheptyl. It is preferably cyclopropyl, cyclopentyl and cyclohexyl.

As used herein, the term cycloalkenyl embraces partially unsaturated carbocyclic radicals and, unless otherwise specified, a cycloalkenyl radical typically has from 3 to 7 carbon atoms.

A cycloalkenyl radical is typically unsubstituted or substituted with 1, 2 or 3 substituents which may be the same or different. The substitutents are preferably selected from halogen atoms, preferably fluorine atoms, hydroxy groups and alkoxy groups having from 1 to 4 carbon atoms. When a cycloalkenyl radical carries 2 or more substitutents, the substitutents may be the same or different. Typically, the substitutents on a cycloalkenyl group are themselves unsubstituted.

Examples include cyclobutenyl, cyclopentenyl, cyclohexenyl and cycloheptenyl. Cyclopentenyl and cyclohexenyl are preferred.

As used herein, the term heterocyclyl radical embraces typically a non-aromatic, saturated or unsaturated $C_3$-$C_{10}$ carbocyclic ring, such as a 5, 6 or 7 membered radical, in which one or more, for example 1, 2, 3 or 4 of the carbon atoms preferably 1 or 2 of the carbon atoms are replaced by a heteroatom selected from N, O and S. Saturated heterocyclyl radicals are preferred. A heterocyclic radical may be a single ring or two or more fused rings wherein at least one ring contains a heteroatom. When a heterocyclyl radical carries 2 or more substitutents, the substituents may be the same or different.

A said optionally substituted heterocyclyl radical is typically unsubstituted or substituted with 1, 2 or 3 substituents which may be the same or different. The substitutents are preferably selected from halogen atoms, preferably fluorine atoms, hydroxy groups and alkoxy groups having from 1 to 4 carbon atoms. Typically, the substitutents on a heterocyclyl radical are themselves unsubstituted.

Examples of heterocyclic radicals include piperidyl, pyrrolidyl, pyrrolinyl, piperazinyl, morpholinyl, thiomorpholinyl, pyrrolyl, pyrazolinyl, pirazolidinyl, quinuclidinyl, triazolyl, pyrazolyl, tetrazolyl, cromanyl, isocromanyl, imidazolidinyl, imidazolyl, oxiranyl, azaridinyl, 4,5-dihydro-oxazolyl and 3-aza-tetrahydrofuranyl.

Where a heterocyclyl radical carries 2 or more substitutents, the substitutents may be the same or different.

As used herein, some of the atoms, radicals, moieties, chains and cycles present in the general structures of the invention are "optionally substituted". This means that these atoms, radicals, moieties, chains and cycles can be either unsubstituted or substituted in any position by one or more, for example 1, 2, 3 or 4, substitutents, whereby the hydrogen atoms bound to the unsubstituted atoms, radicals, moieties, chains and cycles are replaced by chemically acceptable atoms, radicals, moieties, chains and cycles. When two or more substituents are present, each substitutent may be the same or different. The substitutents are typically themselves unsubstituted.

Typically when a cyclic radical is bridged by an alkylene or alkylenedioxy radical, the bridging alkylene radical is attached to the ring at non-adjacent atoms.

As used herein, the term halogen atom embraces chlorine, fluorine, bromine and iodine atoms. A halogen atom is typically a fluorine, chlorine or bromine atom, most preferably chlorine or fluorine. The term halo when used as a prefix has the same meaning.

As used herein, an acylamino group is typically a said acyl group attached to an amino group.

As used herein an alkylenedioxy group is typically —O—R—O—, wherein R is a said alkylene group.

As used herein, an alkoxycarbonyl group is typically a said alkoxy group attached to a said carbonyl group.

As used herein, an acyloxy group is typically a said acyl group attached to an oxygen atom.

As used herein, a cycloalkoxy group is typically a said cycloalkyl group attached to an oxygen atom.

As used herein the term halophenyl embraces phenyl groups substituted by one or more halogen atoms, preferably phenyl groups substituted by one halogen atom.

Compounds containing one or more chiral centre may be used in enantiomerically or diastereoisomerically pure form, or in the form of a mixture of isomers.

As used herein, the term pharmaceutically acceptable salt embraces salts with a pharmaceutically acceptable acid or base. Pharmaceutically acceptable acids include both inorganic acids, for example hydrochloric, sulphuric, phosphoric, diphosphoric, hydrobromic, hydroiodic and nitric acid and organic acids, for example citric, fumaric, maleic, malic, mandelic, ascorbic, oxalic, succinic, tartaric, benzoic, acetic, methanesulphonic, ethanesulphonic, benzenesulphonic or p-toluenesulphonic acid. Pharmaceutically acceptable bases include alkali metal (e.g. sodium or potassium) and alkali earth metal (e.g. calcium or magnesium) hydroxides and organic bases, for example alkyl amines, arylalkyl amines and heterocyclic amines.

As used herein, an N-oxide is formed from the tertiary basic amines or imines present in the molecule, using a convenient oxidising agent.

According to one embodiment, the present invention provides novel compounds of formula (I):

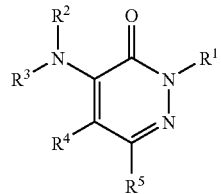

wherein $R^1$ represents:
  a hydrogen atom;
  a group selected from acyl, alkoxycarbonyl, carbamoyl, monoalkylcarbamoyl or dialkylcarbamoyl;
  an alkyl, alkenyl or alkynyl group, which is optionally substituted by one or more substitutents selected from halogen atoms and hydroxy, alkoxy, aryloxy, alkylthio, arylthio, oxo, amino, mono- or di-alkylamino, acylamino, hydroxycarbonyl, alkoxycarbonyl, carbamoyl or mono- or di-alkylcarbamoyl groups;
  an aryl or heteroaryl group which is optionally substituted by one or more substitutents selected from halogen atoms and hydroxy, hydroxyalkyl, hydroxycarbonyl, alkoxy, alkylenedioxy, alkoxycarbonyl, aryloxy, acyl, acyloxy, alkylthio, arylthio, amino, nitro, cyano, mono- or di-alkylamino, acylamino, carbamoyl or mono- or di-alkylcarbamoyl, difluoromethyl, trifluoromethyl, difluoromethoxy or trifluoromethoxy groups;
  a saturated or unsaturated heterocyclic group which is optionally substituted by one or more substitutents selected from halogen atoms and hydroxy, hydroxyalkyl, hydroxycarbonyl, alkoxy, alkylenedioxy, alkoxycarbonyl, aryloxy, acyl, acyloxy, alkylthio, arylthio, oxo, amino, nitro, cyano, mono- or di-alkylamino, acylamino, carbamoyl or mono- or di-alkylcarbamoyl, difluoromethyl, trifluoromethyl, difluoromethoxy or trifluoromethoxy groups;
  a group of formula —$(CH_2)_n$—$R^6$ wherein n is an integer from 0 to 4 and $R^6$ represents:
    a cycloalkyl or cycloalkenyl group;
    an aryl group, which is optionally substituted by one or more substitutents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
    or a 3- to 7-membered ring comprising from 1 to 4 heteroatoms selected from nitrogen, oxygen and sulphur, which ring is optionally substituted by one or more substitutents selected from halogen atoms and alkyl, hydroxy, alkoxy, alkylenedioxy, amino, mono- or di-alkylamino, nitro, cyano or trifluoromethyl groups;

$R^2$ represents:
  a hydrogen atom;
  a group selected from acyl, alkoxycarbonyl, carbamoyl, monoalkylcarbamoyl or dialkylcarbamoyl;
  an alkyl, alkenyl or alkynyl group, which is optionally substituted by one or more substitutents selected from halogen atoms and hydroxy, alkoxy, hydroxycarbonyl, alkoxycarbonyl, aryloxy, alkylthio, arylthio, oxo, amino, mono- or di-alkylamino, acylamino, carbamoyl or mono- or di-alkylcarbamoyl groups;

an aryl or heteroaryl group which is optionally substituted by one or more substitutents selected from halogen atoms and hydroxy, hydroxyalkyl, hydroxycarbonyl, alkoxy, alkylenedioxy, alkoxycarbonyl, aryloxy, acyl, acyloxy, alkylthio, arylthio, amino, nitro, cyano, mono- or di-alkylamino, acylamino, carbamoyl or mono- or di-alkylcarbamoyl, difluoromethyl, trifluoromethyl, difluoromethoxy or trifluoromethoxy groups;

a saturated or unsaturated heterocyclic group which is optionally substituted by one or more substitutents selected from halogen atoms and hydroxy, hydroxyalkyl, hydroxycarbonyl, alkoxy, alkylenedioxy, alkoxycarbonyl, aryloxy, acyl, acyloxy, alkylthio, arylthio, oxo, amino, nitro, cyano, mono- or di-alkylamino, acylamino, carbamoyl or mono- or di-alkylcarbamoyl, difluoromethyl, trifluoromethyl, difluoromethoxy or trifluoromethoxy groups;

a group of formula

—(CH$_2$)$_n$—R$^6$ wherein n is an integer from 0 to 4 and R$^6$ represents:
 a cycloalkyl or cycloalkenyl group;
 an aryl group, which is optionally substituted by one or more substitutents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
 or a 3- to 7-membered ring comprising from 1 to 4 heteroatoms selected from nitrogen, oxygen and sulphur, which ring is optionally substituted by one or more substitutents selected from halogen atoms and alkyl, hydroxy, alkoxy, alkylenedioxy, amino, mono- or di-alkylamino, nitro, cyano or trifluoromethyl groups;

R$^3$ represents a monocyclic or polycyclic aryl or heteroaryl group, which is optionally substituted by one or more substitutents selected from:
 halogen atoms;
 alkyl and alkylene groups, which are optionally substituted by one or more substitutents selected from halogen atoms and phenyl, hydroxy, alkoxy, aryloxy, alkylthio, arylthio, oxo, amino, mono- or di-alkylamino, acylamino, hydroxycarbonyl, alkoxycarbonyl, carbamoyl or mono- or di-alkylcarbamoyl groups
 phenyl, hydroxy, hydroxyalkyl, alkoxy, cycloalkoxy, nitro, cyano, aryloxy, alkylthio, arylthio, alkylsulfinyl, alkylsulfonyl, alkylsulfamoyl, acyl, amino, mono- or di-alkylamino, acylamino, hydroxycarbonyl, alkoxycarbonyl, carbamoyl, mono- or di-alkylcarbamoyl, ureido, N'-alkylureido, N',N'-dialkylureido, alkylsulfamido, aminosuphonyl, mono- or di-alkylaminosulfonyl, cyano, difluoromethoxy or trifluoromethoxy groups;

R$^4$ represents:
 a hydrogen atom;
 a hydroxy, alkoxy, amino, monoalkylamino, dialkylamino or cyano group;
 an alkyl, alkenyl or alkynyl group which is optionally substituted by one or more substitutents selected from halogen atoms and hydroxy, alkoxy, aryloxy, alkylthio, arylthio, amino, mono- or di-alkylamino, acylamino, hydroxycarbonyl, alkoxycarbonyl, alkoxyimino, carbamoyl and mono- or di-alkylcarbamoyl groups;

or a group of formula

—(CH$_2$)$_n$—R$^6$ wherein n is an integer from 0 to 4 and R$^6$ represents:
 a cycloalkyl or cycloalkenyl group;
 an aryl group, which is optionally substituted by one or more substitutents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
 or a 3- to 7-membered ring comprising from 1 to 4 heteroatoms selected from nitrogen, oxygen and sulphur, which ring is optionally substituted by one or more substitutents selected from halogen atoms and alkyl, phenyl, hydroxy, alkoxy, alkylenedioxy, amino, mono- or di-alkylamino, nitro, cyano or trifluoromethyl groups;

R$^5$ represents a group —COOR$^7$ or a monocyclic or polycyclic aryl or heteroaryl group, which is optionally substituted by one or more substitutents selected from:
 halogen atoms;
 alkyl and alkenyl groups, which are optionally substituted by one or more substitutents selected from halogen atoms and phenyl, hydroxy, hydroxyalkyl, alkoxy, aryloxy, alkylthio, arylthio, oxo, amino, mono- or di-alkylamino, acylamino, hydroxycarbonyl, alkoxycarbonyl, carbamoyl, mono- or di-alkylcarbamoyl groups; and
 phenyl, hydroxy, alkylenedioxy, alkoxy, cycloalkyloxy, alkylthio, alkylsulfinyl, alkylsulfonyl, alkylsulfamoyl, amino, mono- or di-alkylamino, acylamino, nitro, acyl, hydroxycarbonyl, alkoxycarbonyl, carbamoyl, mono- or di-alkylcarbamoyl, ureido, N'-alkylureido, N',N'-dialkylureido, alkylsulfamido, aminosuphonyl, mono- or di-alkylaminosulfonyl, cyano, difluoromethoxy or trifluoromethoxy groups;

wherein R$^7$ represents an alkyl group which is optionally substituted by one or more substitutents selected from halogen atoms and hydroxy, alkoxy, aryloxy, alkylthio, arylthio, oxo, amino, mono- or di-alkylamino, acylamino, hydroxycarbonyl, alkoxycarbonyl, carbamoyl, mono- or di-alkylcarbamoyl groups or a group of formula —(CH$_2$)$_n$—R$^6$ wherein n is an integer from 0 to 4 and R$^6$ represents:
 a cycloalkyl or cycloalkenyl group;
 an aryl group, which is optionally substituted by one or more substitutents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
 or a 3- to 7-membered ring comprising from 1 to 4 heteroatoms selected from nitrogen, oxygen and sulphur, which ring is optionally substituted by one or more substitutents selected from halogen atoms and alkyl, phenyl, alkoxyphenyl, halophenyl, pyridyl, alkoxycarbonyl, hydroxy, alkoxy, alkylenedioxy, amino, mono- or di-alkylamino, nitro, cyano or trifluoromethyl groups;

with the proviso that when $R^1$ is methyl, $R^2$ is H, and both $R^3$ and $R^5$ are phenyl then $R^4$ is not a 1-hydroxyethyl group.

and the pharmaceutically acceptable salts or N-oxides thereof.

According to one embodiment of the present invention in the compounds of formula (I) $R^1$ is selected from the group consisting of hydrogen atoms and alkyl groups, which are optionally substituted by one or more substitutents selected from halogen atoms and hydroxy, alkoxy, alkylthio, hydroxycarbonyl and alkoxycarbonyl groups. In a preferred execution $R^1$ is selected from the group consisting of unsubstituted $C_{1-4}$ alkyl groups.

According to another embodiment of the present invention in the compounds of formula (I) $R^2$ is selected from the group consisting of:
  hydrogen atoms,
  an acyl group
  an alkyl group, which is optionally substituted by one or more substitutents selected from halogen atoms and hydroxy, alkoxy and alkylthio groups
  an aryl or heteroaryl group which are optionally substituted by one or more substitutents selected from halogen atoms and hydroxy, hydroxyalkyl, hydroxycarbonyl, alkoxy, alkylenedioxy, alkoxycarbonyl, aryloxy, acyl, acyloxy, alkylthio, arylthio, amino, nitro, cyano, mono- or di-alkylamino, acylamino, carbamoyl or mono- or di-alkylcarbamoyl, difluoromethyl, trifluoromethyl, difluoromethoxy or trifluoromethoxy groups;

In a preferred execution of this embodiment $R^2$ is represents a hydrogen atom.

According to still another embodiment of the present invention in the compounds of formula (I) $R^3$ represents a monocyclic or polycyclic, aryl or heteroaryl group, which is optionally substituted by one or more substitutents selected from:
  halogen atoms;
  alkyl and alkylene groups, which are optionally substituted by one or more substitutents selected from halogen atoms and phenyl, hydroxy, alkoxy, aryloxy, alkylthio, arylthio, oxo, amino, mono- or di-alkylamino, acylamino, hydroxycarbonyl, alkoxycarbonyl, carbamoyl or mono- or di-alkylcarbamoyl groups
  phenyl, hydroxy, hydroxyalkyl, alkoxycarbonyl, alkoxy, cycloalkoxy, nitro, cyano, aryloxy, alkylthio, arylthio, alkylsulfinyl, alkylsulfonyl, alkylsulfamoyl, acyl, amino, mono- or di-alkylamino, acylamino, hydroxycarbonyl, carbamoyl, mono- or di-alkylcarbamoyl, ureido, N'-alkylureido, N',N'-dialkylureido, alkylsulfamido, aminosuphonyl, mono- or di-alkylaminosulfonyl, difluoromethoxy or trifluoromethoxy groups;

According to still another embodiment of the present invention in the compounds of formula (I) $R^3$ represents a monocyclic or polycyclic, aryl or heteroaryl group, which is optionally substituted by one substitutent selected from halogen atoms, alkyl groups and hydroxycarbonyl groups. In a preferred execution $R^3$ represents a phenyl group or a monocyclic or polycyclic N-containing heteroaryl group which groups may be substituted by one substitutent selected from halogen atoms, alkyl groups and hydroxycarbonyl groups.

According to still another embodiment of the present invention in the compounds of formula (I) $R^4$ represents:
  a hydrogen atom;
  a cyano group;
  an alkyl, alkenyl or alkynyl group which is optionally substituted by one or more substitutents selected from halogen atoms and hydroxy, acyloxy, alkoxy, aryloxy, alkylthio, arylthio, amino, mono- or di-alkylamino, acylamino, hydroxycarbonyl, alkoxycarbonyl, carbamoyl and mono- or di-alkylcarbamoyl groups;
  or a group of formula $$-(CH_2)_n-R^6$$

wherein n is an integer from 0 to 4 and $R^6$ represents a 3- to 7-membered ring comprising from 1 to 4 heteroatoms selected from nitrogen, oxygen and sulphur, which ring is optionally substituted by one or more substitutents selected from halogen atoms and alkyl, phenyl, alkoxyphenyl, halophenyl, pyridyl, alkoxycarbonyl, hydroxy, alkoxy, alkylenedioxy, amino, mono- or di-alkylamino, nitro, cyano or trifluoromethyl groups;

According to still another embodiment of the present invention in the compounds of formula (I) $R^4$ represents:
  a hydrogen atom;
  a cyano group;
  an alkyl, alkenyl or alkynyl group which is optionally substituted by one or more substitutents selected from halogen atoms and hydroxy, alkoxy, aryloxy, alkylthio, arylthio, amino, mono- or di-alkylamino, acylamino, hydroxycarbonyl, alkoxycarbonyl, carbamoyl and mono- or di-alkylcarbamoyl groups;
  or a group of formula $$-(CH_2)_n-R^6$$

wherein n is an integer from 0 to 4 and $R^6$ represents a 3- to 7-membered ring comprising from 1 to 4 heteroatoms selected from nitrogen, oxygen and sulphur, which ring is optionally substituted by one or more substitutents selected from halogen atoms and alkyl, phenyl, hydroxy, alkoxy, alkylenedioxy, amino, mono- or di-alkylamino, nitro, cyano or trifluoromethyl groups;

According to another embodiment of the present invention in the compounds of formula (I) $R^4$ represents a hydrogen atom or a cyano group.

According to another embodiment of the present invention in the compounds of formula (I) $R^5$ represents a group $-COOR^7$ or a monocyclic or polycyclic aryl or heteroaryl group, which is optionally substituted by one or more substitutents selected from:
  halogen atoms;
  alkyl groups, which are optionally substituted by one or more substituents selected from halogen atoms and hydroxy, hydroxyalkyl, alkoxy, alkylthio, mono- or di-alkylamino, acylamino, hydroxycarbonyl, alkoxycarbonyl, carbamoyl, mono- or di-alkylcarbamoyl groups; and hydroxy, alkylenedioxy, alkoxy, cycloalkyloxy, alkylthio, alkylsulfinyl, alkylsulfonyl, alkylsulfamoyl, amino, mono- or di-alkylamino, acylamino, nitro, acyl, hydroxycarbonyl, alkoxycarbonyl, carbamoyl, mono- or di-alkylcarbamoyl, ureido, N'-alkylureido, N',N'-dialkylureido, alkylsulfamido, aminosulfonyl, mono- or di-alkylaminosulfonyl, cyano, difluoromethoxy or trifluoromethoxy groups;

wherein $R^7$ represents an alkyl which is optionally substituted by one or more substitutents selected from halogen atoms and hydroxy, alkoxy, aryloxy, alkylthio, arylthio, oxo, amino, mono- or di-alkylamino, acylamino, hydroxycarbonyl, alkoxycarbonyl, carbamoyl, mono- or di-alkylcarbamoyl groups or a group of formula $$-(CH_2)_n-R^6$$

wherein n is an integer from 0 to 4 and $R^6$ represents:
a cycloalkyl or cycloalkenyl group;
an aryl group, which is optionally substituted by one or more substitutents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
or a 3- to 7-membered ring comprising from 1 to 4 heteroatoms selected from nitrogen, oxygen and sulphur, which ring is optionally substituted by one or more substitutents selected from halogen atoms and alkyl, phenyl, hydroxy, alkoxy, alkylenedioxy, amino, mono- or di-alkylamino, nitro, cyano or trifluoromethyl groups;

According to still another embodiment of the present invention in the compounds of formula (I) $R^5$ represents a monocyclic aryl or heteroaryl group, which is optionally substituted by one or more substitutents selected from halogen atoms and alkyl groups.

According to another embodiment of the present invention in the compounds of formula (I) $R^1$ is selected from the group consisting of hydrogen atoms and alkyl groups, which are optionally substituted by one or more substitutents selected from halogen atoms and hydroxy, alkoxy, alkylthio, hydroxycarbonyl and alkoxycarbonyl groups and $R^2$ is selected from the group consisting of:
hydrogen atoms,
an acyl group
an alkyl group, which is optionally substituted by one or more substitutents selected from halogen atoms and hydroxy, alkoxy and alkylthio groups
an aryl or heteroaryl group which are optionally substituted by one or more halogen atoms.

According to still another embodiment of the present invention in the compounds of formula (I) $R^1$ is selected from the group consisting of unsubstituted $C_{1-4}$ alkyl groups and $R^2$ is a hydrogen atom.

According to still another embodiment of the present invention, according to the above-mentioned embodiments, in the compounds of formula (I) $R^3$ represents a monocyclic or polycyclic, aryl or heteroaryl group, which is optionally substituted by one or more substitutents selected from:
halogen atoms;
alkyl groups, which are optionally substituted by one or more substitutents selected from halogen atoms and hydroxy groups
cyano, hydroxycarbonyl groups;

According to still another embodiment of the present invention, according to the above-mentioned embodiments, in the compounds of formula (I) $R^3$ represents a phenyl group or a monocyclic or polycyclic N-containing heteroaryl group which groups may be substituted by one substitutent selected from halogen atoms, alkyl groups and hydroxycarbonyl groups.

According to another embodiment of the present invention in the compounds of formula (I), according to the above-mentioned embodiments, $R^4$ represents:
a hydrogen atom;
a cyano group;
an alkyl, alkenyl or alkynyl group which is optionally substituted by one or more substitutents selected from halogen atoms and hydroxyl and alkoxy groups;
or a group of formula —$(CH_2)_n$—$R^6$ wherein n is 0 and $R^6$ represents a 3- to 7-membered ring comprising from 1 to 4 heteroatoms selected from nitrogen, oxygen and sulphur, which ring is optionally substituted by one or more substitutents selected from halogen atoms and alkyl and phenyl groups According to still another embodiment of the present invention in the compounds of formula (I), according to the above-mentioned embodiments, $R^5$ represents a group —$COOR^7$ or a monocyclic or polycyclic aryl or heteroaryl group, which is optionally substituted by one or more substituents selected from:
halogen atoms;
alkyl groups, which are optionally substituted by one or more substitutents selected from halogen atoms and hydroxyl and alkoxy groups; and
alkoxy, alkoxycarbonyl and hydroxycarbonyl groups;
wherein $R^7$ represents an alkyl group which is optionally substituted by one or more substituents selected from halogen atoms and hydroxyl and alkoxy groups or a group of formula —$(CH_2)_n$—$R^6$ wherein n is an integer from 0 to 4 and $R^6$ represents:
a cycloalkyl or cycloalkenyl group;
an aryl group, which is optionally substituted by one or more substitutents selected from halogen atoms and alkyl, hydroxy, alkoxy, alkylenedioxy, alkylthio, amino, mono- or di-alkylamino, nitro, acyl, hydroxycarbonyl, alkoxycarbonyl, carbamoyl, mono- or di-alkylcarbamoyl, cyano, trifluoromethyl, difluoromethoxy or trifluoromethoxy groups;
or a 3- to 7-membered ring comprising from 1 to 4 heteroatoms selected from nitrogen, oxygen and sulphur, which ring is optionally substituted by one or more substitutents selected from halogen atoms and alkyl, phenyl, hydroxy, alkoxy, alkylenedioxy, amino, mono- or di-alkylamino, nitro, cyano or trifluoromethyl groups;

According to another embodiment of the present invention in the compounds of formula (I), according to the above-mentioned embodiments, $R^5$ represents a monocyclic or polycyclic aryl or heteroaryl group, which is optionally substituted by one or more substituents selected from:
halogen atoms;
alkyl groups, which are optionally substituted by one or more substitutents selected from halogen atoms and hydroxyl and alkoxy groups; and
alkoxy groups According to another embodiment of the present invention in the compounds of formula (I), according to the above-mentioned embodiments $R^4$ represents a hydrogen atom or a cyano group and $R^5$ represents a monocyclic aryl or heteroaryl group, which is optionally substituted by one or more substitutents selected from halogen atoms and alkyl groups. It is particularly preferred that $R^5$ represents a monocyclic aryl or heteroaryl group, which is optionally substituted by one or more substitutents selected from halogen atoms and alkyl groups.

According to still another embodiment of the present invention in the compounds of formula (I) $R^1$ represents an alkyl group, $R^2$ represents a hydrogen atom or a group selected from acyl, alkyl, aryl or heteroaryl groups which are optionally substituted by one or more halogen atoms, $R^3$ represents a monocyclic or polycyclic aryl or heteroaryl group, which is optionally substituted by one or more substitutents selected from halogen atoms, cyano, hydroxycarbonyl and alkyl groups, which are optionally substituted by one or more hydroxy groups, $R^4$ represents a hydrogen atom, a cyano group, an alkyl or alkenyl group which are optionally substituted by one substitutent selected from hydroxyl and alkoxy groups or a group of formula ($-R^6$) wherein $R^6$ represents a 4- to 6-membered ring comprising from 1 to 3 heteroatoms selected from nitrogen, oxygen and sulphur, which ring is optionally substituted by one substitutent selected from alkyl and phenyl groups and $R^5$ represents a monocyclic aryl or heteroaryl group, which is optionally substituted by one substitutent selected from halogen atoms, alkyl and alkoxy groups;

According to still another embodiment of the present invention in the compounds of formula (I) $R^1$ is selected from the group consisting of unsubstituted $C_{1-4}$ alkyl groups; $R^2$ is a hydrogen atom; $R^3$ represents a phenyl group or a monocyclic or polycyclic N-containing heteroaryl group which groups may be substituted by one substitutent selected from halogen atoms, alkyl groups and hydroxycarbonyl groups; $R^4$ represents a hydrogen atom or a cyano group and $R^5$ represents a monocyclic aryl or heteroaryl group, which is optionally substituted by one or more substitutents selected from halogen atoms and alkyl groups.

Particular individual compounds of the invention include:
4-[(3-chlorophenyl)amino]-2-ethyl-5-(1-hydroxyethyl)-6-phenylpyridazin-3(2H)-one
4-[(3-chlorophenyl)amino]-2-ethyl-5-(1-methoxyethyl)-6-phenylpyridazin-3(2H)-one
4-[(3-chlorophenyl)amino]-2-ethyl-6-phenyl-5-vinylpyridazin-3(2H)-one
4-anilino-2,5-diethyl-6-phenylpyridazin-3(2H)-one
5-[(3-chlorophenyl)amino]-1-ethyl-6-oxo-3-phenyl-1,6-dihydropyridazine-4-carbaldehyde O-methyloxime
5-[(3-chlorophenyl)amino]-1-ethyl-6-oxo-3-phenyl-1,6-dihydropyridazine-4-carbonitrile
1-ethyl-5-{[4-(hydroxymethyl)phenyl]amino}-6-oxo-3-phenyl-1,6-dihydropyridazine-4-carbonitrile
1-ethyl-6-oxo-3-phenyl-5-[(3,4,5-trifluorophenyl)amino]-1,6-dihydropyridazine-4-carbonitrile
5-[(4-cyanophenyl)amino]-1-ethyl-6-oxo-3-phenyl-1,6-dihydropyridazine-carbonitrile
1-ethyl-3-(4-fluorophenyl)-5-{[4-(hydroxymethyl)phenyl]amino}-6-oxo-1,6-dihydropyridazine-4-carbonitrile
5-[(4-cyanophenyl)amino]-1-ethyl-3-(4-fluorophenyl)-6-oxo-1,6-dihydropyridazine-4-carbonitrile
1-ethyl-3-(4-fluorophenyl)-6-oxo-5-[(3,4,5-trifluorophenyl)amino]-1,6-dihydropyridazine-4-carbonitrile
1-ethyl-3-(4-fluorophenyl)-6-oxo-5-(pyridin-3-ylamino)-1,6-dihydropyridazine-4-carbonitrile
1-ethyl-3-(3-fluorophenyl)-5-{[4-(hydroxymethyl)phenyl]amino}-6-oxo-1,6-dihydropyridazine-4-carbonitrile
5-[(4-cyanophenyl)amino]-1-ethyl-3-(3-fluorophenyl)-6-oxo-1,6-dihydropyridazine-4-carbonitrile
1-ethyl-3-(3-fluorophenyl)-6-oxo-5-[(3,4,5-trifluorophenyl)amino]-1,6-dihydropyridazine-4-carbonitrile
4-[(3-chlorophenyl)amino]-2-ethyl-5-(2-methyl-1,3-thiazol-4-yl)-6-phenylpyridazin-3(2H)-one
4-[(3-chlorophenyl)amino]-2-ethyl-6-phenyl-5-(2-phenyl-1,3-thiazol-4-yl)pyridazin-3(2H)-one
4-[(3-chlorophenyl)amino]-2-ethyl-5-(1-methyl-1H-pyrazol-5-yl)-6-phenylpyridazin-3(2H)-one
4-{[2-ethyl-5-(5-methyl-1,3,4-oxadiazol-2-yl)-3-oxo-6-phenyl-2,3-dihydropyridazin-4-yl]amino}benzonitrile
2-ethyl-5-(5-methyl-1,3,4-oxadiazol-2-yl)-6-phenyl-4-[(3,4,5-trifluorophenyl)amino]pyridazin-3(2H)-one
4-[(3-chlorophenyl)amino]-2-ethyl-6-phenylpyridazin-3(2H)-one
2-ethyl-4-[(3-fluorophenyl)amino]-6-phenylpyridazin-3(2H)-one
2-ethyl-4-(1-naphthylamino)-6-phenylpyridazin-3(2H)-one
2-ethyl-6-phenyl-4-(pyridin-3-ylamino)pyridazin-3(2H)-one
2-ethyl-6-phenyl-4-(quinolin-5-ylamino)pyridazin-3(2H)-one
4-(diquinolin-5-ylamino)-2-ethyl-6-phenylpyridazin-3(2H)-one
4-[bis(3,4,5-trifluorophenyl)amino]-2-ethyl-6-phenylpyridazin-3(2H)-one
4-[bis(3,4-difluorophenyl)amino]-2-ethyl-6-phenylpyridazin-3(2H)-one
4-[(3,4-difluorophenyl)amino]-2-ethyl-6-phenylpyridazin-3(2H)-one
4-[(3-chloro-4-fluorophenyl)amino]-2-ethyl-6-phenylpyridazin-3(2H)-one
4-[(2-ethyl-3-oxo-6-phenyl-2,3-dihydropyridazin-4-yl)amino]benzonitrile
2-ethyl-4-[(1-oxidopyridin-3-yl)amino]-6-phenylpyridazin-3(2H)-one
2-ethyl-6-pyridin-3-yl-4-(pyridin-3-ylamino)pyridazin-3(2H)-one
2-ethyl-4-[(1-oxidoquinolin-5-yl)amino]-6-phenylpyridazin-3(2H)-one
2-ethyl-6-pyridinyl-4-(pyridin-3-ylamino)pyridazin-3(2H)-one
2-ethyl-4-(isoquinolin-4-ylamino)-6-phenylpyridazin-3(2H)-one
2-ethyl-6-phenyl-4-[(3,4,5-trifluorophenyl)amino]pyridazin-3(2H)-one
2-ethyl-4-[(4-fluorophenyl)amino]-6-phenylpyridazin-3(2H)-one
2-ethyl-6-pyridin-3-yl-4-(quinolin-5-ylamino)pyridazin-3(2H)-one
2-methyl-6-pyridin-3-yl-4-(quinolin-5-ylamino)pyridazin-3(2H)-one
2-ethyl-6-pyridin-4-yl-4-(quinolin-5-ylamino)pyridazin-3(2H)-one
2-ethyl-4-{[4-(hydroxymethyl)phenyl]amino}-6-phenylpyridazin-3(2H)-one
4-[(2-methyl-3-oxo-6-pyridin-3-yl-2,3-dihydropyridazin-4-yl)amino]benzonitrile
4-[(2-ethyl-3-oxo-6-pyridin-3-yl-2,3-dihydropyridazin-4-yl)amino]benzonitrile
methyl 4-[(2-ethyl-3-oxo-6-phenyl-2,3-dihydropyridazin-4-yl)amino]benzoate
4-{[2-ethyl-6-(1-oxidopyridin-3-yl)-3-oxo-2,3-dihydropyridazin-4-yl]amino}benzonitrile
2-ethyl-4-(isoquinolin-4-ylamino)-6-pyridin-3-ylpyridazin-3(2H)-one
2-ethyl-4-[(4-methylpyridin-3-yl)amino]-6-pyridin-3-ylpyridazin-3(2H)-one
2-ethyl-4-(isoquinolin-4-ylamino)-6-pyridin-4-ylpyridazin-3(2H)-one
4-[(2-ethyl-3-oxo-6-phenyl-2,3-dihydropyridazin-4-yl)amino]benzoic acid
2-ethyl-4-[(4-methylpyridin-3-yl)amino]-6-pyridin-4-ylpyridazin-3(2H)-one
4-[(2-ethyl-3-oxo-6-pyridin-4-yl-2,3-dihydropyridazin-4-yl)amino]benzonitrile 4-[(2-ethyl-3-oxo-6-phenyl-2,3-dihydropyridazin-4-yl)(methyl)amino]benzonitrile N-(4-cyanophenyl)-N-(2-ethyl-3-oxo-6-phenyl-2,3-dihydropyridazin-4-yl)acetamide 6-(3-chlorophenyl)-2-ethyl-4-(pyridin-3-ylamino)pyridazin-3(2H)-one 2-ethyl-4-[methyl(quinolin-5-yl)amino]-6-phenylpyridazin-3(2H)-one 6-(3-chlorophenyl)-2-ethyl-4-(isoquinolin-4-ylamino)pyridazin-3(2H)-one N-(2-ethyl-3-oxo-6-phenyl-2,3-dihydropyridazin-4-yl)-N-quinolin-5-yl acetamide 2-Ethyl-4-(4-hydroxymethyl-phenylamino)-6-pyridin-3-ylpyridazin-3(2H)-one 2-ethyl-4-(isoquinolin-4-ylamino)-6-(4-methoxyphenyl)pyridazin-3(2H)-one 2-ethyl-6-(4-methoxyphenyl)-4-(quinolin-5-ylamino)pyridazin-3(2H)-one 4-anilino-2-ethyl-6-phenylpyridazin-3(2H)-one 2-ethyl-6-(4-methylphenyl)-4-(quinolin-5-ylamino)pyridazin-3(2H)-one 2-ethyl-6-(4-methylphenyl)-4-[(1-oxidoquinolin-5-yl)amino]pyridazin-3(2H)-one 2-Ethyl-6-phenyl-4-(thieno[2,3-c]pyridin-3-ylamino)pyridazin-3(2H)-one 1-Ethyl-6-oxo-3-phenyl-5-(pyridin-3-ylamino)-1,6-dihydropyridazine-4-carbonitrile 1-Ethyl-3-(3-methylphenyl)-6-oxo-5-(pyridin-3-ylamino)-1,6-dihydropyridazine-4-carbonitrile 2-Ethyl-5-(1-hydroxyethyl)-6-phenyl-4-(quinolin-5-ylamino)pyridazin-3(2H)-one 2-Ethyl-6-(4-methylphenyl)-4-(pyridin-3-ylamino)pyridazin-3(2H)-one 2-Ethyl-4-(isoquinolin-4-ylamino)-6-(4-methylphenyl)pyridazin-3(2H)-one 2-Ethyl-6-(4-methylphenyl)-4-[(4-methylpyridin-3-yl)amino]pyridazin-3(2H)-one 2-Ethyl-6-(3-methylphenyl)-4-(pyridin-3-ylamino)pyridazin-3(2H)-one 2-Ethyl-4-(isoquinolin-4-ylamino)-6-(3-methylphenyl)pyridazin-3(2H)-one 2-Ethyl-6-(3-methylphenyl)-4-[(4-methylpyridin-3-yl)amino]pyridazin-3(2H)-one 4-{[2-Ethyl-6-(3-methylphenyl)-3-oxo-2,3-dihydropyridazin-4-yl]amino}benzoic acid 2-Ethyl-6-(5-methylpyridin-3-yl)-4-(pyridin-3-ylamino)pyridazin-3(2H)-one 2-Ethyl-4-(isoquinolin-4-ylamino)-6-(5-methylpyridin-3-yl)pyridazin-3(2H)-one 2-Ethyl-6-(5-methylpyridin-3-yl)-4-[(4-methylpyridin-3-yl)amino]pyridazin-3(2H)-one 2-Ethyl-4-(1,7-naphthyridin-5-ylamino)-6-phenylpyridazin-3(2H)-one

[1-Ethyl-6-oxo-3-phenyl-5-(pyridin-3-ylamino)-1,6-dihydropyridazin-4-yl]methyl acetate

[1-Ethyl-6-oxo-3-phenyl-5-(pyridin-3-ylamino)-1,6-dihydropyridazin-4-yl]methyl butyrate 2-Ethyl-5-[2-(4-methoxyphenyl)-1,3-thiazol-4-yl]-6-phenyl-4-(pyridin-3-ylamino)pyridazin-3(2H)-one 2-Ethyl-4-(isoquinolin-4-ylamino)-6-(6-methylpyridin-3-yl)pyridazin-3(2H)-one 2-Ethyl-6-(6-methylpyridin-3-yl)-4-(pyridin-3-ylamino)pyridazin-3(2H)-one 2-Ethyl-5-[2-(4-methoxyphenyl)-1,3-thiazol-4-yl]-4-[(4-methylpyridin-3-yl)amino]-6-phenylpyridazin-3(2H)-one 2-Ethyl-6-phenyl-4-(pyridin-3-ylamino)-5-(2-pyridin-4-yl-1,3-thiazol-4-yl)pyridazin-3(2H)-one Ethyl 4-[1-ethyl-6-oxo-3-phenyl-5-(pyridin-3-ylamino)-1,6-dihydropyridazin-4-yl]-1,3-thiazole-2-carboxylate 2-Ethyl-4-(isoquinolin-4-ylamino)-5-[2-(4-methoxyphenyl)-1,3-thiazol-4-yl]-6-phenylpyridazin-3(2H)-one 2-Ethyl-4-[(4-methylpyridin-3-yl)amino]-6-phenyl-5-(2-pyridinyl-1,3-thiazol-4-yl)pyridazin-3(2H)-one 5-[2-(4-Chlorophenyl)-1,3-thiazol-4-yl]-2-ethyl-4-[(4-methylpyridin-3-yl)amino]-6-phenylpyridazin-3(2H)-one 5-[2-(4-Chlorophenyl)-1,3-thiazol-4-yl]-2-ethyl-6-phenyl-4-(pyridin-3-ylamino)pyridazin-3(2H)-one 5-[2-(4-Chlorophenyl)-1,3-thiazol-4-yl]-2-ethyl-4-(isoquinolin-4-ylamino)-6-phenylpyridazin-3(2H)-one 2-Ethyl-4-[(4-methylpyridin-3-yl)amino]-6-phenylpyridazin-3(2H)-one 2-Ethyl-4-[(4-methyl-1-oxidopyridin-3-yl)amino]-6-phenylpyridazin-3(2H)-one Ethyl 4-[(2-ethyl-3-oxo-6-phenyl-2,3-dihydropyridazin-4-yl)amino]benzoate.

and pharmaceutically acceptable salts thereof.

Of outstanding interest are:

1-Ethyl-5-{[4-(hydroxymethyl)phenyl]amino}-6-oxo-3-phenyl-1,6-dihydropyridazine-4-carbonitrile 5-[(4-Cyanophenyl)amino]-1-ethyl-3-(3-fluorophenyl)-6-oxo-1,6-dihydropyridazine-4-carbonitrile 1-ethyl-3-(4-fluorophenyl)-6-oxo-5-(pyridin-3-ylamino)-1,6-dihydropyridazine-4-carbonitrile 4-[(3-Chlorophenyl)amino]-2-ethyl-6-phenyl-5-(2-phenyl-1,3-thiazol-4-yl)pyridazin-3(2H)-one 2-Ethyl-5-(5-methyl-1,3,4-oxadiazol-2-yl)-6-phenyl-4-[(3,4,5-trifluorophenyl)amino]pyridazin-3(2H)-one 2-Ethyl-6-phenyl-4-(quinolin-5-ylamino)pyridazin-3(2H)-one 2-Ethyl-4-[(1-oxidopyridin-3-yl)amino]-6-phenylpyridazin-3(2H)-one 2-Ethyl-4-[(1-oxidoquinolin-5-yl)amino]-6-phenylpyridazin-3(2H)-one 2-Ethyl-6-pyridin-4-yl-4-(pyridin-3-ylamino)pyridazin-3(2H)-one 2-Ethyl-4-(isoquinolin-4-ylamino)-6-pyridin-4-ylpyridazin-3(2H)-one 2-Ethyl-4-[methyl(quinolin-5-yl)amino]-6-phenylpyridazin-3(2H)-one 6-(3-Chlorophenyl)-2-ethyl-4-(isoquinolin-4-ylamino)pyridazin-3(2H)-one and pharmaceutically acceptable salts thereof.

The compounds of the present invention may be prepared by one of the processes described below.

Compounds of formula (I) including those of formula (Ia) wherein $R^2$ is H may be obtained through the reaction paths shown in Scheme 1.

Scheme 1

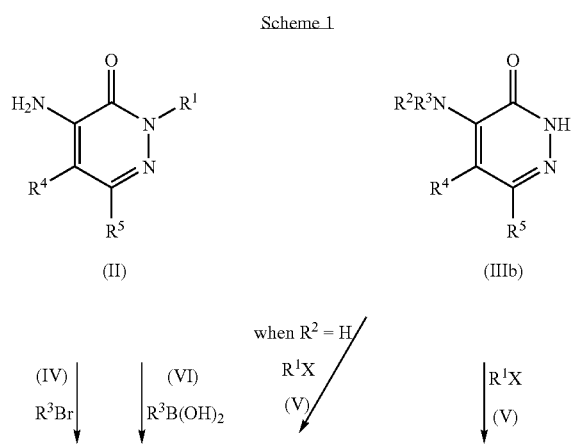

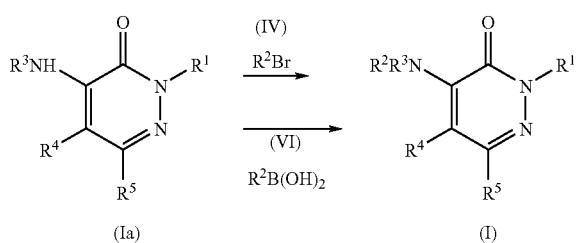

Condensation of a 4-aminopyridazin-3(2H)-one derivative (II), wherein $R^1$, $R^4$ and $R^5$ are as hereinbefore defined, with an aryl or heteroaryl bromide (IV), wherein $R^3$ is as hereinbefore defined, gives compounds (Ia). The reaction is carried out in the presence of a copper salt such as cuprous iodide in the presence of an organic base, preferably a diamine base such as N,N'-dimethylethylenediamine and of an inorganic base such as potassium phosphate in an inert solvent such as toluene, dioxane or dimethylformamide, at a temperature from −20° C. to the boiling point of the solvent.

Alternatively, condensation of 4-aminopyridazin-3(2H)-one derivatives (II), wherein $R^1$, $R^4$ and $R^5$ are as hereinbefore defined, with boronic acids (VI), wherein $R^3$ is as hereinbefore defined, gives compounds (Ia). The reaction is carried out in the presence of a copper salt such as cupric acetate in the presence of an organic base, preferably an amine base such as triethylamine, in an inert solvent such as dioxane, methylene chloride or tetrahydrofuran, at a temperature from −20° C. to the boiling point of the solvent.

The compounds (Ia), wherein $R^1$, $R^3$, $R^4$ and $R^5$ are as hereinabove-defined, can be condensed with boronic acids $R^2(BOH)_2$, wherein $R^2$ is as hereinbefore defined, to give compounds of formula (I). The reaction is carried out in the presence of a copper salt such as cupric acetate in the presence of an organic base, preferably an amine base such as triethylamine, in an inert solvent such as dioxane, methylene chloride or tetrahydrofuran, at a temperature from −20° C. to the boiling point of the solvent.

Compounds of formula (Ia), wherein $R^1$, $R^3$, $R^4$ and $R^5$ are as hereinabove-defined, can alternatively be condensed with an aryl or heteroaryl bromide $R^2Br$, wherein $R^2$ is as hereinbefore defined to give compounds of formula (I). The reaction is carried out in the presence of a copper salt such as cuprous iodide in the presence of an organic base, preferably a diamine base such as N,N'-dimethylethylenediamine and of an inorganic base such as potassium phosphate in an inert solvent such as toluene, dioxane or dimethylformamide, at a temperature from −20° C. to the boiling point of the solvent.

In still another alternative, alkylation of pyridazin-3(2H)-ones (III), wherein $R^2$, $R^3$, $R^4$ and $R^5$ are as hereinbefore defined, with alkylating agents of formula (V), wherein $R^1$ is as hereinbefore defined and X is a leaving group such as a chlorine or a bromine atom or a methanesulfonate, p-toluenesulfonate or a benzenesulfonate group, gives compounds (Ia) or (I). The reaction is preferably in the presence of an inorganic base, such as potassium carbonate or sodium hydride, in a polar aprotic solvent such as dimethylformamide or dimethylsulfoxide, at a temperature from room temperature to 90° C.

Scheme 2

4-aminopyridazin-3(2H)-one derivatives (II) may be obtained as shown in Scheme 2 from the reaction of pyridazin-3(2H) ones (VII) with hydrazine monohydrate by methods known per se, e.g. W. J. Coates et al., Heterocylces 1989, 29 1077.

The pyridazin-3(2H) one (VII) derivatives may be obtained through the reaction paths shown in Scheme 2.

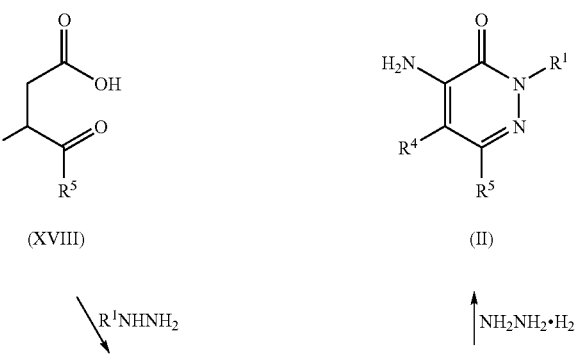

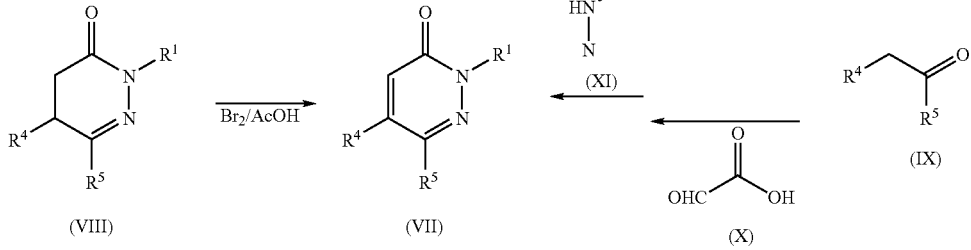

In one possible execution dihydropyridazinones (VIII), wherein $R^1$, $R^4$ and $R^5$ are as hereinbefore defined, are oxidized by the action of bromine in acetic acid by methods known per se, e.g. E. A. Steck et al., *J. Heterocycl. Chem.* 1974, 11, 755, to the corresponding pyridazin-3(2H)-ones (VII).

The 4,5-dihydropyridazin-3(2H)-ones (VIII) are obtained by condensation of ketoacids of formula (XVIII), wherein $R^4$ and $R^5$ are as hereinabove-defined, with a hydrazine of formula $R^1NHNH_2$, wherein $R^1$ is as hereinabove-defined, by methods known per se, e.g. E. A. Steck et al., *J. Heterocycl. Chem.* 1974, 11, 755.

In an alternative embodiment ketones of formula (IX), wherein $R^4$ and $R^5$ are as hereinabove-defined, are condensed with glyoxylic acid and then with a hydrazine of formula (XI), wherein $R^1$ is as hereinbefore defined, in a one-pot reaction, by methods known per se, e.g. W. J. Coates et al. *Synthesis* 1993, 334, to give pyridazin-3(2H)-ones Scheme 3

Compounds of formula (III) may be obtained through the reaction paths shown in Scheme 3.

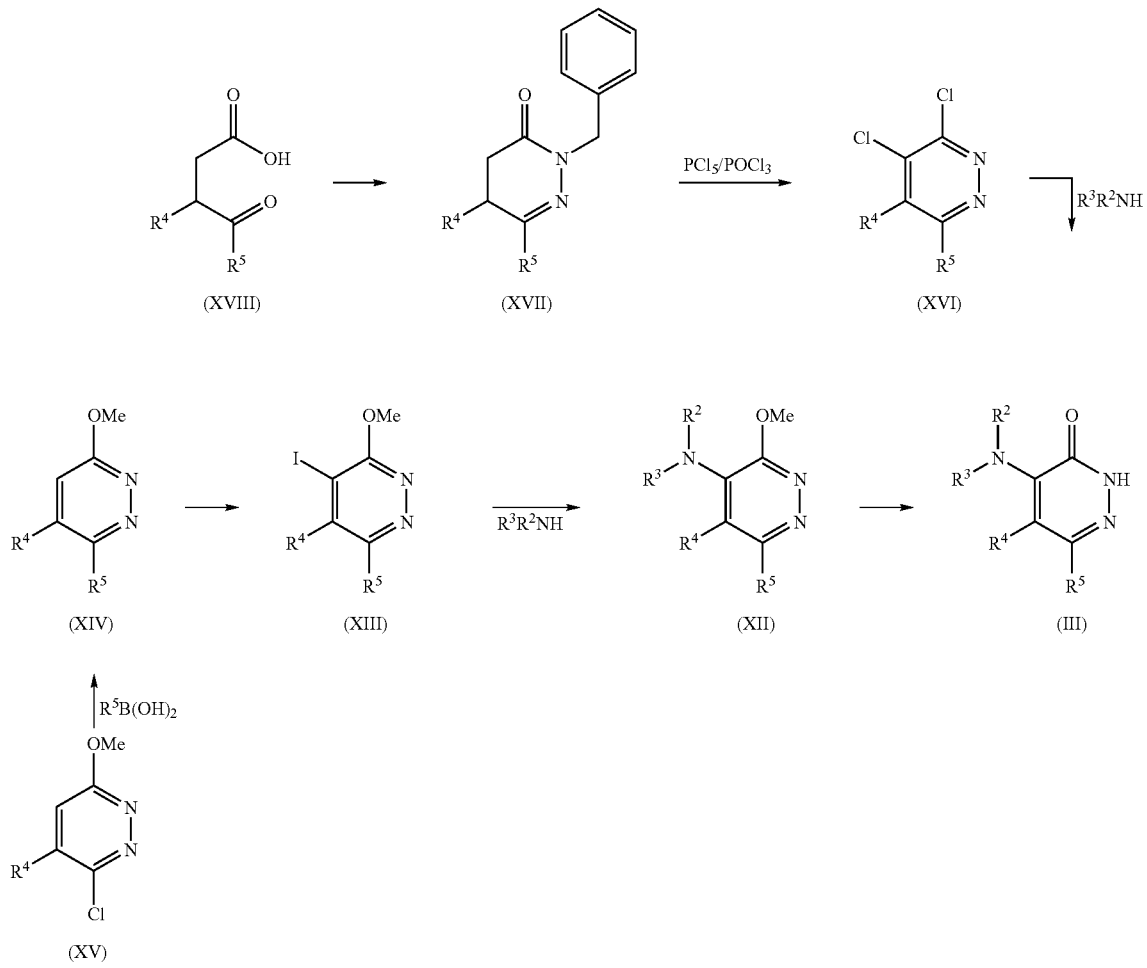

Ketoacids of formula (XVIII), where $R^4$ and $R^5$ is as hereinbefore defined, are condensed with benzylhydrazine by methods known per se, e.g. I. Sircar et al., *J. Heterocycl. Chem.* 1983, 20, 1473, to give 4,5-dihydropyridazin-3(2H)-ones (XVII).

Treatment of 4,5-dihydropyridazin-3(2H)-ones (XVII), wherein $R^4$ and $R^5$ are as hereinabove-defined, with a mixture of phosphorus pentachloride and phosphoryl chloride, by methods known per se, e.g. I. Sircar et al., *J. Heterocycl. Chem.* 1983, 20, 1473, affords 3,4-dichloropyridazines (XVI).

Subsequent reaction of 3,4-dichloropyridazines (XVI), wherein $R^4$ and $R^5$ are as hereinabove-defined, with aryl or heteroarylamines of formula $R^2R^3NH$ wherein $R^2$ and $R^3$ are as hereinbefore defined, in the presence of an inorganic base, such as potassium carbonate or sodium carbonate, gives pyridazin-3(2H)-ones (III). The reaction is preferably carried out in a solvent such as ethanol at a temperature between room temperature to the boiling point of the solvent.

Alternatively pyridazin-3(2H)-ones of formula (III) may be obtained by cleavage of 3-methoxypyridazin-4-amines of formula (XII) wherein $R^3$, $R^4$ and $R^5$ are as hereinbefore defined, by the action of a mixture of trimethylsilyl chloride and sodium iodide, by methods known per se, e.g. G. Olah et al. *J. Org. Chem.* 1979, 44, 1247.

The 3-methoxypyridazin-4-amines of formula (XII) are obtained by coupling of 4-iodo-3-methoxypyridazines of formula (XIII), wherein $R^4$ and $R^5$ are as hereinabove-defined, with aryl or heteroarylamines of formula $R^2R^3NH$, wherein $R^2$ and $R^3$ are as hereinbefore defined. The reaction takes place in the presence of a catalytic amount of a palladium (II) salt, such as palladium acetate or bis(dibenzylideneacetone) palladium, and a catalytic amount of a phosphorus ligand such as 2,2'-bis(diphenylphosphino)-1,1'-binaphthyl, by methods known per se, e.g. J. P. Wolfe et al. *J. Org. Chem.* 1997, 62, 6066.

4-iodo-3-methoxypyridazines of formula (XIII), wherein $R^4$ and $R^5$ are as hereinabove-defined, are obtained by metallation of 6-methoxypyridazines of formula (XIV) with the lithium amide of a hindered secondary amine such as diisopropylamine, tert-butyl(1-isopropylpentyl)amine or 2,2,6,6-tetramethylpiperidine, and subsequent reaction with iodine. The reaction is preferably carried out in an inert solvent such as diethyl ether or tetrahydrofuran at a temperature of –78° C. under inert atmosphere.

6-Methoxypyridazines of formula (XIV), wherein $R^4$ and $R^5$ are as hereinabove-defined, may be obtained by condensation of 3-chloro-6-methoxypyridazine derivatives of formula (XV) with boronic acids of formula $R^5B(OH)_2$ wherein $R^5$ is as hereinabove defined, by methods known per se, e.g. I. Parrot et al., *Synthesis* 1999, 1163.

Alternatively, intermediate pyridazin-3(2H)-ones (II) wherein $R^4$ is H or CN may also be obtained as shown in Scheme 4.

Scheme 4

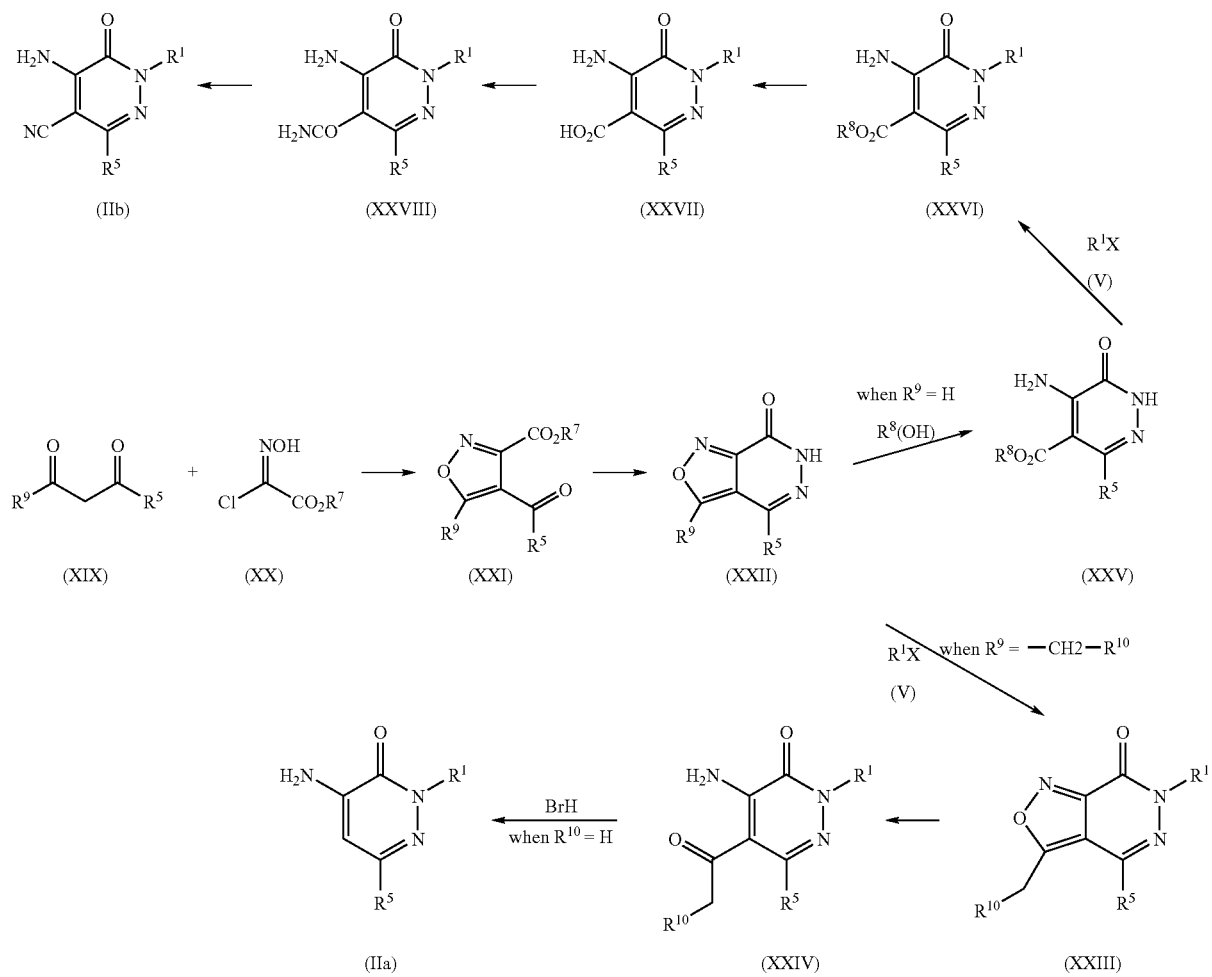

Reaction of 1,3-dicarbonylic compounds of general formula (XIX) wherein $R^5$ is as hereinabove defined, $R^9$ is either a hydrogen atom or a group —$CH_2$—$R^{10}$ wherein $R^{10}$ is an alkyl or aryl group, and 2-chloro-2-(hydroxyimino)acetate derivatives of formula (XX), wherein $R^7$ is a $C_1$ to $C_4$ alkyl group, following methods known per se, e.g. G. Renzi et al., *Gazz. Chim. Ital.* 1965, 95, 1478, gives isoxazole derivatives of formula (XXI).

Isoxazole derivatives of formula (XXI), wherein $R^5$, $R^7$ and $R^9$ are as hereinabove-defined, are condensed with hydrazine, by methods known per se, e.g. G. Renzi et al., *Gazz. Chim. Ital.* 1965, 95, 1478 and V. Dal Piaz et al. *Heterocycles* 1991, 32, 1173, to give isoxazolo[3,4-c]pyridazin-7(6H)-ones of formula (XXII) wherein $R^5$ is as hereinbefore defined.

Depending on the nature of the $R^9$ rest the isoxazolo[3,4-d]pyridazin-7(6H)-ones of formula (XXII) can be used to obtain pyridazin-3(2H)-one derivatives (II) wherein $R^4$ is H or CN.

Thus, when $R^9$ is a methyl rest the compounds of formula (XXII) are used to obtain compounds of formula (IIa) wherein $R^4$ is hydrogen.

In this synthetic path compounds (XXII), wherein $R^5$ and $R^9$ are as hereinabove-defined, are reacted with an alkylating agent of formula (V), wherein $R^1$ is as hereinbefore defined and X is a leaving group such as a chlorine or a bromine atom or a methanesulfonate, p-toluenesulfonate or a benzenesulfonate group, by methods known per se, e.g. V. Dal Piaz et al. *Drug Des. Discovery* 1996, 14, 53 or alternatively they are condensed with an alcohol of formula $R^1OH$ wherein $R^1$ is as hereinbefore described in the presence of triphenylphosphine and diethylazodicarboxylate by methods known per se, e. G. O. Mitsunobu et al. *J. Am. Chem. Soc.* 1972, 94, 679, to yield isoxazolo[3,4-d]pyridazin-7(6H)-ones of formula (XXIII) wherein $R^1$ and $R^5$ are as hereinbefore defined.

Isoxazolo[3,4-d]pyridazin-7(6H)-ones of formula (XXIII), wherein $R^1$, $R^5$ and $R^{10}$ are as hereinbefore defined, are hydrogenated to yield 5-acetyl-4-aminopyridazin-3(2H)-one derivatives (XXIV). The hydrogenation may be performed using for example hydrogen in the presence of a catalyst by methods known per se, e.g. V. Dal Piaz et al. *Heterocycles,* 1991, 32, 1173. Alternatively, the reaction may be accomplished by transfer hydrogenation using an organic hydrogen donor and a transfer agent, such as ammonium formate or hydrazine by methods known per se, e.g. V. Dal Piaz et al. *Heterocycles,* 1991, 32, 1173.

Treatment of 4-aminopyridazin-3(2H)-one derivatives (XXIV), wherein $R^1$, $R^5$ and $R^{10}$ are as hereinbefore defined, with hydrobromic acid at reflux, gives compounds (IIa), wherein $R^1$ and $R^5$ are as hereinbefore defined.

When $R^9$ is hydrogen the compounds of formula (XXII) are used to obtain compounds of formula (IIb) wherein $R^4$ is a cyano group.

In this synthetic path compounds (XXII) are reacted with alcohols of general formula $R^8OH$ wherein $R^8$ is an alkyl group, to give 5-amino-6-oxo-1,6-dihydropyridazine-4-carboxylates of formula (XXV), wherein $R^1$ and $R^8$ are as hereinabove-defined. The reaction is carried out in the presence of an organic base, preferably an amine base such as triethylamine or piperidine, at a temperature from room temperature to the boiling point of the alcohol.

Subsequent reaction of 5-amino-6-oxo-1,6-dihydropyridazine-4-carboxylates of formula (XXV), wherein $R^5$ and $R^8$ are as hereinabove-defined, with an alkylating agent of formula (V), wherein $R^1$ is hereinbefore defined and X is a leaving group such as a chlorine or a bromine atom or a methanesulfonate, p-toluenesulfonate or a benzenesulfonate group, by methods known per se, e.g. V. Dal Piaz et al. *Drug Des. Discovery* 1996, 14, 53, gives 5-amino-6-oxo-1,6-dihydropyridazine-4-carboxylates of formula (XXVI).

Hydrolysis of 5-amino-6-oxo-1,6-dihydropyridazine-4-carboxylates of formula (XXVI), wherein $R^1$, $R^5$ and $R^8$ are as hereinabove-defined, yields 5-amino-6-oxo-1,6-dihydropyridazine-carboxylic acids (XXVII), wherein $R^1$ and $R^5$ are as hereinbefore defined.

Activation of 5-amino-6-oxo-1,6-dihydropyridazine-4-carboxylic acids (XXVII), wherein $R^1$ and $R^5$ are as hereinabove-defined, with thionyl chloride, followed by quenching with aqueous ammonia, by methods known per se, e.g. V. Dal Piaz et al. *Eur. J. Med. Chem.* 1996, 31, 65, gives 5-amino-6-oxo-1,6-dihydropyridazine-4-carboxamides (XXVIII), wherein $R^1$ and $R^5$ are as hereinbefore defined.

Dehydration of 5-amino-6-oxo-1,6-dihydropyridazine-4-carboxamides (XXVIII) with a dehydrating agent such as phosphorus oxychloride, by methods known per se, e.g. V. Dal Piaz et al. *Eur. J. Med. Chem.* 1996, 31, 65, gives 5-amino-6-oxo-1,6-dihydropyridazine-4-carbonitriles (IIb), wherein $R^1$ and $R^5$ are as hereinbefore defined.

Intermediate pyridazin-3(2H)-ones (I) wherein $R^4$ is an optionally substituted thiazol group may be obtained as shown in Scheme 5.

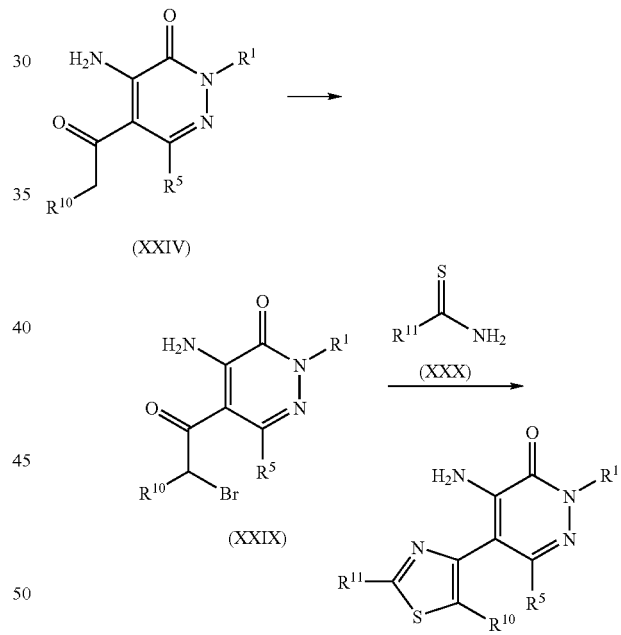

Scheme 5

Bromination of 5-acyl-4-aminopyridazin-3(2H)-one derivatives (XXIV), wherein $R^1$, $R^5$ and $R^{10}$ are as hereinabove-defined, gives bromo derivatives (XXIX). The reaction may be performed using for example bromine in a mixture of hydrobromic acid and acetic acid at a temperature from −20° C. to the boiling point of the solvent.

Reaction of bromoderivatives (XXIX) with a thioamide (XXX), where $R^{11}$ is an alkyl or aryl group following methods known per se, e.g. S. S. Sabnis et al. *Indian J Chem* 1963, 1, 447, gives 5-(thiazol-4-yl)-4-aminopyridazin-3(2H)-one derivatives (IIc).

According to another aspect of the present invention some intermediates of formula (II) and in particular those of formula (IId) may be obtained as shown in Scheme 6.

Scheme 6

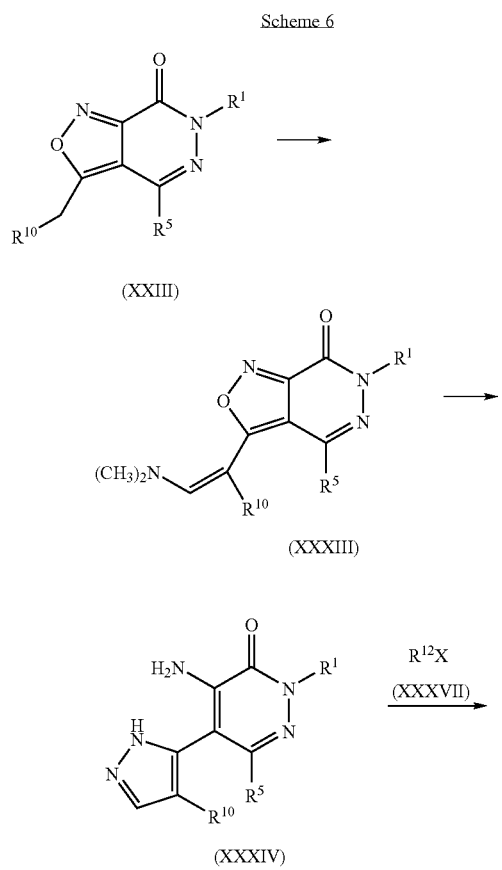

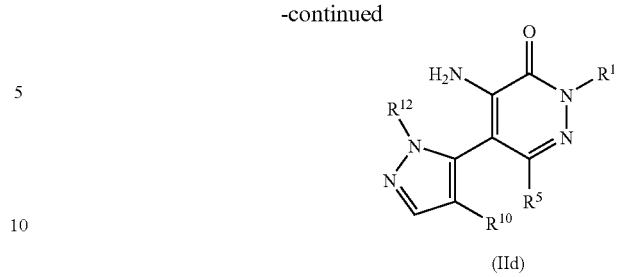

(IId)

Condensation of isoxazolo[3,4-d]pyridazin-7(6H)-ones of formula (XXIII), wherein $R^1$, $R^5$ and $R^{10}$ are as hereinabove-defined, with N,N-dimethylformamide dimethyl acetal following methods known per se, e.g. V. Dal Piaz et al. *J. Pharm. Sci.* 1991, 80, 341, gives 3-[(2-dimethylamino)vinyl]isoxazolo[3,4-d]-pyridazin-7(6H)-ones (XXXIII).

Reaction of 3-[(2-dimethylamino)vinyl]isoxazolo[3,4-d]-pyridazin-7(6H)-ones (XXXIII), wherein $R^1$, $R^5$ and $R^{10}$ are as hereinabove-defined, with hydrazine, following methods known per se, e.g. V. Dal Piaz et al. *J. Pharm. Sci.* 1991, 80, 341, yields 4-amino-5-(2H-pyrazol-3-yl)-2H-pyridazin-3-ones (XXXIV).

Reaction of 4-amino-5-(2H-pyrazol-3-yl)-2H-pyridazin-3-ones (XXXIV), wherein $R^1$, $R^5$ and $R^{10}$ are as hereinabove-defined, with an alkylating agent of formula (XXXVII), wherein $R^{12}$ is an alkyl or aryl group, by methods known per se, e.g. F. Effenberger et al. *J Org Chem* 1984, 49, 4687, gives 4-amino-5-(2H-pyrazol-3-yl-2H-pyridazin-3-ones (XXXV).

According to another aspect of the present invention some specific compounds of formula (I) and in particular those of formula (XXXIX), (XL), (XLI) and (XLII) may be obtained as shown in Scheme 7.

Scheme 7

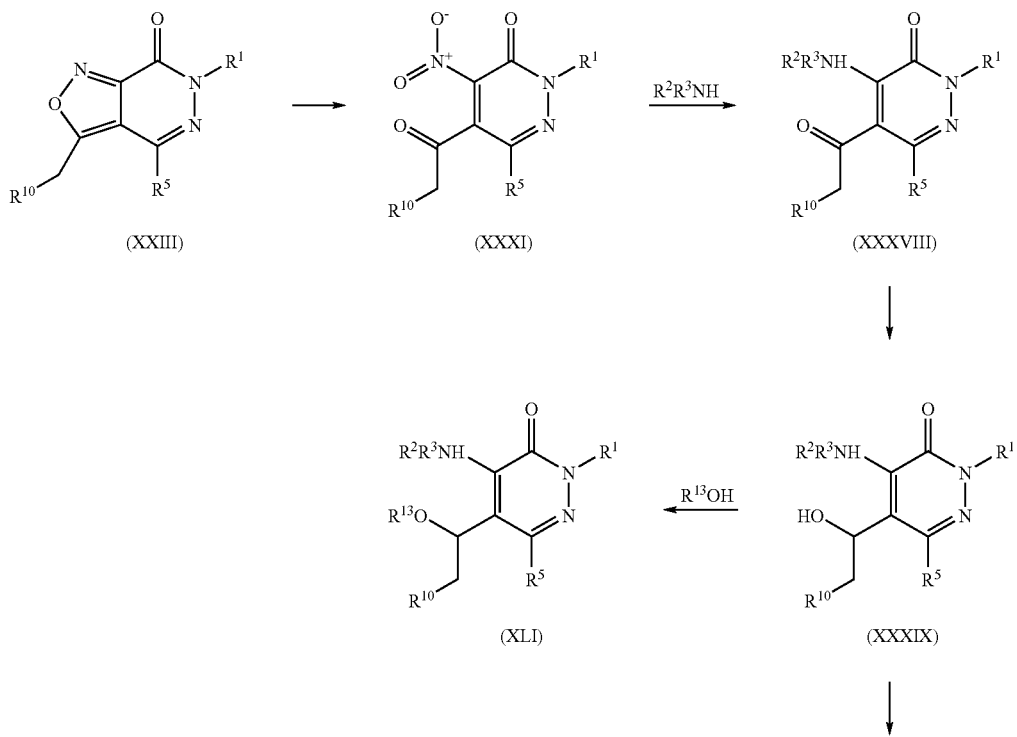

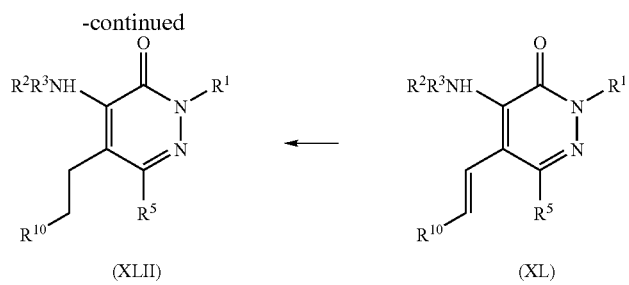

Oxidative cleavage of isoxazolo[3,4d]pyridazin-7(6H)-ones of formula (XXIII), wherein $R^1$, $R^5$ and $R^{10}$ are as hereinabove-defined, by methods known per se, e.g. V. Dal Piaz et al. Synthesis, 1988, 213-214, gives 5-acyl-4-nitro-3-oxo-2,3-dihydropyridazines of formula (XXXI).

Subsequent reaction of 5-acyl-4-nitro-3-oxo-2,3-dihydropyridazines of formula (XXXI), wherein $R^1$, $R^5$ and $R^{10}$ are as hereinabove-defined, with aryl or heteroarylamines of formula $R^2R^3NH$ wherein $R^2$ and $R^3$ are as hereinbefore defined gives 5-acyl-2H-pyridazin-3-ones (XXXVIII). The reaction is preferably carried out in a solvent such as ethanol at a temperature between room temperature to the boiling point of the solvent.

Reduction of 5-acyl-2H-pyridazin-3-ones of formula (XXXVIII), wherein $R^1$, $R^2$, $R^3$, $R^5$ and $R^{10}$ are as hereinabove-defined, by methods known per se, e.g. V. Dal Piaz et al. Heterocycles 1991, 32, 1173, gives compounds of formula (XXXIX).

Condensation of hydroxyalkyl derivatives of formula (XXXIX), wherein $R^1$, $R^2$, $R^3$, $R^5$ and $R^{10}$ are as hereinabove-defined, with an alcohol of formula $R^{13}OH$, wherein $R^{13}$ is alkyl or aryl, by methods known per se, e.g. V. Dal Piaz et al. *Eur. J. Med. Chem.* 1991, 32, 1173, gives compounds of formula (XLI).

Dehydration of hydroxyalkyl derivatives of formula (XXXIX), wherein $R^1$, $R^2$, $R^3$, $R^5$ and $R^{10}$ are as hereinabove-defined, by methods known per se, e.g. V. Dal Piaz et al. *Eur. J. Med. Chem.* 1991, 32, 1173, gives compounds of formula (XL).

Reduction of alkenyl derivatives of formula (XL), wherein $R^1$, $R^2$, $R^3$, $R^5$ and $R^{10}$ are as hereinabove-defined, by methods known per se, e.g. V. Dal Piaz et al. *Eur. J. Med. Chem.* 1991, 32, 1173, gives compounds of formula (XLII).

According to another aspect of the present invention some intermediates of formula (II) and in particular those of formula (IIe) may be obtained as shown in Scheme 8.

Scheme 8

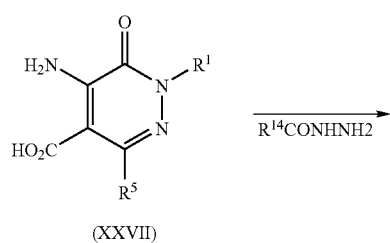

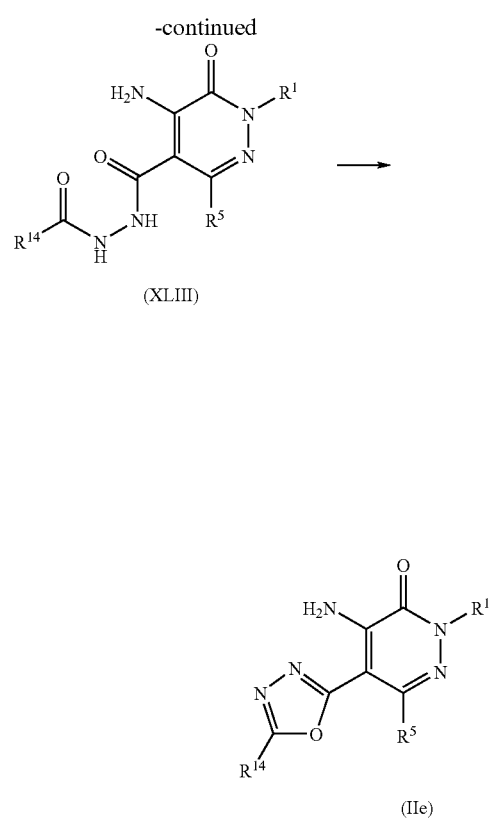

Activation of 5-amino-6-oxo-1,6-dihydropyridazine-4-carboxylic acids (XXVIII), wherein $R^1$ and $R^5$ are as hereinabove-defined, with thionyl chloride, followed by reaction with a hydrazide of formula $R^{14}CONHNH_2$, wherein $R^{14}$ is an alkyl or aryl group, by methods known per se, e.g. P. H. J. Carlsen et al., *J. Heterocycl. Chem.* 1994, 31, 805, gives compounds of formula (XLIII).

Dehydration of compounds of formula (XLIII), wherein $R^1$, $R^5$ and $R^{14}$ are as hereinabove-defined, by methods known per se, e.g. A. P. Grekov et al., *J. Gen. Chem. USSR* (*Engl Transl*) 1959, 29, 3054, gives 4-amino-5-([1,3,4]oxadiazol-2-yl)-2H-pyridazin-3-ones of formula (IIe)

According to another aspect of the present invention some intermediates of formula (II) and in particular those of formula (IIf) may be obtained as shown in Scheme 9.

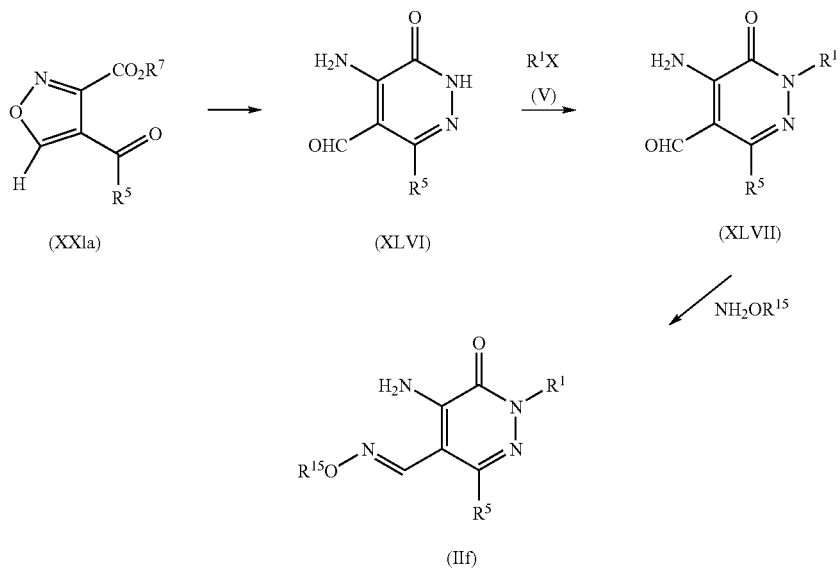

Reaction of isoxazoles of formula (XXIa), wherein $R^5$ and $R^7$ are as hereinabove-defined, with hydrazine, following methods known per se, e.g. V. Dal Piaz et al. *Heterocycles* 1991, 32, 1173, gives 5-amino-6-oxo-1,6-dihydropyridazine-4-carbaldehydes of formula (XLVI).

Subsequent reaction of 5-amino-6-oxo-1,6-dihydropyridazine-4-carbaldehydes of formula (XLVI), wherein $R^5$ is as hereinabove-defined, with an alkylating agent of formula (V), wherein $R^1$ is as hereinbefore defined and X is a leaving group such as a chlorine or a bromine atom or a methanesulfonate, p-toluenesulfonate or a benzenesulfonate group by methods known per se, e.g. V. Dal Piaz et al. *Drug Des. Discovery* 1996, 14, 53; or condensation with an alcohol of formula $R^1OH$ wherein $R^1$ is as hereinbefore described in the presence of triphenylphosphine and diethylazodicarboxylate by methods known per se, e. G. O. Mitsunobu et al. *J. Am. Chem. Soc.* 1972, 94, 679; gives 5-amino-6-oxo-1,6-dihydropyridazine-4-carbaldehydes of formula (XLVII).

Condensation of 5-amino-6-oxo-1,6-dihydropyridazine-4-carbaldehydes of formula (XVLII), wherein $R^1$ and $R^5$ are as hereinabove-defined, with O-alkylhydroxylamines of formula $NH_2OR^{15}$, wherein $R^{15}$ is an alkyl group, following methods known per se, e.g. D. Heyl et al.; *J. Am. Chem. Soc.* 1951, 73, 3430, gives 5-amino-6-oxo-1,6-dihydropyridazine-4-carbaldehyde O-alkyloximes of formula (IIf).

According to another aspect of the present invention some specific compounds of formula (II) and in particular those of formula (IIg) where $R^4$ is an acyloxymethyl group may be obtained as shown in Scheme 10.

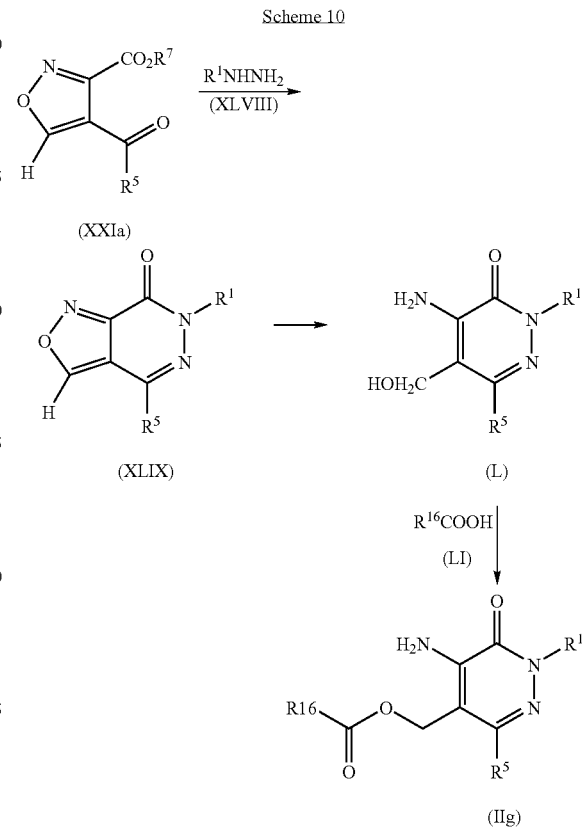

Reaction of isoxazoles of formula (XXIa) wherein $R^5$ and $R^7$ are as hereinbefore defined with a substituted hydrazine (XLVIII), wherein $R^1$ is as hereinbefore defined, following methods known per se, e.g. V. Dal Piaz et al. Heterocycles 1991, 32, 1173, gives isoxazolo[3,4-d]pyridazin-7-ones of formula (XLIX).

Subsequent reaction of isoxazolo[3,4-d]pyridazin-7-ones with an reducing agent such as sodium borohydride yields 4-amino-5-hydroxymethyl-2,6-dimethyl-2H-pyridazin-3-ones of formula (L). The reaction can be performed using, for instance, dimethylsulfoxide, tetrahydrofurane or methanol as solvent at a temperature between −20° C. and the boiling point of the solvent.

Condensation of 4-amino-5-hydroxymethyl-2,6-dimethyl-2H-pyridazin-3-one of formula (L) with carboxylic acids of formula (LI) following methods known per se, gives esters of formula (IIg).

When the defined groups $R^1$ to $R^5$ are susceptible to chemical reaction under the conditions of the hereinbefore described processes or are incompatible with said processes, conventional protecting groups may be used in accordance with standard practice, for example see T. W. Greene and P. G. M. Wuts in 'Protective Groups in Organic Chemistry', $3^{rd}$ Edition, John Wiley & Sons (1999). It may be that deprotection will form the last step in the synthesis of compounds of formula (I).

The compounds of formulae (IV), (VI), (IX), (X), (XI), (XV), (XVIII), (XIX), (XX), (XXVI), (XXX) and (XLVIII) are known compounds or can be prepared by analogy with known methods.

Pharmacological Activity

PDE4 Assay Procedure

Compounds to be tested were resuspended in DMSO at a stock concentration of 1 mM. The compounds were tested at different concentrations varying from 10 µM to 10 pM to calculate an $IC_{50}$. These dilutions were done in 96-well plates. In some cases, plates containing diluted compounds were frozen before being assayed. In these cases, the plates were thawed at room temperature and stirred for 15 minutes.

Ten microliters of the diluted compounds were poured into a "low binding" assay plate. Eighty microliters of reaction mixture containing 50 mM Tris pH 7.5, 8.3 mM $MgCl_2$, 1.7 mM EGTA, and 15 nM [3H]-cAMP were added to each well. The reaction was initiated by adding ten microliters of a solution containing PDE4. The plate was then incubated under stirring for 1 hour at room temperature. After incubation the reaction was stopped with 50 microlitres of SPA beads, and the reaction was allowed to incubate for another 20 minutes at room temperature before measuring radioactivity using standard instrumentation.

The reaction mixture was prepared by adding 90 ml of $H_2O$ to 10 ml of 10× assay buffer (500 mM Tris pH 7.5, 83 mM $mgCl_2$, 17 mM EGTA), and 40 microlitres 1 µCi/µL [3H]-cAMP. SPA beads solution was prepared by adding 500 mg to 28 ml $H_2O$ for a final concentration of 20 mg/ml beads and 18 mM zinc sulphate.

The results are shown in Table 1.

| No | HPDE4B or $IC_{50}$ PDE4 (nM) |
|---|---|
| 7 | 3,9 |
| 13 | 5.4 |
| 15 | 13 |
| 18 | 22 |
| 21 | 13 |
| 26 | 0,48 |
| 33 | 18 |
| 35 | 1,1 |
| 36 | 89 |
| 50 | 3,9 |

-continued

| No | HPDE4B or $IC_{50}$ PDE4 (nM) |
|---|---|
| 57 | 9,8 |
| 58 | 1,6 |

It can be seen from Table 1 that the compounds of formula (I) are potent inhibitors of phosphodiesterase 4 (PDE 4). Preferred pyridazin-3(2H)-one derivatives of the invention possess an $IC_{50}$ value for the inhibition of PDE4 (determined as defined above) of less than 100 nM, preferably less than 50 nM and most preferably less than 30 nM. The compounds are also capable of blocking the production of some pro-inflammatory cytokines such as, for example, TNFα.

Thus, they can be used in the treatment of allergic, inflammatory and immunological diseases, as well as those diseases or conditions where the blockade of pro-inflammatory cytokines or the selective inhibition of PDE 4 could be of benefit. These disease states include asthma, chronic obstructive pulmonary disease, allergic rhinitis, rheumatoid arthritis, osteoarthritis, osteoporosis, bone-formation disorders, glomerulonephritis, multiple sclerosis, ankylosing spondylitis, Graves ophtalmopathy, myasthenia gravis, diabetes insipidus, graft rejection, gastrointestinal disorders such as irritable bowel disease, ulcerative colitis or Crohn disease, septic shock, adult distress respiratory syndrome, and skin diseases such as atopic dermatitis, contact dermatitis, acute dermatomyositis and psoriasis. They can also be used as improvers of cerebrovascular function as well as in the treatment of other CNS related diseases such as dementia, Alzheimer's disease, depression, and as nootropic agents.

The compounds of the present invention are also of benefit when administered in combination with other drugs such as steroids and immunosuppressive agents, such as cyclosporin A, rapamycin or T-cell receptor blockers. In this case the administration of the compounds allows a reduction of the dosage of the other drugs, thus preventing the appearance of the undesired side effects associated with both steroids and immunosuppressants.

Like other PDE4 inhibitors (see references above) the compounds of the invention can also be used for blocking, after preventive and/or curative treatment, the erosive and ulcerogenic effects induced by a variety of etiological agents, such as antiinflammatory drugs (steroidal or non-steroidal antiinflammatory agents), stress, ammonia, ethanol and concentrated acids.

They can be used alone or in combination with antacids and/or antisecretory drugs in the preventive and/or curative treatment of gastrointestinal pathologies like drug-induced ulcers, peptic ulcers, *H. Pylori*-related ulcers, esophagitis and gastro-esophageal reflux disease.

They can also be used in the treatment of pathological situations where damage to the cells or tissues is produced through conditions like anoxia or the production of an excess of free radicals. Examples of such beneficial effects are the protection of cardiac tissue after coronary artery occlusion or the prolongation of cell and tissue viability when the compounds of the invention are added to preserving solutions intended for storage of transplant organs or fluids such as blood or sperm. They are also of benefit on tissue repair and wound healing.

Accordingly, the pyridazin-3(2H)-one derivatives of the invention and pharmaceutically acceptable salts thereof, and pharmaceutical compositions comprising such compound and/or salts thereof, may be used in a method of treatment or prevention of disorders of the human body susceptible to amelioration by inhibition of phosphodiesterase 4 which comprises administering to a patient requiring such treatment an effective amount of a pyridazin-3(2H)-one derivative of the invention.

The results of table I show that the compounds of formula (I) are potent inhibitors of phosphodiesterase 4 (PDE4) and are therefore useful in the treatment or prevention of pathological conditions, diseases and disorders known to be susceptible of amelioration by inhibition of PDE4, such as asthma, chronic obstructive pulmonary disease, rheumatoid arthritis, atopic dermatitis, psoriasis or irritable bowel disease.

The compounds of the present invention can also be used in combination with other drugs known to be effective in the treatment of these diseases. For example, in combination with steroids, immunosuppressive agents, T-cell receptor blockers and/or antiinflammatory drugs for simultaneous, separate or sequential use in the treatment of the human or animal body Accordingly, another embodiment of the invention is the use of the compounds of formula (I) in the manufacture of a medicament for treatment or prevention of pathological conditions, diseases and disorders known to be susceptible of amelioration by inhibition of PDE4, as well as a method for treating a subject afflicted with a pathological condition or disease susceptible to amelioration by inhibition of PDE4, which comprises administering to said subject an effective amount of a compound of formula (I).

The present invention also provides pharmaceutical compositions which comprise, as an active ingredient, at least a pyridazin-3(2H)-one derivative of formula (I) or a pharmaceutically acceptable salt thereof in association with a pharmaceutically acceptable excipient such as a carrier or diluent. The active ingredient may comprise 0.001% to 99% by weight, preferably 0.01% to 90% by weight, of the composition depending upon the nature of the formulation and whether further dilution is to be made prior to application. Preferably the compositions are made up in a form suitable for oral, topical, nasal, rectal, percutaneous or injectable administration.

The pharmaceutically acceptable excipients which are admixed with the active compound, or salts of such compound, to form the compositions of this invention are well-known per se and the actual excipients used depend inter alia on the intended method of administering the compositions.

Compositions for oral administration may take the form of tablets, retard tablets, sublingual tablets, capsules, inhalation aerosols, inhalation solutions, dry powder inhalation, or liquid preparations, such as mixtures, elixirs, syrups or suspensions, all containing the compound of the invention; such preparations may be made by methods well-known in the art.

The diluents which may be used in the preparation of the compositions include those liquid and solid diluents which are compatible with the active ingredient, together with colouring or flavouring agents, if desired. Tablets or capsules may conveniently contain between 2 and 500 mg of active ingredient or the equivalent amount of a salt thereof.

The liquid composition adapted for oral use may be in the form of solutions or suspensions. The solutions may be aqueous solutions of a soluble salt or other derivative of the active compound in association with, for example, sucrose to form a syrup. The suspensions may comprise an insoluble active compound of the invention or a pharmaceutically acceptable salt thereof in association with water, together with a suspending agent or flavouring agent.

Compositions for parenteral injection may be prepared from soluble salts, which may or may not be freeze-dried and which may be dissolved in pyrogen free aqueous media or other appropriate parenteral injection fluid.

Compositions for topical administration may take the form of ointments, creams or lotions, all containing the compound of the invention; such preparations may be made by methods well-known in the art.

Effective doses are normally in the range of 10-600 mg of active ingredient per day. Daily dosage may be administered in one or more treatments, preferably from 1 to 4 treatments, per day.

The present invention will be further illustrated by the following examples. The examples are given by way of illustration only and are not to be construed as a limiting.

The syntheses of the compounds of the invention and of the intermediates for use therein are illustrated by the following Examples (including Preparation Examples (Preparations 1 to 33)) which do not limit the scope of the invention in any way.

$^1$H Nuclear Magnetic Resonance Spectra were recorded on a Varian Gemini 300 spectrometer.

Low Resolution Mass Spectra (m/z) were recorded on a Micromass ZMD mass spectrometer using ESI ionization.

Melting points were recorded using a Perkin Elmer DSC-7 apparatus.

The chromatographic separations (standard method) were obtained using a Waters 2690 system equipped with a Symmetry C18 (2.1×10 mm, 3.5 mm) column. The mobile phase was formic acid (0.4 mL), ammonia (0.1 mL), methanol (500 mL) and acetonitrile (500 mL) (B) and formic acid (0.46 mL), ammonia (0.115 mL) and water (1000 mL) (A): initially from 0% to 95% of B in 18 min, and then 4 min. with 95% of B. The reequilibration time between two injections was 5 min. The flow rate was 0.4 mL/min. The injection volume was 5 microliter. Diode array chromatograms were collected at 210 nM.

The chromatographic separations (method B) were obtained using a Waters 2690 system equipped with a Symmetry C18 (2.1×10 mm, 3.5 mm) column. The mobile phase was formic acid (0.4 mL), ammonia (0.1 mL), methanol (500 mL) and acetonitrile (500 mL) (B) and formic acid (0.46 mL), ammonia (0.115 mL) and water (1000 mL) (A): initially from 0% to 95% of B in 26 min, and then 4 min. with 95% of B. The reequilibration time between two injections was 5 min. The flow rate was 0.4 mL/min. The injection volume was 5 microliter. Diode array chromatograms were collected at 210 nM.

PREPARATION EXAMPLES

Preparation 1

5-Acetyl-4-[(3-chlorophenyl)amino]-2-ethyl-6-phenylpyridazin-3(2H)-one

To a stirred solution of 5-acetyl-2-ethyl-4-nitro-6-phenylpyridazin-3(2H)-one (100 mg, 0.34 mmol) (Dal Piaz, V et al., *J. Med. Chem.* 1997, 40, 1417) in ethanol (2 mL), 3-chloroaniline (132 mg, 1.04 mmol) was added portionwise. The resulting mixture was stirred at room temperature for 30 min and the final product was collected by filtration and washed with ethanol and diethylether to yield the title compound (65% yield).

m.p. 189.0-190.6° C.

δ(DMSO-d6): 1.34 (t, 3H), 1.75 (s, 3H), 4.18 (q, 2H), 7.02 (m, 1H), 7.17 (m, 2H), 7.30 (m, 3H), 7.40 (m, 3H), 9.05 (s, 1H).

Preparation 2

5-Amino-1-ethyl-6-oxo-3-phenyl-1,6-dihydropyridazine-4-carbaldehyde

A mixture of 5-amino-6-oxo-3-phenyl-1,6-dihydropyridazine-4-carbaldehyde (Dal Piaz, V., Ciciani, G, Giovannoni, M. P., *Heterocycles,* 1991, 32, 1173-9) (258 mg, 1.2 mmol), ethyl bromide (294 mg, 2.7 mmol) and anhydrous potassium carbonate (240 mg, 2.4 mmol) in anhydrous DMF (5 mL) was stirred at 85° C. for 2 h. Cold water (25 mL) was added and the precipitate was collected by filtration to yield the title product (90%).

$\delta(CDCl_3)$: 1.43 (t, 3H), 4.27 (m, 2H), 6.95 (bs, 2H), 7.48 (m, 5H), 9.75 (s, 1H).

Preparation 3

5-Amino-1-ethyl-6-oxo-3-phenyl-1,6-dihydro-pyridazine-4-carbaldehyde O-methyloxime A suspension of the title compound of Preparation 2 (121 mg, 0.5 mmol) in MeOH (5 mL) was treated with a solution of methoxylamine hydrochloride (50 mg, 0.6 mmol) and Na2CO3 (64 mg, 0.6 mmol) in water (10 mL). Then, acetic acid (0.5 mL) was added and the mixture was refluxed for 24 h. Dilution with ice water afforded the reaction product that was isolated by filtration (98% yield).

$\delta(CDCl_3)$: 1.43 (t, 3H), 3.95 (s, 3H), 4.30 (m, 2H), 6.65 (bs, 1H), 7.45 (m, 5H), 7.90 (bs, 1H), 7.95 (s, 1H).

Preparation 4

5-Amino-6-oxo-3-phenyl-1,6-dihydro-pyridazine-4-carboxylic acid methyl ester

To a stirred solution of 4-phenyl-6H-isoxazolo[3,4-d]pyridazin-7-one (330 mg, 1.55 mmol) (V. Dal Piaz et al., Heterocycles, 1991, 32(6), 1173) in methanol (15 mL), piperidine was added (0.4 mL) and the mixture was refluxed for 1 h. Solvent was removed under reduced pressure and the residue was treated with water. The solid thus formed was isolated by filtration and dried to yield the title product (70% yield).

$\delta(CDCl_3)$: 3.49 (s, 3H), 7.02 (bs, 2H), 7.38 (s, 5H).

Preparation 5

5-Amino-1-ethyl-6-oxo-3-phenyl-1,6-dihydro-pyridazine-4-carboxylic acid methyl ester To a stirred solution of the title compound of Preparation 4 (245 mg, 1 mmol) in dry dimethylformamide (3 mL), potassium carbonate (276 mg, 2 mmol) and ethyl bromide (0.150 mL, 2 mmol) were added and the final mixture was stirred at 85° C. for 2 hours. Then it was poured onto ice water. The solid thus formed was isolated by filtration and dried to yield the title product (95%).

$\delta(CDCl_3)$: 1.41 (t, 3H), 3.48 (s, 3H), 4.25 (q, 2H), 7.00 (s, 2H), 7.38 (s, 5H).

Preparation 6

5-Amino-1-ethyl-6-oxo-3-phenyl-1,6-dihydro-pyridazine-4-carboxylic acid

A solution of the title product of Preparation 5 (464 mg, 1.7 mmol) in a mixture of 6N NaOH (7 mL) and EtOH (10 mL) was stirred at r.t. for 1.5 h. Then solvent was removed under reduced pressure and the residue thus obtained diluted with water and acidified with 6N HCl. The solid thus formed was filtered off and washed with water to yield the desired product (75%)

$\delta(CDCl_3)$: 1.42 (t, 3H), 4.22 (q, 2H), 7.40 (s, 5H).

Preparation 7

5-Amino-1-ethyl-6-oxo-3-phenyl-1,6-dihydro-pyridazine-4-carboxamide

A stirred mixture of the title compound of Preparation 6 (337 mg, 1.3 mmol) in thionyl chloride (5 mL) was heated at 60° C. for 1 hour. Then it was let to cool down and solvent was removed under reduced pressure. Ammonia (33% aqueous solution, 7 mL) was added at 0° C. and the mixture was stirred for 1 hour. The solid thus formed was filtered off, washed with water and dried to yield the desired product (60%).

$\delta(CDCl_3)$: 1.40 (t, 3H), 4.23 (q, 2H), 4.95 (s, 1H), 5.00 (s, 1H), 7.46 (s, 5H).

Preparation 8

5-Amino-1-ethyl-6-oxo-3-phenyl-1,6-dihydro-pyridazine-4-carbonitrile

The title product of Preparation 7 (186 mg, 0.72 mmol) was suspended in POCl3 (5 mL) and the mixture was stirred at 50-60° C. for 1 h. Then it was let to cool down and ice-water was carefully added. The solid thus formed was isolated by filtration and dried to yield the desired product (80%).

$\delta(CDCl_3)$: 1.43 (t, 3H), 4.26 (q, 2H), 7.40-7.78 (m, 5H).

Preparation 9

4-(4-Fluorobenzoyl)-isoxazole-3-carboxylic acid ethyl ester

To a cooled (0° C.) and stirred solution of sodium ethoxide (884 mg, 13 mmol), 3-(4 fluorophenyl)-3-oxopropionaldehyde (Baram, S. G.; Shkurko, O. P.; Mamaev, V. P. *Seriya Khimicheskikh Nauk* 1983, 2, 111-17) (2.16 g, 13 mmol) in anhydrous ethanol (20 mL) was added. Then a solution of ethyl chloro(hydroxymino)acetate (2 g, 13.3 mmol) in anhydrous ethanol (10 mL) was added dropwise during 1 hour. Solvent was removed under reduced pressure and the residue washed with cold water. Finally the title product was isolated by filtration and dried (58%).

$\delta(CDCl_3)$: 1.27 (t, 3H), 4.34 (q, 2H), 7.20 (m, 2H), 7.88 (m, 2H), 8.80 (s, 1H).

Preparation 10

4-(4-Fluorophenyl)-6H-isoxazolo[3,4-d]pyridazin-7-one

A mixture of the title compound of preparation 9 (0.526 g; 0.2 mmol), poliphosphoric acid (4 g), hydrazine hydrate (0.25 g, 5 mmol) and ethanol (4 mL) was stirred at 80° C. for 6 hours. Then it was let to cool down and ice-water was added. The precipitate was collected by filtration, washed with water and dried to yield the desired compound (67%).

$\delta(DMSO$-$d6)$: 7.37 (m, 2H), 7.92 (m, 2H), 10.29 (s, 1H), 12.81 (s, 1H).

Preparation 11

5-Amino-3-(4-fluorophenyl)-6-oxo-1,6-dihydro-pyridazine-4-carboxylic acid methyl ester Obtained as a solid (88%) from the title compound of Preparation 10 using the experimental procedure described in Preparation 4.

δ(CDCl$_3$): 3.52 (s, 3H), 7.04-7.46 (m, 4H).

Preparation 12

5-Amino-1-ethyl-3-(4-fluorophenyl)-6-oxo-1,6-dihydro-pyridazine-4-carboxylic acid methyl ester Obtained as a solid (96%) from the title compound of Preparation 11 using the experimental procedure described in Preparation 5.

δ(CDCl$_3$): 1.40 (t, 3H), 3.52 (s, 3H), 4.23 (q, 2H), 7.08 (m, 2H), 7.34 (m, 2H).

Preparation 13

5-Amino-1-ethyl-3-(4-fluorophenyl)-6-oxo-1,6-dihydro-pyridazine-4-carboxylic acid Obtained as a solid (67%) from the title compound of Preparation 12 using the experimental procedure described in Preparation 6.

δ(CDCl$_3$): 1.30 (t, 3H), 4.05 (q, 2H), 7.05-7.80 (m, 4H), 13.00 (s, 1H).

Preparation 14

5-Amino-1-ethyl-3-(4-fluorophenyl)-6-oxo-1,6-dihydro-pyridazine-4-carboxamide Obtained as a solid (79%) from the title compound of Preparation 13 using the experimental procedure described in Preparation 7.

δ(CDCl$_3$): 1.41 (t, 3H), 4.24 (q, 2H), 4.95 (s, 1H), 5.58 (s, 1H), 7.16 (m, 2H), 7.52 (m, 2H).

Preparation 15

5-Amino-1-ethyl-3-(4-fluorophenyl)-6-oxo-1,6-dihydro-pyridazine-4-carbonitrile Obtained as a solid (61%) from the title compound of Preparation 14 using the experimental procedure described in Preparation 8.

δ(CDCl$_3$): 1.42 (t, 3H), 4.26 (q, 2H), 7.18-7.85 (m, 4H).

Preparation 16

4-(3-Fluorobenzoyl)-isoxazole-3-carboxylic acid ethyl ester

The title compound was obtained as a solid (52% yield) starting from 3-(3-fluorophenyl)-3-oxo-propionaldehyde (Baram, S. G.; Shkurko, O. P.; Mamaev, V. P. Seriya Khimicheskikh Nauk 1983, 2, 111-17) and ethyl chloro(hydroxymino)acetate in the presence of sodium ethoxide, using the experimental procedure described in Preparation 9.

δ(CDCl$_3$): 1.28 (t, 3H), 4.35 (q, 2H), 7.30-7.70 (m, 4H), 8.83 (s, 1H).

Preparation 17

4-(3-Fluorophenyl)-6H-isoxazolo[3,4-d]pyridazin-7-one

Obtained as a solid (71%) from the title compound of Preparation 16 using the experimental procedure described in Preparation 10.

δ(CDCl$_3$): 7.20-7.60 (m, 4H), 9.35 (s, 1H), 9.98 (s, 1H).

Preparation 18

5-Amino-3-(3-fluorophenyl)-6-oxo-1,6-dihydro-pyridazine-4-carboxylic acid methyl ester Obtained as a solid (73%) from the title compound of Preparation 17 using the experimental procedure described in Preparation 4.

δ(CDCl$_3$): 3.51 (s, 3H), 6.90-7.60 (m, 4H).

Preparation 19

5-Amino-1-ethyl-3-(3-fluorophenyl)-6-oxo-1,6-dihydro-pyridazine-4-carboxylic acid methyl ester Obtained as a solid (95%) from the title compound of Preparation 18 using the experimental procedure described in Preparation 5.

δ(CDCl$_3$): 1.41 (t, 3H), 3.52 (s, 3H), 4.24 (q, 2H), 7.00-7.43 (m, 4H).

Preparation 20

5-Amino-1-ethyl-3-(3-fluorophenyl)-6-oxo-1,6-dihydro-pyridazine-4-carboxylic acid Obtained as a solid (73%) from the title compound of Preparation 19 using the experimental procedure described in Preparation 6.

δ(CDCl$_3$): 1.25 (t, 3H), 4.07 (q, 2H), 7.00-7.80 (m, 4H), 13.00 (s, 1H).

Preparation 21

5-Amino-1-ethyl-3-(3-fluorophenyl)-6-oxo-1,6-dihydro-pyridazine-4-carboxamide Obtained as a solid (60%) from the title compound of Preparation 20 using the experimental procedure described in Preparation 7.

δ(CDCl$_3$): 1.41 (t, 3H), 4.24 (q, 2H), 5.00 (s, 1H), 5.60 (s, 1H), 7.00-7.55 (m, 4H).

Preparation 22

5-Amino-1-ethyl-3-(3-fluorophenyl)-6-oxo-1,6-dihydro-pyridazine-4-carbonitrile Obtained as a solid (80%) from the title compound of Preparation 21 using the experimental procedure described in Preparation 8.

δ(CDCl$_3$): 1.43 (t, 3H), 4.26 (q, 2H), 7.10-7.55 (m, 4H).

Preparation 23

5-Acetyl-4-amino-2-ethyl-6-phenylpyridazin-3(2H)-one

A mixture of 6-ethyl-3-methyl-4-phenylisoxazolo[3,4-d]pyridazin-7(6H)-one (Dal Piaz, V et al., J. Med. Chem. 1997, 40, 1417) (2.0 g, 7.83 mmol) and 10% palladium on charcoal (400 mg) in ethanol (400 mL) was shaken under hydrogen at room temperature and 2 bar for 3 h. The catalyst was filtered off and the solvent was removed under reduced pressure to yield the title compound (98% yield).

m.p. 150.8-152.7° C.

δ(CDCl$_3$): 1.43 (t, 3H), 1.67 (bs, 2H), 1.78 (s, 3H), 4.26 (q, 2H), 7.45 (s, 5H).

Preparation 24

4-Amino-5-(2-bromoacetyl)-2-ethyl-6-phenyl-2H-pyridazin-3-one

To a solution of the title compound of Preparation 23 (205 mg, 0.8 mmoles) in anhydrous acetic acid (2.5 mL) in the presence of 47% HBr (0.4 mL), a solution of Br$_2$ (41 µL, 0.8 mmol) in anhydrous acetic acid (1.5 mL) was added dropwise. The mixture was stirred at 40° C. for 1 hour and then treated with ice water. The solid thus formed was collected by filtration and purified by recrystallization from ethanol to yield the title product (88%).

δ(CDCl$_3$): 1.43 (t,3H), 3.50 (s, 2H), 4.26 (q, 2H) 7.50 (s, 5H).

Preparation 25

4-Amino-2-ethyl-5-(2-methylthiazol-4-yl)-6-phenyl-2H-pyridazin-3-one

To a suspension of the title compound of Preparation 24 (219 mg, 0.65 mmol) in ethanol (5 mL), thioacetamide (50 mg, 0.65 mmol) was added and the mixture was refluxed for 1.5 hours to afford the desired product after treatment with ice and water and filtration (80% yield).

δ(CDCl$_3$): 1.43 (t, 3H), 2.75 (s, 3H), 4.30 (m, 2H), 6.17 (s, 1H), 6.60 (s, 2H), 7.42 (m, 5H).

Preparation 26

4-Amino-2-ethyl-6-phenyl-5-(2-phenylthiazol-4-yl)-2H-pyridazin-3-one

Obtained as a solid (80%) from the title compound of Preparation 24 using the experimental procedure described in Preparation 25.

δ(CDCl$_3$): 1.46 (t, 3H), 4.32 (q, 2H), 6.33 (s, 1H), 7.36 (s, 5H), 7.50 (m, 3H), 7.95 (m, 2H).

Preparation 27

3-[(2-Dimethylamino)vinyl]-6-ethyl-4-phenylisossazolo[3,4-d]-pyridazin-6(7H)-one A mixture of 3-methyl-6-ethyl-4-phenylisossazolo[3,4-d]-pyridazin-6(7H)-one (Dal Piaz, V et al., *J. Med. Chem.* 1997, 40, 1417) (0.3 g, 1.17 mmol) and N,N-dimethylformamide dimethyl acetal (4.5 mL) was stirred at 100° C. for 4 hours. After cooling the precipitate was collected by filtration, washed with cold ethanol and dried to yield the title compound (63%).

δ(CDCl$_3$): 1.40 (t, 3H), 2.80 (s, 6H), 4.20 (q, 2H), 7.50 (m, 7H).

Preparation 28

4-Amino-2-ethyl-6-phenyl-5-(2H-pyrazol-3-yl)-2H-pyridazin-3-one

A suspension of the title compound of Preparation 27 (150 mg, 0.5 mmol) in ethanol (3 mL) and hydrazine hydrate (0.75 mL, 24 mmol) was refluxed for 2 hours. After cooling, the precipitate was collected by filtration, washed with cold ethanol and dried (88%).

δ(CDCl$_3$): 1.40 (t, 3H), 4.30 (q, 2H), 5.80 (d, 1H), 7.20-7.40 (m, 6H), 7.60 (bs, 2H).

Preparation 29

4-Amino-2-ethyl-5-(2-methyl-2H-pyrazol-3-yl)-6-phenyl-2H-pyridazin-3-one

To a stirred solution of the title compound of Preparation 28 (197 mg, 0.70 mmol) in dry dimethylformamide (3 mL), potassium carbonate (193 mg, 1.4 mmol) and methyl iodide (87 µL, 1.4 mmol) were added and the final mixture was stirred at 85° C. for 3 hours. Then it was poured onto ice water. The solid thus formed was isolated by filtration and dried to yield the title product (57% yield).

δ(CDCl$_3$): 1.43 (t, 3H), 3.91 (s, 3H), 4.29 (q, 2H), 5.19 (d, 1H), 7.08 (d, 1H), 7.36 (s, 5H).

Preparation 30

5-Amino-1-ethyl-6-oxo-3-phenyl-1,6-dihydro-pyridazine-4-carboxylic acid N'-acetyl-hydrazide A stirred mixture of the title compound of Preparation 6 (337 mg, 1.3 mmol) in 5 mL of thionyl chloride was heated at 60° C. for 1 hour. Then it was let to cool down and solvent was removed under reduced pressure. The product thus formed was dissolved in anhydrous dioxane (8 mL) and acetic hydrazide (259 mg, 3.5 mmol) was added. The mixture was stirred at room temperature for 1.5 h. The reaction product was collected by filtration and dried (90% yield).

δ(DMSO): 1.35 (t, 3H), 1.97 (s, 3H), 4.15 (q, 2H), 7.17 (bs, 2H), 7.30-7.60 (m, 5H), 10.28 (s, 1H), 10.43 (s,1H).

Preparation 31

4-Amino-2-ethyl-5-(5-methyl-[1,3,4]oxadiazol-2-yl)-6-phenyl-2H-pyridazin-3-one A suspension of the title compound of Preparation 30 (220 mg, 0.7 mmol) was suspended in POCl3 (3.5 mL) and stirred at 60° C. for 5 h. Cautious treatment with ice and water and filtration yielded the desired product (57%).

δ(CDCl$_3$): 1.47 (t, 3H), 2.22 (s, 3H), 4.29 (q, 2H), 7.30-7.46 (m, 5H).

Preparation 32

2-Ethyl-6-phenyl-4,5-dihydro-2H-pyridazin-3-one

A mixture of χ-oxobenzenebutanoic acid (20.0 g, 0.112 mol), ethyl hydrazine oxalate (16.8 g, 0.112 mol), and sodium acetate (33.6 g, 0.247 mol) in 240 ml of ethanol was heated under reflux for 7 hours. Ethanol was removed and the residue was treated with water. The semisolid mass was extracted with dichloromethane. The organic layer was washed with water, dried over sodium sulfate anhydride and evaporated. The oil obtained (22.9 g) was purified by treatment with ethyl ether to yield the title compound (64% yield).

δ(CDCl₃): 1.25 (t, 3H), 2.60 (t, 2H), 2.90 (t, 2H), 3.90 (q, 2H), 7.40 (m, 3H), 7.75 (m, 2H).

Preparation 33

2-Ethyl-6-phenyl-2H-pyridazin-3-one

Bromine (13.17 g, 0.082 moles) was added dropwise to a solution of the title product of Preparation 32 (14.5 g, 0.072) in 280 ml of glacial acetic acid heated at 90° C. After addition, the solution was stirred at 90° C. for an additional hour. Acetic acid was removed and the residue was treated with NaOH 2N and extracted with methylene chloride. The organic layer washed with water and brine, dried over sodium sulfate anhydride and evaporated. The oil obtained solidified in the freezer to yield the title compound (98%).

LRMS: m/Z 201 (M+1)⁺.

δ(CDCl₃): 1.40 (t, 3H), 4.30 (q, 2H), 7.00 (d, 1H), 7.50 (m, 3H), 7.70 (d, 1H), 7.80 (m, 2H).

Preparation 34

4-Amino-2-ethyl-6-phenyl-2H-pyridazin-3-one

A mixture of the title product of Preparation 33 (7.0 g, 0.035 mmol) and hydrazine monohydrate (210 ml) was heated under reflux for 24 hours. An additional amount of hydrazine hydrate (200 ml) was added and the reflux maintained for 24 hours more. The solution was cooled at room temperature and diluted with water (400 mL). The suspension was filtered and the residue washed with water and dried in the vacuum oven to yield the title compound (85%).

LRMS: m/Z 216 (M+1)⁺.

δ(CDCl₃): 1.40 (t, 3H), 4.30 (q, 2H), 5.00 (s, 2H), 6.70 (s, 1H), 7.40 (m, 3H), 7.72 (m, 2H).

Preparation 35

2-Ethyl-6-pyridin-3-yl-2H-pyridazin-3-one

3-Acetylpyridine (4.55 ml, 0.042 mol) was added to a cold solution of glyoxylic acid (3.8 g, 0.042 mol) and potassium carbonate (11.3 g, 0.080 mol) in water (50 mL).

The mixture was stirred at room temperature for 2.5 hours and then cooled in ice. Acetic acid (17.5 ml, 0.290 mol) was added, followed by ethyl hydrazine oxalate (7.51 g, 0.050 mol). The solution was heated under reflux for 3 hours and cooled in ice. Potassium carbonate was added to pH 7 and the solution was extracted with dichloromethane. The organic layer was evaporated and the oil obtained purified by column chromatography (silica gel, hexane/ethyl acetate) to yield the title compound (49%).

δ(CDCl₃): 1.40 (t, 3H), 4.30 (q, 2H), 7.05 (m, 1H), 7.40 (m, 1H), 7.70 (m, 1H), 8.10 (m, 1H), 8.70 (d, 1H), 9.05 (s, 1H).

Preparation 36

4-Amino-2-ethyl-6-pyridin-3-yl-2H-pyridazin-3-one

Obtained as a solid (71%) from the title compound of Preparation 35 following the experimental procedure described in Preparation 34.

δ(CDCl₃): 1.40 (t, 3H), 4.30 (q, 2H), 5.10 (s, 2H), 6.70 (s, 1H), 7.40 (m, 1H), 8.10 (m, 1H), 8.70 (d, 1H), 9.05 (s, 1H).

Preparation 37

2-Methyl-6-pyridin-3-yl-2H-pyridazin-3-one

Obtained as a solid (36%) from 3-acetylpyridine, glyoxylic acid and methyl hydrazine using the experimental procedure described in Preparation 35.

LRMS: m/Z 188 (M+1)⁺.

δ(CDCl₃): 3.90 (s, 3H), 7.05 (m, 1H), 7.40 (m, 1H), 7.70 (m, 1H), 8.10 (m, 1H), 8.70 (d, 1H), 9.05 (s, 1H).

Preparation 38

4-Amino-2-methyl-6-pyridin-3-yl-2H-pyridazin-3-one

Obtained as a solid (53%) from the title compound of preparation 37 following the experimental procedure described in Preparation 34.

LRMS: m/Z 203 (M+1)⁺.

δ(CDCl₃): 3.90 (s, 3H), 5.10 (s, 2H), 7.70 (s, 1H), 7.30 (m, 1H), 8.10 (m, 1H), 8.60 (d, 1H), 9.00 (s, 1H).

Preparation 39

2-Ethyl-6-pyridin-4-yl-2H-pyridazin-3-one

Obtained as a solid (38%) from 4-acetylpyridine, glyoxylic acid and ethyl hydrazine oxalate using the experimental procedure described in Preparation 35.

LRMS: m/Z 202 (M+1)⁺.

δ(DMSO-d₆): 1.38 (t, 3H), 4.20 (q, 2H), 7.10 (m, 1H), 7.90 (m, 2H), 8.18 (m,1H), 8.70 (m, 2H).

Preparation 40

4-Amino-2-ethyl-6-pyridin-4-yl-2H-pyridazin-3-one

Obtained as a solid (74%) from the title compound of Preparation 39 following the experimental procedure described in Preparation 34.

LRMS: m/Z 217 (M+1)⁺.

δ(DMSO-d₆): 1.20 (t, 3H), 4.00 (q, 2H), 6.50 (s, 2H), 6.60 (s, 1H), 7.60 (m, 2H), 8.50 (m, 2H).

Preparation 41

6-(3-Chlorophenyl)-2H-pyridazin-3-one

A stirred mixture of glyoxylic acid (4.0 g, 0.054 moles) and 3-chloroacetophenone (25.06 g, 0.162 moles) was heated at 105° C. for 2 hours, then allowed to cool to 40° C. and water (60 ml) was added followed by conc. aq. NH₄OH to pH 8. The mixture was extracted with methylene chloride (3×25 ml) to recover the 3-chloroacetophenone. The ammoniacal solution was stirred with hydrazine monohydrate (2.70 g, 0.054 moles) and heated under reflux for 8 hours. The resultant solid was collected by filtration and washed with water to yield the title compound (49%).

LRMS: m/Z 207 (M+1)⁺.

δ(CDCl₃): 7.00 (m, 1H), 7.35 (m, 2H), 7.70 (m, 2H), 7.80 (s, 1H).

Preparation 42

6-(3-Chlorophenyl)-2-ethyl-2H-pyridazin-3-one

Under nitrogen atmosphere bromoethane (18.31 g, 0.168 mol) was added dropwise to a solution of 6-(3-chlorophenyl)-2H-pyridazin-3-one (4.96 g, 0.024 mol) and potassium carbonate (19.90 g, 0.144 mol) in N,N-dimethylformamide (100 ml). The mixture was stirred at room temperature for 4 hours and then water (150 ml) and ethyl acetate (300 ml) were added. The organic layer washed with water and brine, dried over sodium sulfate anhydride and evaporated. The oil obtained solidified in the vacuum oven to yield the title compound (96%).

δ(CDCl$_3$): 1.45 (t, 3H), 4.30 (q, 2H), 7.00 (d, 1H), 7.40 (m, 2H), 7.70 (m, 2H), 7.80 (s, 1H).

Preparation 43

4-Amino-6-(3-chlorophenyl)-2-ethyl-2H-pyridazin-3-one

Obtained as a solid (25%) from the title compound of Preparation 42 following the experimental procedure described in Preparation 34.

LRMS: m/Z 250 (M+1)$^+$.

δ(CDCl$_3$): 1.45 (t, 3H), 4.30 (q, 2H), 5.00 (s, 2H), 6.70 (s, 1H), 7.35 (m, 2H), 7.65 (m, 1H), 7.80 (s, 1H).

Preparation 44

6-(6-Methylpyridin-3-yl)-2H-pyridazin-3-one

Obtained as a solid (37%) from 3-acetyl-6-methylpyridine, glyoxylic acid and hydrazine monohydrate using the experimental procedure described in Preparation 35.

LRMS: m/Z 188 (M+1)$^+$.

δ(DMSO-d$_6$): 2.40 (s, 3H), 6.90 (d, 1H), 7.15 (m, 1H), 7.90 (m, 2H), 8.75 (s, 1H), 13.10 (s, 1H).

Preparation 45

2-Ethyl-6-(6-methylpyridin-3-yl)-2H-pyridazin-3-one

Obtained as a solid (57%) from the title compound of Preparation 44 following the experimental procedure described in Preparation 42.

LRMS: m/Z 216 (M+1)$^+$

δ(DMSO-d$_6$): 1.15 (t, 3H), 2.50(s, 3H), 4.10 (q, 2H), 7.05 (d, 1H), 7.40 (m, 1H), 8.05 (d, 1H), 8.10 (m, 1H), 9.00 (s, 1H).

Preparation 46

4-Amino-2-ethyl-6-(6-methylpyridin-3-yl)-2H-pyridazin-3-one

Obtained as a solid (54%) from the title compound of Preparation 45 following the experimental procedure described in Preparation 34.

LRMS: m/Z 231 (M+1)$^+$

δ(DMSO-d$_6$): 1.30 (t, 3H), 2.50 (s, 3H), 4.10 (q, 2H), 6.60 (bs, 2H), 6.70 (s, 1H), 7.30 (m, 1H), 8.00 (m, 1H), 8.80 (s, 1H).

Preparation 47

4-(4-Methoxy-benzoyl)-5-methyl-isoxazole-3-carboxylic acid ethyl ester

To an ice-cooled solution of sodium metal (0.73 g, 31.7 mmol) in absolute ethanol (67 mL) 1-(4-methoxyphenyl)-butane-1,3-dione (Popic, V. V. et al., Synthesis 1991 (3), 195) (5.5 g, 28.6 mmol) in 20 mL of ethanol was added dropwise, and the mixture was stirred at 0° C. for 15 min. A solution of ethyl chloro(hydroximino)acetate (4.34 g, 28.6 mmol) in absolute ethanol (12 mL) was added dropwise and the final mixture was stirred at 0° C. for 30 min and at room temperature overnight. Solvent was removed under educed pressure and the residue thus obtained was suspended in ethyl acetate, washed with 4% sodium bicarbonate solution, water and brine, dried and concentrated to yield a yellowish oil which was purified by column cromatography (n-Hex/EtOAc 9:1 to 1:1) to afford the title compound (63% yield) as a yellow oil.

δ(CDCl3): 1.18 (t, 3H), 2.58 (s, 3H), 3.90 (s, 3H), 4.20 (q, 2H), 6.95 (d, 2H), 7.80 (d, 2H).

Preparation 48

4-(4-Methoxy-phenyl)-3-methyl-6H-isoxazolo[3,4-d]pyridazin-7-one

Hydrazine monohydrate (1.51 g, 29.6 mmol) was added dropwise to a solution of the title compound of Preparation 47 (5.22 g, 18 mmol) in dry ethanol (38 mL) and the resulting mixture was stirred overnight. After cooling with an ice bath, a precipitate was formed which was collected by filtration and washed with diethyl ether to yield the title compound (91% yield) as a white solid.

δ(DMSO-d6): 2.54 (s, 3H), 3.84 (s, 3H), 7.09 (d, 2H), 7.56 (d, 2H).

LRMS (m/z): 258 (M+1)$^+$.

Preparation 49

6-Ethyl-4-(4-methoxyphenyl)-3-methyl-6H-isoxazolo[3,4-d]pyridazin-7-one

To a suspension of the title compound of Preparation 48 (3.4 g, 13.2 mmol) and anhydrous potassium carbonate (5.48 g, 39.7 mmol) in dry dimethylformamide (50 mL) ethyl bromide (4.3 g, 39.7 mmol) was added and the resulting mixture was stirred at r.t. overnight. Solvent was removed under reduced pressure and the residue thus obtained was diluted with water (250 mL), extracted with ethyl acetate, washed with water and brine, dried and concentrated to yield the title compound (79% yield) as a yellow solid.

δ(DMSO-d6): 1.30 (t, 3H), 2.57 (s, 3H), 3.84 (s, 3H), 4.13 (q, 2H), 7.10 (d, 2H), 7.60 (d, 2H).

LRMS (m/z): 286 (M+1)$^+$.

Preparation 50

5-Acetyl-4-amino-2-ethyl-6-(4-methoxy-phenyl)-2H-pyridazin-3-one

A mixture of the title compound of Preparation 49 (2.98 g, 10.4 mmol) and 10% palladium on charcoal (0.6 g) in ethanol (500 mL) was shaken under hydrogen at room temperature and 2 bar for 3 h. The catalyst was filtered off and the solvent was removed under reduced pressure to yield the title compound (84% yield).

δ(DMSO-d6): 1.29 (t, 3H), 1.75 (s, 3H), 3.81 (s, 3H), 4.10 (q, 2H), 7.03 (d, 2H), 7.35 (d, 2H).

Preparation 51

4-Amino-2-ethyl-6-(4-hydroxy-phenyl)-2H-pyridazin-3-one

A stirred solution of the title compound of Preparation 50 (0.96 g, 3.3 mmol) in 0.7 mL of HBr (48% in water) was heated at 130° C. overnight. The resulting solid was suspended in water (50 mL) and then basified with 4% aq. sodium bicarbonate solution until pH=8-9. The aqueous layer was extracted with ethyl acetate, dried over anhydrous sodium sulphate and the solvent was evaporated under reduced pressure to afford the title compound as a white solid (60% yield).

δ(DMSO-d6): 1.30 (t, 3H), 4.10 (q, 2H), 6.65 (s, 1H), 6.85 (d, 2H), 7.58 (d, 2H).

LRMS (m/z): 232 (M+1)$^+$.

Preparation 52

4-Amino-2-ethyl-6-(4-methoxy-phenyl)-2H-pyridazin-3-one

To a solution of the title compound of Preparation 51 (0.4 g, 1.73 mmol) in methyl-ethyl ketone (17.3 mL), potassium carbonate (0.48 g, 3.46 mmol) and dimethyl sulphate (0.12 g, 0.95 mmol) were added and the reaction mixture was stirred at r.t. for 1 h. The solvent was removed under reduced pressure and the residue purified by column chromatography (C-18 reverse phase Biotage☐ cartridge (water (0.1M ammonium acetate)/acetonitrile 95:5 to 5:95) to give the title compound as a solid (59% yield).

LRMS (m/z): 246 (M+1)$^+$.

Retention Time: 8.40 min.

Preparation 53

3-Methoxy-6-phenyl-pyridazine

A mixture of 3-chloro-6-methoxy-pyridazine (4.0 g, 27.7 mmol) and phenyl boronic acid (5.1 g, 41.6 mmol) in toluene (160 mL) was degassed and tetrakis(triphenylphosphine)palladium (960 mg, 0.83 mmol) and 2M sodium carbonate (29.3 mL, 58.7 mmol) were added. The mixture was heated to reflux under nitrogen for 6 h, then cooled and the organic phase washed with 2M NaOH (75 mL), dried over magnesium sulphate and solvent removed under reduced pressure to give a solid which was subjected to column chromatography (n-Hex/EtOAc 9:1 to 1:1) to afford the title compound (74% yield) as a white solid.

δ(CDCl3): 4.18 (s, 3H), 7.04 (d, 1H), 7.47 (m, 3H), 7.78 (d, 1H), 8.00 (dd, 2H).

Preparation 54

4-Iodo-3-methoxy-6-phenyl-pyridazine n-BuLi (2.5M in hexanes, 2.27 mL, 5.67 mmol) was added to cold (−50° C.) anhydrous THF (20 mL) under nitrogen. 2,2,6,6-Tetramethylpiperidine (0.957, 0.8 g, 5.67 mmol) was then added and the mixture stirred at −78° C. for 30 min. A solution of the title compound of Preparation 53 (0.5 g, 2.68 mmol) in THF (5 mL) was added dropwise and the mixture was stirred at −78° C. for 60 min. Then, iodine (1.51 g, 5.94 mmol) was added and the mixture was stirred at that temperature for 90 min and then warmed to r.t. The mixture was quenched with methanol and the residual iodine destroyed with sat. sodium thiosulphate (aq.). The mixture was concentrated in vacuo, partitioned between ethyl acetate and water and the organic layer washed with water, dried and evaporated to give an oil which was purified by column cromatography (n-Hex/EtOAc 4:1) to afford the title compound (87% yield) as an oil which crystallised.

δ(CDCl3): 4.22 (s, 3H), 7.47 (m, 3H), 7.96 (m, 2H), 8.29 (s, 1H).

Preparation 55

(3-Methoxy-6-phenylpyridazin-4-yl)phenylamine

A suspension of palladium(II) acetate (8 mg, 0.036 mmol), BINAP (23 mg, 0.036 mmol) in toluene (5 mL) under argon was added via canula to a mixture of the title compound of Preparation 54 (560 mg, 1.79 mmol), cesium carbonate (2.92 g, 8.95 mmol) and aniline (200 mg, 2.15 mmol) in 12 mL of dry toluene. The resulting mixture was heated at 120° C. under argon overnight. The mixture was cooled down to r.t., filtered through sintered glass and the solvent was removed under reduced pressure to obtain 760 mg of a brown oil which was purified by column cromatography (CH2Cl2/EtOAc 98:2 to 9:1) to afford the title compound (87% yield) as a yellow solid.

δ(CDCl3): 4.27 (s, 3H), 7.20-7.30 (m, 2H), 7.35 (s, 1H), 7.40-7.50 (m, 6H), 7.91 (dd, 2H).

LRMS (m/z): 278 (M+1)$^+$.

Preparation 56

6-Phenyl-4-phenylamino-2H-pyridazin-3-one

In a sealed tube, under argon, the title compound of Preparation 55 (200 mg, 0.72 mmol), NaI (433 mg, 2.89 mmol) and acetonitrile (3 mL) were placed. Trimethylchlorosilane (314 mg, 2.89 mmol) was then added dropwise and the mixture was refluxed for 2 hours. The reaction was quenched by the addition of water (50 mL) and the aqueous phase was extracted with ethyl acetate. The combined organic layers were washed with sat. sodium thiosulphate, brine and dried over sodium sulphate. Removal of the solvent under reduced pressure gave 180 mg of a crude which was purified by column cromatography (CH2Cl2/Et2O 9:1) to afford the title compound (38% yield) as a white solid.

δ(DMSO-d6): 7.18 (s, 1H), 7.25-7.60 (m, 8H), 7.78 (d, 2H), 8.80 (s, 1H).

LRMS (m/z): 264 (M+1)$^+$.

Preparation 57

5-Methyl-4-(4-methyl-benzoyl)-isoxazole-3-carboxylic acid ethyl ester

Obtained as a yellow oil (83%) from 1-p-tolyl-butane-1,3-dione (Popic, V. V. et al., Synthesis 1991 (3), 195) and ethyl chloro(hydroximino)acetate following the procedure described in Preparation 47.

δ(CDCl3): 1.10 (t, 3H), 2.42 (s, 3H), 2.58 (s, 3H), 4.18 (q, 2H), 7.30 (d, 2H), 7.70 (d, 2H).

Preparation 58

3-Methyl-4-p-tolyl-6H-isoxazolo[3,4-d]pyridazin-7-one

Obtained as a yellow solid (38%) from the title compound of Preparation 57 following the experimental procedure described in Preparation 48. The final product was recrystallised from acetone.

δ(CDCl3): 2.48 (s, 3H), 2.58 (s, 3H), 7.35 (d, 2H), 7.42 (d, 2H).

Preparation 59

6-Ethyl-3-methyl-4-p-tolyl-6H-isoxazolo[3,4-d]pyridazin-7-one

Obtained as a yellow solid (89%) from the title compound of Preparation 58 following the experimental procedure described in Preparation 49.

δ(CDCl3): 1.42 (t, 3H), 2.48 (s, 3H), 2.58 (s, 3H), 4.30 (q, 2H), 7.35 (d, 2H), 7.45 (d, 2H).

LRMS (m/z): 270 (M+1)$^+$.

Retention Time: 9.60 min.

Preparation 60

5-Acetyl-4-amino-2-ethyl-6-p-tolyl-2H-Pyridazin-3-one

Obtained as a yellow solid (91%) from the title compound of Preparation 59 following the experimental procedure described in Preparation 50.

δ(CDCl3): 1.42 (t, 3H), 1.80 (s, 3H), 2.42 (s, 3H), 4.28 (q, 2H), 7.30 (d, 2H), 7.38 (d, 2H).

LRMS (m/z): 272 (M+1)$^+$.

Retention Time: 9.27 min.

Preparation 61

4-Amino-2-ethyl-6-p-tolyl-2H-pyridazin-3-one

Obtained as a yellow solid (48%) from the title compound of Preparation 60 following the experimental procedure described in Preparation 51. The final product was recrystallised from methanol.

δ(DMSO-d6): 1.32 (t, 3H), 2.35 (s, 3H), 4.15 (q, 2H), 6.50 (s, 2H, NH2), 6.75 (s, 1H), 7.30 (d, 2H), 7.68 (d, 2H).

LRMS (m/z): 202 (M+1)$^+$.

Retention Time: 9.07 min.

Preparation 62

Sodium 3-oxo-1-(3-methylphenyl)-propen-1-olate

A solution of 1-m-tolylethanone (5.36 g, 0.04 mol) and ethyl formate (4.44 mL, 0.066 mol) in 20 mL of dry toluene was added dropwise to a suspension of sodium (0.92 g, 0.04 mol) in 20 mL of dry toluene at 0° C. The resulting mixture was stirred at rt overnight until the complete solution of sodium. The solid thus obtained was filtered and washed with dry ethanol to yield the title product (6.1 g, 83% yield).

δ(CDCl$_3$): 2.51 (s, 3H), 6.20 (s, 1H), 7.40-7.80 (m, 5H), 8.20 (s, 1H).

Preparation 63

4-(3-Methylbenzoyl)-isoxazole-3-carboxylic acid ethyl ester

The title compound was obtained as a solid (55% yield) starting from the title compound of Preparation 62 and ethyl chloro(hydroxymino)acetate in the presence of sodium ethoxide, using the experimental procedure described in Preparation 9.

δ(CDCl$_3$): 1.30 (t, 3H), 2.45 (s, 3H), 4.47 (q, 2H), 7.35-7.70 (m, 4H), 8.86 (s, 1H).

Preparation 64

4-(3-Methylphenyl)-6H-isoxazolo[3,4-d]pyridazin-7-one

Obtained as a solid (86%) from the title compound of Preparation 63 using the experimental procedure described in Preparation 10.

δ(CDCl$_3$): 2.45 (s, 3H), 7.30-7.80 (m, 4H), 9.10 (s, 1H), 9.80 (s, 1H).

Preparation 65

5-Amino-3-(3-methylphenyl)-6-oxo-1,6-dihydro-pyridazine-4-carboxylic acid methyl ester Obtained as a solid (82%) from the title compound of Preparation 64 using the experimental procedure described in Preparation 4.

δ(CDCl$_3$): 2.45 (s, 3H), 3.52 (s, 3H), 7.20-7.48 (m, 4H).

Preparation 66

5-Amino-1-ethyl-3-(3-methylphenyl)-6-oxo-1,6-dihydro-pyridazine-4-carboxylic acid methyl ester Obtained as a solid (87%) from the title compound of Preparation 65 using the experimental procedure described in Preparation 5.

δ(CDCl$_3$): 1.48 (t, 3H), 2.45 (s, 3H), 3.53 (s, 3H), 4.32 (q, 2H), 7.10-7.30 (m, 4H).

Preparation 67

5-Amino-1-ethyl-3-(3-methylphenyl)-6-oxo-1,6-dihydro-pyridazine-4-carboxylic acid Obtained as a solid (98%) from the title compound of Preparation 66 using the experimental procedure described in Preparation 6.

δ(CDCl$_3$): 1.42 (t, 3H), 2.48 (s, 3H), 4.37 (q, 2H), 7.12-7.48 (m, 4H).

Preparation 68

5-Amino-1-ethyl-3-(3-methylphenyl)-6-oxo-1,6-dihydro-pyridazine-4-carboxamide Obtained as a solid (75%) from the title compound of Preparation 67 using the experimental procedure described in Preparation 7.

δ(CDCl$_3$): 1.45 (t, 3H), 2.45 (s, 3H), 4.28 (q, 2H), 5.05 (s, 1H), 5.40 (s, 1H), 7.30-7.40 (m, 4H).

Preparation 69

5-Amino-1-ethyl-3-(3-methylphenyl)-6-oxo-1,6-dihydro-pyridazine-4-carbonitrile Obtained as a solid (71%) from the title compound of Preparation 68 using the experimental procedure described in Preparation 8.

δ(CDCl$_3$): 1.48 (t, 3H), 2.49 (s, 3H), 4.30 (q, 2H), 7.28-7.50 (m, 4H).

Preparation 70

5-Acetyl-2-ethyl-6-phenyl-4-(quinolin-5-ylamino) pyridazin-3(2H)-one

To a stirred solution of 80 mg (0.278 mmol) of 5-acetyl-2-ethyl-4-nitro-6-phenylpyridazin-3(2H)-one (Dal Piaz, V et al., *J. Med. Chem.* 1997, 40, 1417) in 4 ml of ethanol, 60 mg (0.417 mmol) of 5-aminoquinoline was added. The resulting mixture was stirred at room temperature for four hours and the final product was collected by filtration and washed with diethylether to yield the title compound (80 mg, 74.8% yield).
m.p. 219.9-221.1° C.
δ(DMSO-$d_6$): 1.31 (s, 3H), 1.38 (m, 3H), 4.22 (q, 2H), 7.24 (m, 2H) 7.34-7.38 (m, 4H), 7.55-7.63 (m, 2H), 7.86 (d, 1H), 8.42 (d, 1H), 8.92 (d, 1H), 9.19 (s, 1H).

Preparation 71

5-Methyl-4-(3-methylbenzoyl)-isoxazole-3-carboxylic acid ethyl ester

Obtained as a brown oil (98%) from 1-m-tolyl-butane-1,3-dione (Popic, V. V. et al., *Synthesis* 1991 (3), 195) and ethyl chloro(hydroximino)acetate following the procedure described in Preparation 47.
δ(CDCl$_3$): 1.10 (t, 3H), 2.42 (s, 3H), 2.58 (s, 3H), 4.18 (q, 2H), 7.30-7.45 (m, 2H), 7.50-7.60 (m, 2H).

Preparation 72

3-Methyl-4-m-tolyl-6H-isoxazolo[3,4-d]pyridazin-7-one

Obtained as a yellow solid (73%) from the title compound of Preparation 71 following the experimental procedure described in Preparation 48. The final product was recrystallised from acetone.
δ(CDCl$_3$): 2.48 (s, 3H), 2.58 (s, 3H), 7.25-7.42 (m, 4H), 10.05 (bs, NH).

Preparation 73

6-Ethyl-3-methyl-4-m-tolyl-6H-isoxazolo[3,4-d] pyridazin-7-one

Obtained as a yellow solid (85%) from the title compound of Preparation 72 following the experimental procedure described in Preparation 49.
δ(CDCl$_3$): 1.42 (t, 3H), 2.48 (s, 3H), 2.58 (s, 3H), 4.30 (q, 2H), 7.25-7.42 (m, 4H).
LRMS (m/z): 270 (M+1)$^+$.
Retention Time*: 9.63 min.

Preparation 74

5-Acetyl-4-amino-2-ethyl-6-m-tolyl-2H-pyridazin-3-one

Obtained as a yellow solid (91%) from the title compound of Preparation 73 following the experimental procedure described in Preparation 50.
* Chromatographic Method B
δ(CDCl$_3$): 1.42 (t, 3H), 1.80 (s, 3H), 2.42 (s, 3H), 4.25 (q, 2H), 7.25-7.42 (m, 4H).
LRMS (m/z): 272 (M+1)$^+$.
Retention Time*: 9.25 min.

Preparation 75

4-Amino-2-ethyl-6-m-tolyl-2H-pyridazin-3-one

Obtained as a yellow solid (28%) from the title compound of Preparation 74 following the experimental procedure described in Preparation 51.
δ(DMSO-$d_6$): 1.32 (t, 3H), 2.35 (s, 3H), 4.15 (q, 2H), 6.50 (s, 2H, NH2), 6.75 (s, 1H), 7.25-7.42 (m, 2H).

Preparation 76

4-(2-Ethyl-3-oxo-6-m-tolyl-2,3-dihydro-pyridazin-4-ylamino)-benzoic acid methyl ester Obtained as a solid (8%) from the title compound of Preparation 74 and 4-methoxycarbonylphenylboronic acid following the experimental procedure described in Example 5.
LRMS (m/z): 406 (M+1)$^+$.
Retention Time: 10.15 min.

Preparation 77

N-Methoxy-5,N-dimethyl-nicotinamide

A mixture of 5-methyl-nicotinic acid (1.8 g, 13.1 mmole) and SOCl$_2$ (10 mL) was heated to 75° C. for three hours. The remaining SOCl$_2$ was removed by vacuum distillation and the oily residue carefully redissolved in dichloromethane (16 mL). Then N,O-dimethylhydroxyl amine hydrochloride (1.4 g, 14.4 mmol) was added. The reaction mixture was purged with argon and triethylamine (5.11 mL, 36.7 mmol) was dropwise added at 0° C. It was stirred for 24 hours at room temperature. The mixture was diluted with dichloromethane, washed with NaOH 2N, brine, dried and concentrated to yield a brown oil which was purified by column chromatography (SiO$_2$, n-Hex/EtOAc 1:1 to EtOAc) to afford the title compound (1.7 g, 71% yield) as a brownish oil.
δ(CDCl3): 2.38 (s, 3H), 3.37 (s, 3H), 3.55 (s, 3H), 7.81 (bs, 1H), 8.50 (d, 1H), 8.74 (d, 1H).
LRMS (m/z): 181 (M+1)$^+$.
Retention Time: 4.82 min.

Preparation 78

1-(5-Methyl-pyridin-3-yl)-ethanone

To an ice-cooled suspension of the title compound of Preparation 77 (2.67 g, 14.8 mmole), methyl magnesium bromide (3M in diethyl ether, 9.86 mL) was dropwise added under argon. After the addition was completed, the reaction mixture was stirred at 0° C. for one hour and the temperature was then allowed to rise to room temperature and stirred for five additional hours. After this period of time, the reaction was poured into ice, brine was added and the aqueous phase extracted with EtOAc, dried and concentrated to afford a yellowish oil (1.81 g, 91%) which was used in the next step without further purification.
δ(CDCl3): 2.40 (s, 3H), 2.65 (s, 3H), 8.05 (bs, 1H), 8.62 (d, 1H), 8.98 (d, 1H).
LRMS (m/z): 136 (M+1)$^+$.
Retention Time: 4.77 min.

Preparation 79

6-(5-Methyl-pyridin-3-yl)-2H-pyridazin-3-one

Potassium carbonate (1.97 g, 14.26 mmol) was portionwise added to a cold solution of glyoxylic acid (0.548 g, 7.4 mmol) in water (10 mL) and the title compound from Preparation 78 (1 g, 7.4 mmole) was slowly incorporated. The mixture was stirred at room temperature for 2.5 hours and then cooled in ice. Acetic acid (3 ml, 51.8 mmol) was added, followed by hydrazine monohydrate (0.43 mL, 8.9 mmol). The solution was heated under reflux for 2 hours and cooled in ice. The pH was adjusted to 7 by the addition of saturated aq. sodium bicarbonate and the solid obtained filtered, washed with cold water, diethyl ether and dried under vacuum to yield a orange solid (0.69 g, 50%) which was used in the next step without further purification.

$\delta$(DMSO-d6): 2.40 (s, 3H), 7.05 (d, 1H), 8.10 (d, 2H), 8.50 (bs, 1H), 8.90 (d, 1H).

LRMS (m/z): 188 (M+1)$^+$.

Retention Time: 4.57 min.

Preparation 80

2-Ethyl-6-(5-methyl-pyridin-3-yl)-2H-pyridazin-3-one

Obtained as a brown oil (85%) from the title compound of Preparation 79 following the experimental procedure described in Preparation 42.

LRMS (m/z): 216 (M+1)$^+$.

Retention Time: 6.25 min.

Preparation 81

4-Amino-2-ethyl-6-(5-methyl-pyridin-3-yl)-2H-pyridazin-3-one

Obtained as a brown oil (50%) from the title compound of Preparation 80 following the experimental procedure described in Preparation 34 but extracting the aqueous phase with EtOAc.

$\delta$(CDCl3): 1.42 (t, 3H), 2.40 (s, 3H), 4.25 (q, 2H), 6.70 (s, 1H), 7.90 (bs, 1H), 8.45 (s, 1H), 8.78 (s, 1H).

LRMS (m/z): 231 (M+1)$^+$.

Retention Time: 5.49 min.

Preparation 82

6-Ethyl-4-phenyl-isoxazolo[3,4-d]pyridazin-7(6H)-one

A mixture of ethylbenzoylisoxazole-3-carboxylate (G. Renzi, V. Dal Piaz et al. *Gazz. Chim. Ital.*, 1968, 98, 656) (0.25 g, 1.02 mmol) and polyphosphoric acid (2.5 g) was gently warmed at 50° C. until the solution became clear. Ethylhydrazine oxalate (0.5 g, 3.33 mmol) was added and the mixture was warmed at 90° C. for 5 hours. After cooling, ice-cold water was added and the precipitate was collected by filtration. The final product was purified by recrystallization from ethanol (0.24 g, 93% yield)

m.p.: 173-174° C.

$\delta$(CDCl3): 1.55 (t, 3H), 4.20 (q, 2H), 7.60 (m, 3H), 7.80 (m, 2H), 9.30 (s, 1H).

Preparation 83

2-Ethyl-4-amino-5-hydroxymethyl-6-phenylpyridazin-3(2H)-one

A solution of the title product of Preparation 82 (0.15 g, 0.63 mmol) in anhydrous DMSO (3 ml) was treated portionwise under stirring with NaBH$_4$ (0.28 g, 7.4 mmol). The mixture was stirred at room temperature for an additional hour. After dilution with ice-cold water the precipitate was collected by filtration. Additional amounts of the reaction product were obtained by exhaustive extraction of the solution, saturated with NH4Cl, with ethyl acetate. The combined solids were recrystallized from ethanol to yield the title product (0.12 g, 78% overall yield)

m.p.: 169-172° C.

$\delta$(DMSO-d$_6$): 1.25 (t, 3H), 4.10 (q, 2H), 4.20 (d, 2H), 5.00 (m, 1H), 6.30 (s, 2H), 7.40-7.50 (m, 5H).

Preparation 84

2-Ethyl-4-amino-5-acetyloxymethyl-6-phenylpyridazin-3(2H)-one

The title product of Preparation 83 (0.15 g, 0.61 mmol) was suspended in polyphosphoric acid (1 g) and treated with anhydrous acetic acid (2 ml). The mixture was warmed at 60° C. for 4 hours. After dilution with ice-cold water the mixture was neutralized under stirring and cooling with 6N NaOH and the precipitate was collected by filtration. Additional amount of the reaction product was obtained by exhaustive extraction of the solution with ethyl acetate. The final product was purified by column chromatography (SiO$_2$, ethyl acetate) (0.16 g, 90% overall yield).

m.p.: 112-115° C.

$\delta$(CDCl$_3$): 1.45 (t, 3H), 2.10 (s, 3H), 4.30 (q, 2H), 4.95 (s, 2H), 6.00 (s, 2H), 7.50 (m, 5H).

Preparation 85

4-Amino-5-butiryloxymethyl-2-ethyl-6-phenylpyridazin-3(2H)-one

To a mixture of polyphosphoric acid (1 g) and butyric acid (0.027 ml, 0.305 mmol) warmed at 60° C., the title compound of Preparation 83 (0.15 g, 0.61 mmol) was added portionwise under stirring and the suspension was warmed for 24 hours at the same temperature. After dilution with ice-cold water the mixture was neutralized under stirring and cooling with 6N NaOH and extracted with CH$_2$Cl$_2$. The solvent was removed under reduced pressure and the residue was purified by column chromatography (SiO$_2$, cyclohexane/ethyl acetate 1:3) (0.049 g, 22% yield).

m.p.: 107-110° C.

$\delta$(CDCl$_3$): 0.99 (t, 3H), 1.29-1.40 (m, 3H), 1.68-1.80 (m, 2H), 2.38 (t, 2H), 4.29 (q, 2H), 4.96 (s, 2H), 5.92 (bs, 2H), 7.40-7.65 (m, 5H).

Preparation 86

1-(6-Methyl-pyridin-3-yl)-ethanone

5-Ethyl-2-methyl-pyridine (40 g, 0.33 mol) was placed in a three-necked flask immersed in an ice bath and equipped with an efficient mechanical stirrer, a thermometer and a dropping funnel. Sulfuric acid (14.9 ml, 0.26 mol) was added with vigorous stirring. Then acetic acid (47.5 ml), acetic anhydride (46.3 ml) and finally CrO$_3$ (44 g, 0.44 mol) were added in small portions, at a rate to maintain the temperature of the reaction mixture between 20-30° C. Stirring was continued for 24 hours. Then 200 ml of water and Na$_2$CO$_3$ were added slowly, until the brown color of chromic acid was gone, and the product was extracted with ethyl acetate (3×200 ml). Combined organic layers were washed with water and brine and dried over magnesium sulfate and solvent was removed. The residue was distilled under reduced pressure (110° C., 19 mbar) to give 12.85 g of the desired product.

Preparation 87

4-Amino-2-ethyl-5-[2-(4-methoxyphenyl)-1,3-thiazol-4-yl]-6-phenylpyridazin-3(2H)-one To a suspension of the title compound of Preparation 24 (600 mg, 1.78 mmol) in ethanol (30 mL), 4-methoxythiobenzamide (298 mg, 1.78 mmol) was added and the mixture was refluxed for 1.5 hours to afford the desired product after treatment with ice and water and filtration (92% yield).

$\delta(CDCl_3)$: 1.43 (t, 3H), 3.85 (s, 3H), 4.30 (q, 2H), 6.22 (s, 1H), 6.98 (d, 2H), 7.38 (m, 5H), 7.83 (d, 2H).

Preparation 88

4-Amino-2-ethyl-6-phenyl-5-(2-pyridinyl-4-yl-1,3-thiazol-4-yl)pyridazin-3(2H)-one To a suspension of the title compound of Preparation 24 (600 mg, 1.78 mmol) in ethanol (25 mL), isothionicotinamide (247 mg, 1.78 mmol) was added and the mixture was refluxed for 23 hours to afford the desired product after treatment with ice and water and filtration (58% yield).

$\delta(DMSO\text{-}d_6)$: 1.38 (t, 3H), 4.20 (q, 2H), 6.60 (bs, 2H), 7.25 (m, 5H), 7.40 (s, 1H), 8.00 (d, 2H), 8.80 (d, 2H).

Preparation 89

4-Amino-5-[2-(4-chlorophenyl)-1,3-thiazol-4-yl]-2-ethyl-6-phenylpyridazin-3(2H)-one To a suspension of the title compound of Preparation 24 (600 mg, 1.78 mmol) in ethanol (30 ml), 4-chlorothiobenzamide (306 mg, 1.78 mmol) was added and the mixture was refluxed for 2.5 hours to afford the desired product after treatment with ice and water and filtration (95.5% yield).

$\delta(CDCl_3)$: 1.43 (t, 3H), 4.30 (q, 2H), 6.18 (s, 1H), 6.60 (bs, 2H), 7.38 (m, 5H), 7.40 (d, 2H), 7.82 (d, 2H).

Preparation 90

Ethyl 4-(5-amino-1-ethyl-6-oxo-3-phenyl-1,6-dihydropyridazin-4-yl)-1,3-thiazole-2-carboxylate To a solution of the title compound of Preparation 24 (700 mg, 2.08 mmol) in DMF (30 mL), ethyl thiooxamate (305 mg, 2.29 mmol) was added and the mixture was heated to 50° C. for 23 hours. Then the solution was extracted with ethyl acetate and the organic layer was evaporated. The orange oil thus obtained was purified by column chromatography (silica gel, hexane/ethyl acetate 8:2) to yield the title compound (13%).

$\delta(CDCl_3)$: 1.42 (m, 6H), 4.30 (q, 2H), 4.50 (q, 2H), 6.58 (s, 1H), 6.65 (bs, 2H), 7.35 (m, 5H).

EXAMPLES

Example 1

4-[(3-Chlorophenyl)amino]-2-ethyl-5-(1-hydroxyethyl)-6-phenylpyridazin-3(2H)-one To a suspension of the title compound of Preparation 1 (70 mg, 0.19 mmoles) in methanol (2 mL) NaBH4 (38 mg, 1 mmole) was added portionwise at 0-5° C. under stirring for 15 min. After evaporation of the solvent, ice water was added and the product filtered off (85% yield).

LRMS: m/Z 370 (M+1)$^+$.

Retention Time: 9.4 min.

Example 2

4-[(3-Chlorophenyl)amino]-2-ethyl-5-(1-methoxyethyl)-6-phenylpyridazin-3(2H)-one To a solution of the title product of example 1 (111 mg, 0.3 mmol mmol) in methanol (5 mL), PPA (600 mg) was added and the mixture was stirred in a sealed tube at 120° C. for 10 h. Then it was let to cool down and was diluted with water. The final product was isolated by filtration (96% yield).

LRMS: m/Z 384 (M+1)$^+$.

Retention Time: 10.2 min.

Example 3

4-[(3-Chlorophenyl)amino]-2-ethyl-6-phenyl-5-vinylpyridazin-3(2H)-one

To a solution of the title compound of example 1 (185 mg, 0.5 mmol) in toluene (8 mL), $H_2SO_4$ adsorbed on silica gel (Chavetz et al., Synthetic Communications, 24, 2325, 1884) (400 mg) was added portionwise during 4 h at 80° C. Then silica gel was filtered off and the residue was thoroughly washed with acetone. Solvent was removed under reduced pressure and the residue was treated with ice water. The final product precipitated and was isolated by filtration (63% yield).

LRMS: m/Z 351 (M+1)$^+$.

Retention Time: 10.5 min.

Example 4

4-Anilino-2,5-diethyl-6-phenylpyridazin-3(2H)-one

A mixture of the title compound of example 3 (67 mg, 0.19 mmol) and 10% palladium on charcoal (50 mg) in ethanol (10 mL) was shaken under hydrogen at room temperature and 4 bar for 2 h. The catalyst was filtered off and the solvent was removed under reduced pressure to yield the title compound (71% yield).

LRMS: m/Z 319 (M+1)$^+$.

Retention Time: 10.0 min.

Example 5

5-[(3-Chlorophenyl)amino]-1-ethyl-6-oxo-3-phenyl-1,6-dihydropyridazine-4-carbaldehyde O-methyloxime A mixture of the title compound of Preparation 3 (50 mg, 0.18 mmol), 3-chlorophenylboronic acid (56 mg, 0.36 mmol), anhydrous cupric acetate (49 mg, 0.27 mmol), triethylamine (50 μL, 0.36 mmol) and activated molecular sieves (xxxxx g, 4 Å) in dry dichloromethane (6 mL) was stirred under air exposure at room temperature for 4 h. The reaction was filtered and the solvent removed under reduced pressure. The final product was purified by column chromatography (43% yield).

LRMS: m/Z 382 (M+1)$^+$.

Retention Time: 10.5 min.

Examples 6-9

5-[(3-Chlorophenyl)amino]-1-ethyl-6-oxo-3-phenyl-1,6-dihydropyridazine-4-carbonitrile 1-Ethyl-5-{[4-(hydroxymethyl)phenyl]amino}-6-oxo-3-phenyl-1,6-dihydropyridazine-4-carbonitrile 1-Ethyl-6-oxo-3-phenyl-5-[(3,4,5-trifluorophenyl)amino]-1,6-dihydropyridazine-4-carbonitrile 5-[(4-Cyanophenyl)amino]-1-ethyl-6-oxo-3-phenyl-1,6-dihydropyridazine-4-carbonitrile The title compounds were synthesized from the title compound of Preparation 8 and the corresponding boronic acid following the procedure of Example 5. The ESI/MS data and HPLC retention times are summarized in Table 1.

TABLE 1

| EXAMPLE | ESI/MS m/e (M + H)$^+$ | Retention Time (min) |
|---|---|---|
| 6 | 351 | 9.4 |
| 7 | 347 | 8.2 |
| 8 | 371 | 10.1 |
| 9 | 342 | 9.5 |

Examples 10-12

1-Ethyl-3-(4-fluorophenyl)-5-{[4-(hydroxymethyl)phenyl]amino}-6-oxo-1,6-dihydropyridazine-4-carbonitrile 5-[(4-Cyanophenyl)amino]-1-ethyl-3-(4-fluorophenyl)-6-oxo-1,6-dihydropyridazine-4-carbonitrile 1-Ethyl-3-(4-fluorophenyl)-6-oxo-5-[(3,4,5-trifluorophenyl)amino]-1,6-dihydropyridazine-4-carbonitrile The title compounds were synthesized from the title compound of Preparation 15 and the corresponding boronic acid following the procedure of Example 5. The ESI/MS data and HPLC retention times are summarized in Table 2.

TABLE 2

| EXAMPLE | ESI/MS m/e (M + H)$^+$ | Retention Time (min) |
|---|---|---|
| 10 | 365 | 8.4 |
| 11 | 360 | 9.6 |
| 12 | 389 | 9.9 |

Example 13

1-Ethyl-3-(4-fluorophenyl)-6-oxo-5-(pyridin-3-ylamino)-1,6-dihydropyridazine-4-carbonitrile A mixture of the title compound of Preparation 15 (300 mg, 1.16 mmol), 3-bromopyridine (0.134 mL, 1.39 mmol), potassium carbonate (320 mg, 2.32 mmol), anhydrous copper(I) iodide (22 mg, 0.12 mmol) and N,N'-dimethylethylenediamine (25 μL, 0.23 mmol) in dry dioxane (1.2 mL) was refluxed under argon for 24 h. Then solvent was removed under reduced pressure and the residue was partitioned between water and dichloromethane. The organic layer washed with water and brine and solvent was removed under reduced pressure to yield a crude product that was purified by column chromatography (12% yield).

LRMS: m/Z 336 (M+1)$^+$.

δ(CDCl$_3$): 1.40 (t, 3H), 4.28 (q, 2H), 7.15 (m, 2H), 7.43 (m, 1H), 7.65 (m, 3H), 8.40 (s, 1H), 8.65 (bs, 2H).

Examples 14-16

1-Ethyl-3-(3-fluorophenyl)-5-{[4-(hydroxymethyl)phenyl]amino}-6-oxo-1,6-dihydropyridazine-4-carbonitrile 5-[(4-Cyanophenyl)amino]-1-ethyl-3-(3-fluorophenyl)-6-oxo-1,6-dihydropyridazine-4-carbonitrile 1-Ethyl-3-(3-fluorophenyl)-6-oxo-5-[(3,4,5-trifluorophenyl)amino]-1,6-dihydropyridazine-4-carbonitrile The title compounds were synthesized from the title compound of Preparation 22 and the corresponding boronic acid following the procedure of Example 5. The ESI/MS data and HPLC retention times are summarized in Table 3.

TABLE 3

| EXAMPLE | ESI/MS m/e (M + H)$^+$ | Retention Time (min) |
|---|---|---|
| 14 | 365 | 8.4 |
| 15 | 360 | 9.6 |
| 16 | 389 | 10.2 |

Example 17

4-[(3-Chlorophenyl)amino]-2-ethyl-5-(2-methyl-1,3-thiazol-yl)-6-phenylpyridazin-3(2H)-one Obtained as a solid (65%) from the title compound of Preparation 25 and the corresponding boronic acid following the procedure of Example 5.

LRMS: m/Z 423 (M+1)$^+$.

Retention Time: 9.9 min.

Example 18

4-[(3-Chlorophenyl)amino]-2-ethyl-6-phenyl-5-(2-phenyl-1,3-thiazol-4-yl)pyridazin-3(2H)-one Obtained as a solid (50%) from the title compound of Preparation 26 and the corresponding boronic acid following the procedure of Example 5.

LRMS: m/Z 486 (M+1)$^+$.

Retention Time: 10.8 min.

Example 19

4-[(3-Chlorophenyl)amino]-2-ethyl-5-(1-methyl-1H-pyrazol-5-yl)-6-phenylpyridazin-3(2H)-one Obtained as a solid (73%) from the title compound of Preparation 28 and the corresponding boronic acid following the procedure of Example 5.

LRMS: m/Z 406 (M+1)$^+$.

Retention Time: 9.5 min.

Examples 20-21

4-{[2-Ethyl-5-(5-methyl-1,3,4-oxadiazol-2-yl)-3-oxo-6-phenyl-2,3-dihydropyridazin-4-yl]amino}benzonitrile 2-Ethyl-5-(5-methyl-1,3,4-oxadiazol-2-yl)-6-phenyl-4-[(3,4,5-trifluorophenyl)amino]pyridazin-3(2H)-one The title compounds were synthesized from the title compound of Preparation 30 and the corresponding boronic acid following the procedure of Example 5. The ESI/MS data and HPLC retention times are summarized in Table 4.

TABLE 4

| EXAMPLE | ESI/MS m/e (M + H)+ | Retention Time (min) |
|---|---|---|
| 20 | 399 | 8.3 |
| 21 | 428 | 9.2 |

Example 22

4-[(3-Chlorophenyl)amino]-2-ethyl-6-phenylpyridazin-3(2H)-one

To a stirred solution of 3,4-dichloro-6-phenylpyridazine (Sircar, I, *J. Het Chem,* 1983, 20, 1473-76) (100 mg, 0.44 mmol) in ethanol (1 mL), 3-chloroaniline (70 µL, 0.66 mmol) was added and the final mixture was refluxed for 4 h. Solvent was removed under reduced pressure and the residue was suspended in acetic acid (1 mL) and refluxed for 8 h. Then solvent was removed under reduced pressure and the residue was suspended in water and treated with 10% ammonia solution to pH 8. It was extracted with dichloromethane, the combined organic layers were dried and solvent was finally removed under reduced pressure.

To a solution of the crude product thus obtained in dimethylformamide (2 mL), potassium carbonate (117 mg, 0.85 mmol) and ethyl bromide (70 µL, 0.94 mmol) were added and the final mixture was stirred at rt for 5 hours. It was then poured onto brine and extracted with dichloromethane. The combined organic layers were dried and solvent was removed under reduced pressure to yield a crude product that was purified by column chromatography on silica gel (15% overall yield).

LRMS: m/Z 326 (M+1)+.
Retention Time: 10.7 min.

Examples 23-24

2-Ethyl-4-[(3-fluorophenyl)amino]-6-phenylpyridazin-3(2H)-one

2-Ethyl-4-(1-naphthylamino)-6-phenylpyridazin-3(2H)-one

The title compounds were synthesized from 3,4-dichloro-6-phenylpyridazine (Sircar, I, *J. Het. Chem.,* 1983, 20, 1473-76) and the corresponding aniline following the procedure of Example 22. The ESI/MS data and HPLC retention times are summarized in Table 5.

TABLE 5

| EXAMPLE | ESI/MS m/e (M + H)+ | Retention Time (min) |
|---|---|---|
| 23 | 310 | 10.2 |
| 24 | 342 | 10.7 |

Example 25

2-Ethyl-6-phenyl-4-(pyridin-3-ylamino)pyridazin-3(2H)-one

Obtained as a solid (31%) from the title compound of Preparation 34 and the corresponding bromide following the procedure of Example 13.

LRMS: m/Z 293 (M+1)+.

δ(DMSO-d$_6$): 1.37 (t, 3H), 4.23 (q, 2H), 7.14 (s, 1H), 7.43 (m, 4H), 7.82 (m, 2H), 7.92 (d, 1H), 8.32 (d, 1H), 8.70 (s, 1H), 9.03 (s, 1H).

Example 26

2-Ethyl-6-phenyl-4-(quinolin-5-ylamino)pyridazin-3(2H)-one

Obtained as a solid (14%) from the title compound of Preparation 34 and the corresponding boronic acid following the procedure of Example 5.

LRMS: m/Z 343 (M+1)+.

δ(DMSO-d$_6$): 1.40 (t, 3H), 4.30 (q, 2H), 6.50 (s, 1H), 7.40 (m, 3H), 7.55 (m, 3H), 7.70 (m,1H), 7.80 (m, 1H), 8.00 (m, 1H), 8.30 (m, 1H), 8.95 (m, 1H), 9.10 (s, 1H).

Example 27

4-(Diquinolin-5-ylamino)-2-ethyl-6-phenylpyridazin-3(2H)-one

Obtained as a solid (8%) from the title compound of Preparation 34 and the corresponding boronic acid following the procedure of Example 5.

LRMS: m/Z 469 (M+1)+.

δ(DMSO-d$_6$): 1.30 (t, 3H), 4.12 (q, 2H), 6.69 (s, 1H), 7.35-7.46 (m, 9H), 7.71 (bs, 2H), 7.97 (d, 2H), 8.20 (m, 2H), 8.92 (bs, 2H).

Example 28

4-[Bis(3,4,5-trifluorophenyl)amino]-2-ethyl-6-phenylpyridazin-3(2H)-one

Obtained as a solid (10%) from the title compound of Preparation 34 and the corresponding bromide following the procedure of Example 13.

LRMS: m/Z 476 (M+1)+.

δ(DMSO-d$_6$): 1.30 (t, 3H), 4.15 (q, 2H), 7.20 (m, 4H), 7.40 (m, 3H), 7.55 (s, 1H), 7.80 (m, 2H).

Example 29

4-[Bis(3,4-difluorophenyl)amino]-2-ethyl-6-phenylpyridazin-3(2H)-one

Obtained as a solid (82%) from the title compound of Preparation 34 and the corresponding boronic acid following the procedure of Example 5.

LRMS: m/Z 440 (M+1)+.

δ (DMSO-d$_6$): 1.32 (t, 3H), 4.15 (q, 2H), 6.92 (m, 2H), 7.23 (m, 2H), 7.30 (s, 1H), 7.42 (m, 5H), 7.75 (m, 2H).

Example 30

4-[(3,4-Difluorophenyl)amino]-2-ethyl-6-phenylpyridazin-3(2H)-one

Obtained as a solid (20%) from the title compound of Preparation 34 and the corresponding boronic acid following the procedure of Example 5.

δ (DMSO-$d_6$): 1.35 (t, 3H), 4.21 (q, 2H), 7.13 (s, 1H), 7.30 (m, 1H), 7.46 (m, 4H), 7.55 (m,1H), 7.81 (d, 2H), 8.95 (s, 1H).

Example 31

4-[(3-Chloro-4-fluorophenyl)amino]-2-ethyl-6-phenylpyridazin-3(2H)-one

Obtained as a solid (42%) from the title compound of Preparation 34 and the corresponding boronic acid following the procedure of Example 5.

LRMS: m/Z 344 (M+1)$^+$.

δ (DMSO-$d_6$): 1.36 (t, 3H), 4.23 (q, 2H), 7.10 (s, 1H), 7.41-7.49 (m, 5H), 7.64 (m, 1H), 7.81 (m,2H), 8.96 (s, 1H).

Example 32

4-[(2-Ethyl-3-oxo-6-phenyl-2,3-dihydropyridazin-4-yl)amino]benzonitrile

Obtained as a solid (21%) from the title compound of Preparation 34 and the corresponding boronic acid following the procedure of Example 5.

LRMS: m/Z 317 (M+1)$^+$.

δ (DMSO-$d_6$): 1.37 (t, 3H), 4.24 (q, 2H), 7.46 (m, 4H), 7.66 (m, 2H), 7.84 (m, 4H), 9.28 (s, 1H).

Example 33

2-Ethyl-4-[(1-oxidopyridin-3-yl)amino]-6-phenylpyridazin-3(2H)-one

A solution of the compound synthesised in Example 25 (100 mg, 0.342 mmol) in dichloromethane (4 mL) was added dropwise to a cold solution of 3-chloroperoxybenzoic acid (69 mg, 0.342 mmol) in methylene chloride (2 mL). The mixture was stirred at room temperature for 27 hours and added to a solution of $KHSO_4$ in water (15 mL, 25%). The organic layer washed with water, dried over sodium sulfate anhydride and evaporated.

The crude obtained was purified by column chromatography (silica gel, methylene chloride/methanol) to yield 73 mg (0.237 mmol) of the title compound (70%).

LRMS: m/Z 309 (M+1)$^+$.

δ (DMSO-$d_6$): 1.37 (t, 3H), 4.23 (q, 2H), 7.29 (s, 1H), 7.37-7.45 (m, 4H), 7.55 (d, 1H), 7.85 (m, 2H), 7.96 (d,1H), 8.37 (s, 1H), 9.12 (s, 1H).

Example 34

2-Ethyl-6-pyridin-3-yl-4-(pyridin-3-ylamino)pyridazin-3(2H)-one

Obtained as a solid (15%) from the title compound of Preparation 36 and the corresponding bromide following the procedure of Example 13.

LRMS: m/Z 294 (M+1)$^+$.

δ(CDCl$_3$): 1.49 (t, 3H), 4.38 (q, 2H), 7.07 (s, 1H), 7.38 (m, 2H), 7.62 (d, 1H), 7.70 (s, 1H), 8.06 (d, 1H), 8.47 (s, 1H), 8.66 (s, 2H), 8.99 (s, 1H).

Example 35

2-Ethyl-4-[(1-oxidoquinolin-5-yl)amino]-6-phenylpyridazin-3(2H)-one

Obtained as a solid (53%) from the title compound of Example 26 using the experimental procedure described in Example 33.

LRMS: m/Z 359 (M+1)$^+$.

δ(DMSO-$d_6$): 1.50 (t, 3H), 4.40 (q, 2H), 6.75 (s, 1H), 7.35 (m, 5H), 7.60 (m, 1H), 7.70 (m, 1H), 7.80 (m, 1H), 7.90 (m, 1H), 8.10 (s, 1H), 8.60 (dd, 2H).

Example 36

2-Ethyl-6-pyridin-4-yl-4-(pyridin-3-ylamino)pyridazin-3(2H)-one

Obtained as a solid (16%) from the title compound of Preparation 40 and the corresponding bromide following the procedure of Example 13.

LRMS: m/Z 294 (M+1)$^+$.

δ(DMSO-$d_6$): 1.38 (t, 3H), 4.26 (q, 2H), 7.22 (s, 1H), 7.44 (m, 1H), 7.81 (m, 2H), 7.94 (m, 1H), 8.34 (d, 1H), 8.65 (d, 2H), 8.70 (s, 1H), 9.13 (s, 1H).

Example 37

2-Ethyl-4-(isoquinolin-4-ylamino)-6-phenylpyridazin-3(2H)-one

Obtained as a solid (10%) from the title compound of Preparation 34 and the corresponding bromide following the procedure of Example 13.

LRMS: m/Z 343 (M+1)$^+$.

δ(DMSO-$d_6$): 1.41 (t, 3H), 4.27 (q, 2H), 6.35 (s, 1H), 7.34 (m, 3H), 7.57 (m, 2H), 7.75-7.86 (m, 3H), 8.24 (d, 1H), 8.58 (s, 1H), 9.11 (s, 1H), 9.30 (s, 1H).

Example 38

2-Ethyl-6-phenyl-4-[(3,4,5-trifluorophenyl)amino]pyridazin-3(2H)-one

Obtained as a solid (27%) from the title compound of Preparation 34 and the corresponding boronic acid following the procedure of Example 5.

LRMS: m/Z 346 (M+1)$^+$.

δ (DMSO-$d_6$): 1.36 (t, 3H), 4.22 (q, 2H), 7.27 (s, 1H), 7.43-7.49 (m, 5H), 7.85 (d, 2H), 9.05 (s, 1H).

Example 39

2-Ethyl-4-[(4-fluorophenyl)amino]-6-phenylpyridazin-3(2H)-one

Obtained as a solid (17%) from the title compound of Preparation 34 and the corresponding boronic acid following the procedure of Example 5.

LRMS: m/Z 310 (M+1)$^+$.

δ (DMSO-d$_6$): 1.36 (t, 3H), 4.22 (q, 2H), 7.01 (s, 1H), 7.24 (m, 2H), 7.41-7.50 (m, 5H), 7.78 (m, 2H), 8.87 (s, 1H).

Example 40

2-Ethyl-6-pyridin-3-yl-4-(quinolin-5-ylamino)pyridazin-3(2H)-one

Obtained as a solid (0.8%) from the title compound of Preparation 36 and the corresponding boronic acid following the procedure of Example 5.

LRMS: m/Z 344 (M+1)$^+$.
Retention Time: 6.9 min.

Example 41

2-Methyl-6-pyridin-3-yl-4-(quinolin-5-ylamino)pyridazin-3(2H)-one

Obtained as a solid (1.1%) from the title compound of Preparation 38 and the corresponding boronic acid following the procedure of Example 5.
LRMS: m/Z 330 (M+1)$^+$.
Retention Time: 6.1 min.

Example 42

2-Ethyl-6-pyridin-4-yl-4-(quinolin-5-ylamino)pyridazin-3(2H)-one

Obtained as a solid (0.6%) from the title compound of Preparation 40 and the corresponding boronic acid following the procedure of Example 5.
LRMS: m/Z 344 (M+1)$^+$.
Retention Time: 6.2 min.

Example 43

2-Ethyl-4-{[4-(hydroxymethyl)phenyl]amino}-6-phenylpyridazin-3(2H)-one

Obtained as a solid (0.6%) from the title compound of Preparation 34 and the corresponding boronic acid following the procedure of Example 5.
LRMS: m/Z 322 (M+1)$^+$.
Retention Time: 9.0 min.

Example 44

4-[(2-Methyl-3-oxo-6-pyridin-3-yl-2,3-dihydropyridazin-4-yl)amino]benzonitrile Obtained as a solid (0.3%) from the title compound of Preparation 38 and the corresponding boronic acid following the procedure of Example 5.
LRMS: m/Z 304 (M+1)$^+$.
Retention Time: 7.2 min.

Example 45

4-[(2-Ethyl-3-oxo-6-pyridin-3-yl-2,3-dihydropyridazin-4-yl)amino]benzonitrile Obtained as a solid (8%) from the title compound of Preparation 36 and the corresponding boronic acid following the procedure of Example 5.
LRMS: m/Z 318 (M+1)$^+$.
δ (DMSO-d$_6$): 1.38 (t, 3H), 4.25 (q, 2H), 7.50 (m, 2H), 7.68 (m, 2H), 7.80 (m, 2H), 8.25 (d, 1H), 8.64 (d, 1H), 9.07 (s, 1H), 9.34 (s, 1H).

Example 46

Methyl 4-[(2-ethyl-3-oxo-6-phenyl-2,3-dihydropyridazin-4-yl)amino]benzoate

Obtained as a solid (49%) from the title compound of Preparation 34 and the corresponding boronic acid following the procedure of Example 5.
LRMS: m/Z 350 (M+1)$^+$.
δ (DMSO-d$_6$): 1.35 (t, 3H), 3.85 (s, 3H), 4.25 (q, 2H), 7.40 (s, 1H), 7.50 (m, 3H), 7.60 (d, 2H), 7.85 (m, 2H), 7.95 (d, 2H), 9.20 (s, 1H).

Example 47

4-{[2-Ethyl-6-(1-oxidopyridin-3-yl)-3-oxo-2,3-dihydropyridazin-4-yl]amino}benzonitrile Obtained as a solid (66%) from the title compound of Example 45 using the experimental procedure described in Example 33.
LRMS: m/Z 334 (M+1)$^+$.
δ (DMSO-d$_6$): 1.37 (t, 3H), 4.24 (q, 2H), 7.45 (s, 1H), 7.49 (m, 1H), 7.69 (d, 2H), 7.81 (d, 3H), 8.28 (d, 1H), 8.73 (s, 1H), 9.37 (s, 1H).

Example 48

2-Ethyl-4-(isoquinolin-4-ylamino)-6-pyridin-3-ylpyridazin-3(2H)-one

Obtained as a solid (2.4%) from the title compound of Preparation 36 and the corresponding bromide following the procedure of Example 13.
LRMS: m/Z 344 (M+1)$^+$.
δ(DMSO-d$_6$): 1.42 (t, 3H), 4.29 (q, 2H), 6.46 (s, 1H), 7.37 (m, 1H), 7.75-7.89 (m, 3H), 7.99 (d, 1H), 8.24 (d, 1H), 8.54 (m, 2H), 8.81 (s, 1H), 9.17 (s, 1H), 9.30 (s, 1H).

Example 49

2-Ethyl-4-[(4-methylpyridin-3-yl)amino]-6-pyridin-3-ylpyridazin-3(2H)-one

Obtained as a solid (20%) from the title compound of Preparation 36 and the corresponding bromide following the procedure of Example 13.

LRMS: m/Z 308 (M+1)$^+$.

$\delta$(DMSO-d$_6$): 1.39 (t, 3H), 3.35 (s, 3H), 4.24 (q, 2H), 6.40 (s, 1H), 7.37-7.45 (m, 2H), 8.10 (m, 1H), 8.38 (d, 1H), 8.50 (s, 1H), 8.58 (d, 1H), 8.73 (s, 1H), 8.92 (s, 1H).

Example 50

2-Ethyl-4-(isoquinolin-4-ylamino)-6-pyridin-4-ylpyridazin-3(2H)-one

Obtained as a solid (14%) from the title compound of Preparation 40 and the corresponding bromide following the procedure of Example 13.

LRMS: m/Z 344 (M+1)$^+$.

$\delta$(DMSO-d$_6$): 1.42 (t, 3H), 4.30 (q, 2H), 6.47 (s, 1H), 7.59 (d, 2H), 7.75-7.88 (m, 3H), 8.25 (d, 1H), 8.53 (d, 2H), 8.60 (s, 1H), 9.20 (s, 1H), 9.30 (s, 1H).

Example 51

4-[(2-Ethyl-3-oxo-6-phenyl-2,3-dihydropyridazin-4-yl)amino]benzoic acid

To a solution of the title compound of Example 46 (150 mg, 0.429 mmol) in methanol (12 mL) and tetrahydrofuran (8 mL) was added a solution of LiOH/H$_2$O (72 mg, 1.72 mmol) in water (2 mL). The mixture was stirred at room temperature for 40 hours. An additional amount of LiOH/H$_2$O (36 mg, 0.86 mmol) was added and the stirring maintained for 24 hours more. Solvents were evaporated and the residue dissolved in water. The solution was acidified with HCl 2N and extracted with methylene chloride. The organic layer washed with water, brine, dried over sodium sulfate anhydride and evaporated.

The crude obtained was purified by column chromatography (silica gel, methylene chloride/acetic acid) to yield 100 mg (0.298 mmol) of the title compound (69%).

LRMS: m/Z 336 (M+1)$^+$.

$\delta$(DMSO-d$_6$): 1.37 (t, 3H), 4.24 (q, 2H), 7.36 (s, 1H), 7.41-7.49 (m, 3H), 7.57 (d, 2H), 7.85 (d, 2H), 7.95 (d, 2H), 9.13 (s, 1H), 12.70 (bs, 1H).

Example 52

2-Ethyl-4-[(4-methylpyridin-3-yl)amino]-6-pyridin-4-ylpyridazin-3(2H)-one

Obtained as a solid (11%) from the title compound of Preparation 40 and the corresponding bromide following the procedure of Example 13.

LRMS: m/Z 308 (M+1)$^+$.

$\delta$(DMSO-d$_6$): 1.39 (t, 3H), 3.34 (s, 3H), 4.25 (q, 2H), 6.41 (s, 1H), 7.40 (bs, 1H), 7.71 (bs, 2H), 8.30-8.76 (m, 4H), 8.78 (s, 1H).

Example 53

4-[(2-Ethyl-3-oxo-6-pyridin-4-yl-2,3-dihydropyridazin-4-yl)amino]benzonitrile

Obtained as a solid (11%) from the title compound of Preparation 40 and the corresponding boronic acid following the procedure of Example 5.

LRMS: m/Z 318 (M+1)$^+$.

$\delta$ (DMSO-d$_6$): 1.38 (t, 3H), 4.26 (q, 2H), 7.49 (s, 1H), 7.68 (m, 2H), 7.81-7.87 (m, 4H), 8.67 (d, 2H), 9.37 (s, 1H).

Example 54

4-[(2-Ethyl-3-oxo-6-phenyl-2,3-dihydropyridazin-4-yl)(methyl)amino]benzonitrile

To a solution of the title compound of Example 32 (150 mg, 0.474 mmol) in N,N-dimethylformamide (8 mL) was added iodomethane (131 mg, 1.422 mmol) and potassium carbonate (131 mg, 0.948 mmol). The mixture was stirred at room temperature for 4 hours. Water (40 mL) was added and the solution extracted with ethyl acetate. The organic layer washed with water, dried over sodium sulphate anhydride and evaporated. The crude obtained was purified by column chromatography (silica gel, hexane/ethyl acetate) to yield 100 mg (0.303 mmol) of the title compound (64%).

LRMS: m/Z 331 (M+1)$^+$.

$\delta$ (DMSO-d$_6$): 1.31 (t, 3H), 3.44 (s, 3H), 4.16 (q, 2H), 7.05 (d, 2H), 7.46-7.50 (m, 3H), 7.65 (d, 2H), 7.77 (s, 1H), 7.94 (d, 2H).

Example 55

N-(4-Cyanophenyl)-N-(2-ethyl-3-oxo-6-phenyl-2,3-dihydropyridazin-4-yl)acetamide

The title compound of Example 32 (100 mg, 0.316 mmol) was added to acetic anhydride (2 mL) and refluxed for 22 hours. Ice was added and the mixture extracted with methylene chloride. The organic layer washed with NaHCO$_3$ 4%, water and brine, dried over sodium sulfate anhydride and evaporated. The crude obtained was purified by column chromatography (silica gel, hexane/ethyl acetate) to yield 80 mg (0.223 mmol) of the title compound (71%).

LRMS: m/Z 359 (M+1)$^+$.

$\delta$ (DMSO-d$_6$): 1.35 (t, 3H), 3.32 (s, 3H), 4.21 (q, 2H), 7.51 (m, 3H), 7.58 (d, 2H), 7.86 (d, 2H), 7.93 (d, 2H), 8.40 (s, 1H).

Example 56

6-(3-Chlorophenyl)-2-ethyl-4-(pyridin-3-ylamino)pyridazin-3(2H)-one

Obtained as a solid (33%) from the title compound of Preparation 43 and the corresponding bromide following the procedure of Example 13.

LRMS: m/Z 327 (M+1)$^+$.

$\delta$(DMSO-d$_6$): 1.37 (t, 3H), 4.24 (q, 2H), 7.16 (s, 1H), 7.42-7.49 (m, 3H), 7.78 (m, 1H), 7.88 (s, 1H), 7.92 (m, 1H), 8.33 (d, 1H), 8.71 (s, 1H), 9.04 (s, 1H).

Example 57

2-Ethyl-4-[methyl(quinolin-5-yl)amino]-6-phenylpyridazin-3(2H)-one

Obtained as a solid (32%) from the title compound of Example 26 using the experimental procedure described in Example 54.

LRMS: m/Z 357 (M+1)$^+$.

δ (DMSO-d$_6$): 1.15 (t, 3H), 3.36 (s, 3H), 3.95 (q, 2H), 7.14 (s, 1H), 7.23 (d, 1H), 7.42-7.65 (m, 5H), 7.90 (m, 3H), 8.35 (d, 1H), 8.91 (s, 1H).

Example 58

6-(3-Chlorophenyl)-2-ethyl-4-(isoquinolin-4-ylamino)pyridazin-3(2H)-one

Obtained as a solid (26%) from the title compound of Preparation 43 and the corresponding bromide following the procedure of Example 13.

LRMS: m/Z 377 (M+1)$^+$.

δ(DMSO-d$_6$): 1.41 (t, 3H), 4.28 (q, 2H), 6.44 (s, 1H), 7.35-7.42 (m, 2H), 7.52 (d, 1H), 7.70-7.88 (m, 4H), 8.23 (d, 1H), 8.59 (s, 1H), 9.11 (s,1H), 9.30 (s, 1H).

Example 59

N-(2-ethyl-3-oxo-6-phenyl-2,3-dihydropyridazin-4-yl)-N-quinolin-5-yl acetamide

Obtained as a solid (45%) from the title compound of Example 26 using the experimental procedure described in Example 55.

LRMS: m/Z 385 (M+1)$^+$.

δ (DMSO-d$_6$): 1.34 (t, 3H), 2.06 (s, 3H), 4.23 (q, 2H), 7.48 (m, 3H), 7.63 (m, 1H), 7.80-7.90 (m, 4H), 8.07 (d, 1H), 8.24 (s, 1H), 8.70 (d, 1H), 8.96 (m, 1H).

Example 60

2-Ethyl-4-(4-hydroxymethyl-phenylamino)-6-pyridin-3-ylpyridazin-3(2H)-one

Obtained as a solid (3%) from the title compound of Preparation 36 and the corresponding boronic acid following the procedure of Example 5.

LRMS: m/Z 323 (M+1)$^+$.

Retention Time: 11 min.

Example 61

2-Ethyl-4-(isoquinolin-4-ylamino)-6-(4-methoxyphenyl)pyridazin-3(2H)-one

A stirred mixture of the title compound of Preparation 52 (115 mg, 0.47 mmol), 4 bromoisoquinoline (117 mg, 0.56 mmol), anhydrous copper(I) iodide (8.9 mg, 0.047 mmol), N,N'-dimethylethylenediamine (8.3 mg, 0.094 mmol) and potassium carbonate (130 mg, 0.94 mmol) in anhydrous dioxane (2 mL) was heated in an Emrys™ Optimizer microwave device at 160° C. for 40 min. The reaction mixture was filtered through a pad of Celite©, the solvent was evaporated under reduced pressure and the residue purified by column chromatography (C-18 reverse phase Biotage© cartridge (water (0.1M ammonium acetate)/acetonitrile 95:5 to 5:95) to give the title compound as a solid (19% yield).

δ(DMSO-d6): 1.4 (t, 3H), 3.78 (s, 3H), 4.28 (q, 2H), 6.32 (s, 1H), 6.90 (d, 2H), 7.54 (d, 2H), 7.70-7.90 (m, 3H), 8.25 (d, 1H), 8.58 (s, 1H), 9.10 (s, 1H), 9.30 (s, 1H).

LRMS: (m/z): 373 (M+1)$^+$.

Retention Time: 10.1 min.

Example 62

2-Ethyl-6-(4-methoxyphenyl)-4-(quinolin-5-ylamino)pyridazin-3(2H)-one

A mixture of the title compound of Preparation 52 (115 mg, 0.47 mmol), 5-quinolylboronic acid (162 mg, 0.94 mmol), anhydrous cupric acetate (128 mg, 0.70 mmol), triethylamine (0.13 mL, 0.94 mmol) and 4 Å activated molecular sieves (368 mg) in dry dichloromethane (2 mL) was heated in an Emrys™ Optimizer microwave device at 120° C. for 40 min. The reaction mixture was filtered through a pad of Celite©, the solvent was removed under reduced pressure and the residue purified by column chromatography (C-18 reverse phase Biotage© cartridge (water (0.1M ammonium acetate)/acetonitrile 95:5 to 5:95) to give the title compound as a solid (4% yield).

LRMS: (m/z): 373 (M+1)$^+$.

Retention Time: 10.08 min.

Example 63

4-Anilino-2-ethyl-6-phenylpyridazin-3(2H)-one

To a suspension of the title compound of Preparation 56 (70 mg, 0.27 mmol) and anhydrous potassium carbonate (112 mg, 0.81 mmol) in dry dimethylformamide (2.5 mL) was added ethyl bromide (88 mg, 0.81 mmol) and the resulting mixture stirred at r.t. overnight. The mixture was concentrated and the residue thus obtained was diluted with ethyl acetate (100 mL), washed with water and brine, dried and concentrated to yield a residue which was purified by column chromatography (Biotage© cartridge CH$_2$Cl$_2$/Et$_2$O 95:5) to give the title compound as a white solid (41% yield).

δ(CD3OD): 1.45 (t, 3H), 4.31 (q, 2H), 7.15 (s, 1H), 7.20 (m, 2H), 7.36-7.47 (m, 6H), 7.76 (d, 2H).

LRMS: (m/z): 292 (M+1)$^+$.

Retention Time: 10.54 min.

Example 64

2-Ethyl-6-(4-methylphenyl)-4-(quinolin-5-ylamino)pyridazin-3(2H)-one

Obtained as a solid (8%) from the title compound of Preparation 61 and 5-quinolylboronic acid following the procedure of Example 5. The final product was purified by column chromatography (018 reverse phase Biotage© cartridge (water (0.1M ammonium acetate)/acetonitrile 95:5 to 5:95)).

δ(DMSO-d6): 1.40 (t, 3H), 2.28 (s, 3H), 4.26 (q, 2H), 6.45 (s, 1H), 7.16 (d, 2H), 7.49 (d, 2H), 7.55 (dd, 1H), 7.68 (d, 1H), 7.84 (t, 1H), 7.98 (d, 1H), 8.31 (d, 1H), 8.95 (d, 1H), 9.07 (s, 1H).

LRMS: (m/z): 357 (M+1)$^+$.

Retention Time: 10.67 min.

Example 65

2-Ethyl-6-(4-methylphenyl)4[(1-oxidoquinolin-5-yl)amino]pyridazin-3(2H)-one

Obtained as a yellow solid (13%) from the title compound of example 64 following the experimental procedure described in Example 33. The final product was purified by column chromatography (C-18 reverse phase Biotage© cartridge (water (0.1M ammonium acetate)/acetonitrile 95:5 to 5:95)).

δ(DMSO-d6): 1.40 (t, 3H), 2.28 (s, 3H), 4.26 (q, 2H), 6.52 (s, 1H), 7.17 (d, 2H), 7.46 (dd, 1H), 7.54 (d, 2H), 7.75-7.90 (m, 3H), 8.48 (d, 1H), 8.62 (d, 1H), 9.12 (s, 1H).

LRMS (m/z): 373 (M+1)$^+$.
Retention Time: 9.85 min.

Example 66

2-Ethyl-6-phenyl-4-(thieno[2,3-c]pyridin-3-ylamino)pyridazin-3(2H)-one

Obtained as a solid (22%) from the title compound of Preparation 34 and 3-bromo-thieno[2,3-c]pyridine (S. Gronowitz, E. Sandberg, *Arkiv für Kemi*, 1970, 32, 249-68) following the procedure of Example 13.

δ(CDCl$_3$): 1.52 (t, 3H), 4.39 (q, 2H), 6.87 (s, 1H), 7.38 (m, 3H), 7.51 (s, 1H), 7.67 (m, 3H), 7.78 (s, 1H), 8.59 (m, 1H), 9.19 (s, 1H).

LRMS (m/z): 349 (M+1)$^+$.
Retention Time: 14 min.

Example 67

1-Ethyl-6-oxo-3-phenyl-5-(pyridin-3-ylamino)-1,6-dihydropyridazine-4-carbonitrile Obtained as a solid (20%) from the title compound of Preparation 8 and 3-bromopyridine following the procedure of Example 13.

LRMS (m/z): 349 (M+1)$^+$.
Retention Time*: 8.0 min.

Example 68

1-Ethyl-3-(3-methylphenyl)-6-oxo-5-(pyridin-3-ylamino)-1,6-dihydropyridazine-4-carbonitrile Obtained as a solid (47%) from the title compound of Preparation 69 and pyridine-3-boronic acid following the procedure of Example 5. The reaction mixture was refluxed for 13 h.

LRMS (m/z): 318 (M+1)$^+$.
Retention Time: 14 min.

Example 69

2-Ethyl-5-(1-hydroxyethyl)-6-phenyl-4-(quinolin-5-ylamino)pyridazin-3(2H)-one

Obtained as a solid (99%) from the title compound of Preparation 70 following the procedure of Example 1.

δ(CDCl$_3$): 1.36 (m, 6H), 2.88 (d, 1H), 4.16 (m, 1H), 4.30 (m, 1H), 4.91 (m, 1H), 6.95 (d, 1H), 7.41 (m, 3H), 7.46 (m, 3H), 7.61 (t, 1H), 7.85 (d, 1H), 8.33 (s, 1H), 8.43 (d, 1H), 8.87 (s, 1H).

LRMS (m/z): 387 (M+1)$^+$.
Retention Time: 11 min.

Example 70

2-Ethyl-6-(4-methylphenyl)-4-(pyridin-3-ylamino)pyridazin-3(2H)-one

Obtained as a solid (8%) from the title compound of Preparation 61 and 3-bromopyridine following the experimental procedure described in Example 13.

δ(DMSO-d$_6$): 1.36 (t, 3H), 2.34 (s, 3H), 4.23 (q, 2H), 7.11 (s, 1H), 7.27 (d, 2H), 7.43 (dd, 1H), 7.70 (d, 2H), 7.90 (m, 1H), 8.32 (d, 1H), 8.69 (s, 1H), 8.97 (bs, NH).

LRMS (m/z): 307 (M+1)$^+$.
Retention Time: 16 min.

Example 71

2-Ethyl-44 isoquinolin-4-ylamino)-6-(4-methylphenyl)pyridazin-3(2H)-one

Obtained as a solid (6%) from the title compound of Preparation 61 and 4-bromoisoquinoline following the experimental procedure described in Example 13.

δ(DMSO-d$_6$): 1.41 (t, 3H), 2.27 (s, 3H), 4.25 (q, 2H), 6.33 (s, 1H), 7.16 (d, 2H), 7.45 (d, 2H), 7.73-7.87 (m, 3H), 8.23 (d, 1H), 8.57 (s, 1H), 9.05 (s, 1H), 9.30 (bs, NH).

LRMS (m/z): 357 (M+1)$^+$.
Retention Time: 17 min.

Example 72

2-Ethyl-6-(4-methylphenyl)-4-[(4-methylpyridin-3-yl)amino]pyridazin-3(2H)-one

Obtained as a solid (10%) from the title compound of Preparation 61 and 3-bromo-4-methylpyridine following the experimental procedure described in Example 13.

δ(DMSO-d$_6$): 1.37 (t, 3H), 2.21 (s, 3H), 2.31 (s, 3H), 4.21 (q, 2H), 6.29 (s, 1H), 7.22 (d, 2H), 7.39 (d, 1H), 7.57 (d, 2H), 8.38 (d, 1H), 8.48 (s, 1H), 8.60 (bs, NH).

LRMS (m/z): 321 (M+1)$^+$.
Retention Time: 9.51 min.

Example 73

2-Ethyl-6-(3-methylphenyl)-4-(pyridin-3-ylamino)pyridazin-3(2H)-one

Obtained as a solid (8%) from the title compound of Preparation 75 and 3-bromopyridine following the experimental procedure described in Example 13.

δ(DMSO-d6): 1.37 (t, 3H), 2.36 (s, 3H), 4.24 (q, 2H), 7.11 (s, 1H), 7.24 (d, 1H), 7.33 (t, 1H), 7.44 (dd, 1H), 7.57 (d, 1H), 7.62 (s, 1H), 7.90 (m, 1H), 8.34 (d, 1H), 8.70 (s, 1H), 8.99 (bs, NH).

LRMS (m/z): 307 (M+1)$^+$.
Retention Time: 15 min.

Example 74

2-Ethyl-4-(isoquinolin-4-ylamino)-6-(3-methylphenyl)pyridazin-3(2H)-one

Obtained as a solid (19%) from the title compound of Preparation 75 and 4-bromoisoquinoline following the experimental procedure described in Example 13.

δ(DMSO-$d_6$): 1.41 (t, 3H), 2.27 (s, 3H), 4.27 (q, 2H), 6.35 (s, 1H), 7.16 (d, 1H), 7.22 (t, 1H), 7.31 (d, 1H), 7.42 (bs, 1H), 7.75 (t, 1H), 7.82 (t, 1H), 7.86 (d, 1H), 8.23 (d, 1H), 8.58 (s, 1H), 9.06 (s, 1H), 9.30 (bs, NH).

LRMS (m/z): 357 (M+1)$^+$.

Retention Time: 17 min.

Example 75

2-Ethyl-6-(3-methylphenyl)-4-[(4-methylpyridin-3-yl)amino]pyridazin-3(2H)-one

Obtained as a solid (44%) from the title compound of Preparation 75 and 3-bromo-4-methylpyridine following the experimental procedure described in Example 13.

δ(DMSO-$d_6$): 1.38 (t, 3H), 2.23 (s, 3H), 2.32 (s, 3H), 4.24 (q, 2H), 6.32 (s, 1H), 7.20 (d, 1H), 7.28 (t, 1H), 7.37 (d, 1H), 7.50 (s, 1H), 8.37 (d, 1H), 8.44 (s, 1H), 8.49 (bs, NH).

LRMS (m/z): 321 (M+1)$^+$.

Retention Time: 15 min.

Example 76

4-{[2-Ethyl-6-(3-methylphenyl)-3-oxo-2,3-dihydropyridazin-4-yl]amino}benzoic acid The title compound of Preparation 76 (40 mg, 0.11 mmole) was treated with 3 mL of a solution of LiOH (6.5 mg, 0.264 mmole) in water/THF/MeOH (1:1:1) and stirred at room temperature overnight. The volatile solvents of the mixture were removed under reduced pressure and the row material redissolved in methanol and purified by column chromatography (C-18 reverse phase Biotage© cartridge (water (0.1M ammonium acetate)/acetonitrile 95:5 to 5:95)) to give the title compound as a white solid (16 mg, 4% yield).

δ(CD$_3$OD): 1.36 (t, 3H), 2.31 (s, 3H), 4.24 (q, 2H), 7.15 (d, 1H), 7.23 (t, 1H), 7.28 (s, 1H), 7.37 (d, 2H), 7.48 (d, 1H), 7.54 (s, 1H), 7.98 (d, 2H).

LRMS (m/z): 350 (M+1)+.

Retention Time: 17 min.

Example 77

2-Ethyl-6-(5-methylpyridin-3-yl)-4-(pyridin-3-ylamino)pyridazin-3(2H)-one

Obtained as a solid (9%) from the title compound of Preparation 81 and 3-bromopyridine following the experimental procedure described in Example 13.

LRMS (m/z): 308 (M+1)$^+$.

Retention Time: 12 min.

Example 78

2-Ethyl-4-(isoquinolin-4-ylamino)-6-(5-methylpyridin-3-yl)pyridazin-3(2H)-one

Obtained as a solid (21%) from the title compound of Preparation 81 and 4-bromoisoquinoline following the experimental procedure described in Example 13.

δ(DMSO-$d_6$): 1.42 (t, 3H), 2.27 (s, 3H), 4.29 (q, 2H), 6.46 (s, 1H), 7.73-7.89 (m, 4H), 8.24 (d, 1H), 8.37 (s, 1H), 8.59 (s, 2H), 9.12 (s, 1H), 9.30 (s, NH).

LRMS (m/z): 358 (M+1)$^+$.

Retention Time: 11 min.

Example 79

2-Ethyl-6-(5-methylpyridin-3-yl)-4-[(4-methylpyridin-3-yl)amino]pyridazin-3(2H)-one Obtained as a solid (67%) from the title compound of Preparation 81 and 3-bromo-4-methylpyridine following the experimental procedure described in Example 13.

δ(DMSO-$d_6$): 1.38 (t, 3H), 2.22 (s, 3H), 2.32 (s, 3H), 4.25 (q, 2H), 6.39 (s, 1H), 7.39 (d, 1H), 7.90 (s, 1H), 8.38 (d, 1H), 8.42 (s, 1H), 8.50 (s, 1H), 8.68 (d, 1H).

LRMS (m/z): 322 (M+1)$^+$.

Retention Time: 8 min.

Example 80

2-Ethyl-4-(1,7-naphthyridin-5-ylamino)-6-phenylpyridazin-3(2H)-one

Obtained as a solid (11%) from the title compound of Preparation 34 and 5-bromo-[1,7]naphthyridine (M. Wozniak and H. C. van der Plas, *J. Heterocyclic Chem.*, 15, 1978, 731-36) following the procedure of Example 13.

δ(DMSO-$d_6$): 1.38 (t, 3H), 4.24 (q, 2H), 7.23 (m, 2H), 7.32 (m, 3H), 7.75 (t, 1H), 7.85 (t, 1H), 7.99 (d, 1H), 8.19 (d, 1H), 8.31 (s, 1H), 9.24 (s, 1H), 9.44 (s, 1H).

m.p.: 215.9-216-6° C.

Example 81

[1-Ethyl-6-oxo-3-phenyl-5-(pyridin-3-ylamino)-1,6-dihydropyridazin-4-yl]methyl acetate Obtained as a solid (23%) from the title compound of Preparation 84 and pyridine-3-boronic acid following the experimental procedure described in Example 5.

m.p.: 144-145° C.

δ(CDCl3): 1.40 (t, 3H), 1.78 (s, 3H), 4.10 (q, 2H), 4.70 (s, 2H), 7.51 (m, 7H), 8.40-8.60 (m, 3H).

Example 82

[1-Ethyl-6-oxo-3-phenyl-5-(pyridin-3-ylamino)-1,6-dihydropyridazin-4-yl]methyl butyrate Obtained as a solid (15%) from the title compound of Preparation 85 and pyridine-3-boronic acid following the experimental procedure described in Example 5.

m.p.: 138-142° C.

δ(CDCl$_3$): 0.99 (t, 3H), 1.42 (t, 3H), 1.62-1.70 (m, 2H), 2.38 (t, 2H), 4.29 (q, 2H), 5.00 (s, 2H), 7.40-7.57 (m, 5H), 7.68 (s, 2H), 8.25 (t,1H), 8.40 (s,1H), 9.37 (s, 1H).

Example 83

2-Ethyl-5-[2-(4-methoxyphenyl)-1,3-thiazol-4-yl]-6-phenyl-4-(pyridin-3-ylamino)pyridazin-3(2H)-one A mixture of the title compound of Preparation 87 (0.25 g, 0.618 mmol), 3-bromopyridine (0.12 g, 0.74 mmol), copper (I)iodide (12 mg, 0.06 mmol), potassium carbonate (0.18 g, 1.30 mmol) and 1,1'-dimethylethilenediamine (0.013 mL, 0.12 mmol) in dioxane (2 mL) are heated at 125° C. in a sealed tube under nitrogen for 24 h. Once at room temperature, the inorganic salts are filtered and the solvent evaporated under reduced pressure. Purification of the residue through a flash chromatography column eluting with 1:9 hexane/ethyl acetate to 100% acetate, yields 110 mg of the desired final compound. (37% yield).

m.p.: 201.1-201.9° C.

$\delta$(DMSO-$d_6$): 1.4 (m, 3H), 4.32 (q, J=7.0 Hz, 2H), 4.8 (s, 3H), 6.80 (dd, J=8.0, 4.5 Hz, 1H), 6.95 (m, 3H), 7.10 (m, 1H), 7.15 (m, 2H), 7.2 (m, 3H), 7.42 (d, J=8.6 Hz, 2H), 7.81 (m, 1H), 8.15 (m, 1H), 8.97 (s, 1H).

Example 84

2-Ethyl-4-(isoquinolin-4-ylamino)-6-(6-methylpyridin-3-yl)pyridazin-3(2H)-one

Obtained as a solid (6%) from the title compound of Preparation 46 and 4-bromoisoquinoline following the procedure of Example 83.

$\delta$(CDCl$_3$): 1.45 (t, 3H), 2.58 (s, 3H), 4.40 (q, 2H), 6.62 (m, 1H), 7.20 (m, 1H), 7.80 (m, 4H), 8.05 (m, 1H), 8.10 (m, 1H), 8.65 (m, 2H), 9.22 (s,1H).

LRMS (m/z): 358 (M+1)$^+$.

Retention Time: 11 min.

Example 85

2-Ethyl-6-(6-methylpyridin-3-yl)-4-(pyridin-3-ylamino)pyridazin-3(2H)-one

Obtained as a solid (15%) from the title compound of Preparation 46 and 3-bromopyridine following the procedure of Example 83.

$\delta$(CDCl$_3$): 1.45 (t, 3H), 2.60 (s, 3H), 4.38 (q, 2H), 7.00 (s, 1H), 7.20 (m, 1H), 7.38 (m, 1H), 7.60 (m, 1H), 7.62 (s, 1H), 7.98 (m, 1H), 8.42 (m, 1H), 8.62 (s, 1H), 8.82 (s,1H).

LRMS (m/z): 308 (M+1)$^+$.

Retention Time: 7 min.

Example 86

2-Ethyl-5-[2-(4-methoxyphenyl)-1,3-thiazol-4-yl]-4-[(4-methylpyridin-3-yl)amino]-6-phenylpyridazin-3(2H)-one Obtained as a solid (29%) from the title compound of Preparation 87 and 3-bromo-4-methyl-pyridine following the procedure of Example 83.

m.p.: 210.3-211.1° C.

$\delta$(DMSO-d6): 1.40 (t, J=7.1 Hz, 3H), 2.18 (s, 3H) 3.80 (m, 3H), 4.25 (q, J=7.1 Hz, 2H), 6.75 (s, 1H), 6.90 (s, 1H), 7.00 (d, J=8.6 Hz, 2H), 7.18 (m, 5H), 7.55 (d, J=8.6 Hz, 2H), 7.80 (s, 1H), 7.90 (m, 1H), 8.57 (s, 1H).

Example 87

2-Ethyl-6-phenyl-4-(pyridin-3-ylamino)-5-(2-pyridin-4-yl-1,3-thiazol-yl)pyridazin-3(2H)-one Obtained as a solid (62%) from the title compound of preparation 88 and 3-bromopyridine following the procedure of Example 83.

m.p.: 207.2-208.0° C.

$\delta$(DMSO-$d_6$): 1.40 (t, 3H), 4.22 (q, 2H), 6.78 (m, 1H), 7.05 (m, 1H), 7.10 (m, 2H), 7.18 (m, 4H), 7.45 (d, 2H), 7.80 (m, 1H), 8.05 (m, 1H), 8.60 (d, 2H), 9.05 (s, 1H).

Example 88

Ethyl 4-[1-ethyl-6-oxo-3-phenyl-5-(pyridin-3-ylamino)-1,6-dihydropyridazin-4-yl]-1,3-thiazole-2-carboxylate Obtained as a solid (20%) from the title compound of the preparation 90 and the corresponding boronic acid following the procedure of Example 5.

m.p.: 165.9-167.4° C.

$\delta$(CDCl$_3$): 1.23 (t, 3H), 1.40 (t, 3H), 4.22 (m, 4H), 6.82 (s, 1H), 7.12 (m, 4H), 7.20 (m, 3H), 7.38 (s, 1H), 8.00 (bs, 1H), 9.00 (s, 1H).

Example 89

2-Ethyl-4-(isoquinolin-4-ylamino)-5-[2-(4-methoxyphenyl)-1,3-thiazol-4-yl]-6-phenylpyridazin-3(2H)-one Obtained as a solid (6%) from the title compound of preparation 87 and 4-bromoisoquinoline following the procedure of Example 83.

$\delta$(CDCl$_3$): 1.45 (t, 3H), 3.80 (m, 3H), 4.42 (q, 2H), 6.22 (s, 1H), 6.60 (d, 2H), 7.05 (d, 2H), 7.20 (m, 5H), 7.43 (m, 1H), 7.60 (m, 1H), 7.78 (m, 1H), 7.82 (m, 1H), 8.20 (m, 2H), 8.60 (s, 1H)

Example 90

2-Ethyl-4-[(4-methylpyridin-3-yl)amino]-6-phenyl-5-(2-pyridin-4-yl-1,3-thiazol-4-yl)pyridazin-3(2H)-one Obtained as a solid (18%) from the title compound of preparation 88 and 3-bromo-4-methyl-pyridine following the procedure of Example 83.

$\delta$(DMSO-$d_6$): 1.4 (t, J=7.3 Hz, 3H) 2.1 (s, 3H) 4.3 (q, J=7.3 Hz, 2H) 6.7 (d, J=4.6 Hz, 1H) 7.1 (m, 2H) 7.2 (m, 4H) 7.5 (m, 2H) 7.7 (d, J=5.0 Hz, 1H) 7.9 (s, 1H) 8.6 (m, 3H)

Example 91

5-[2-(4-Chlorophenyl)-1,3-thiazol-4-yl]-2-ethyl-4-[(4-methylpyridin-3-yl)amino]-6-phenylpyridazin-3(2H)-one Obtained as a solid (38%) from the title compound of preparation 89 and 3-bromo-4-methyl-pyridine following the procedure of Example 83.

$\delta$(DMSO-$d_6$): 1.40 (t, 3H), 2.18 (s, 3H), 4.22 (q, 2H), 6.78 (m, 1H), 7.05 (s, 1H), 7.16 (m, 5H), 7.45 (d, 2H), 7.60 (d, 2H), 7.78 (d, 1H), 7.90 (s, 1H), 8.60 (s,1H).

Example 92

5-[2-(4-Chlorophenyl)-1,3-thiazol-4-yl]-2-ethyl-6-phenyl-4-pyridin-3-ylamino)pyridazin-3(2H)-one Obtained as a solid (30%) from the title compound of preparation 89 and 3-bromopyridine following the procedure of Example 83.

LRMS (m/z): 486 (M+1)$^+$.

Retention Time: 9.67 min*.

* Chromatographic method B

Example 93

5-[2-(4-Chlorophenyl)-1,3-thiazol-4-yl]-2-ethyl-4-(isoquinolin-4-ylamino)-6-phenylpyridazin-3(2H)-one Obtained as a solid (2%) from the title compound of preparation 89 and 4-bromoisoquinoline following the procedure of Example 83.

δ(CDCl$_3$): 1.45 (t, 3H), 4.42 (q, 2H), 6.38 (s, 1H), 6.95 (d, 2H), 7.10 (d, 2H), 7.25 (m, 6H), 7.45 (m, 1H), 7.60 (m, 1H), 7.65 (m, 2H), 8.20 (m, 2H).

Example 94

2-Ethyl-4-[(4-methylpyridin-3-yl)amino]-6-phenylpyridazin-3(2H)-one

Obtained as a solid (47%) from the title compound of Preparation 34 and the corresponding bromide following the procedure of Example 13.

LRMS: m/Z 307 (M+1)$^+$.

δ(DMSO-d$_6$): 1.38 (t, 3H), 2.22 (s, 3H), 4.23 (q, 2H), 6.31 (s, 1H), 7.40 (m, 4H), 7.68 (m, 2H), 8.37 (d, 1H), 8.49 (s, 1H), 8.64 (s, 1H).

Example 95

2-Ethyl-4-[(4-methyl-1-oxidopyridin-3-yl)amino]-6-phenylpyridazin-3(2H)-one

Obtained as a solid (64%) from the title compound of Example 94 using the experimental procedure described in Example 33.

LRMS: m/Z 323 (M+1)$^+$.

δ(DMSO-d$_6$): 1.37 (t, 3H), 2.14 (s, 3H), 4.22 (q, 2H), 6.54 (s, 1H), 7.36 (d, 1H), 7.42 (m, 3H), 7.76 (m, 2H), 7.90 (d, 1H), 8.20 (s, 1H), 8.62 (s, 1H).

Example 96

Ethyl 4-[(2-ethyl-3-oxo-6-phenyl-2,3-dihydropyridazin-4-yl)amino]benzoate

Obtained as a solid (57%) from the title compound of Preparation 34 and the corresponding boronic acid following the procedure of Example 5.

LRMS: m/Z 364 (M+1)$^+$.

δ(CDCl3): 1.30 (t, 3H), 1.50 (t, 3H), 4.30 (dq, 4H), 7.25 (m, 3H), 7.40 (m, 3H), 7.70 (m, 2H), 7.90 (s, 1H), 8.10 (m, 2H).

The following examples illustrate pharmaceutical compositions according to the present invention.

COMPOSITION EXAMPLES

Composition Example 1

| Preparation of tablets | |
|---|---|
| Formulation: | |
| Compound of the present invention | 5.0 mg |
| Lactose | 113.6 mg |
| Microcrystalline cellulose | 28.4 mg |
| Light silicic anhydride | 1.5 mg |
| Magnesium stearate | 1.5 mg |

Using a mixer machine, 15 g of the compound of the present invention are mixed with 340.8 g of lactose and 85.2 g of microcrystalline cellulose. The mixture is subjected to compression moulding using a roller compactor to give a flake-like compressed material. The flake-like compressed material is pulverized using a hammer mill, and the pulverized material is screened through a 20 mesh screen. A 4.5 g portion of light silicic anhydride and 4.5 g of magnesium stearate are added to the screened material and mixed. The mixed product is subjected to a tablet making machine equipped with a die/punch system of 7.5 mm in diameter, thereby obtaining 3,000 tablets each having 150 mg in weight.

Composition Example 2

| Preparation of coated tablets | |
|---|---|
| Formulation: | |
| Compound of the present invention | 5.0 mg |
| Lactose | 95.2 mg |
| Corn starch | 40.8 mg |
| Polyvinylpyrrolidone K25 | 7.5 mg |
| Magnesium stearate | 1.5 mg |
| Hydroxypropylcellulose | 2.3 mg |
| Polyethylene glycol 6000 | 0.4 mg |
| Titanium dioxide | 1.1 mg |
| Purified talc | 0.7 mg |

Using a fluidised bed granulating machine, 15 g of the compound of the present invention are mixed with 285.6 g of lactose and 122.4 g of corn starch. Separately, 22.5 g of polyvinylpyrrolidone is dissolved in 127.5 g of water to prepare a binding solution. Using a fluidised bed granulating machine, the binding solution is sprayed on the above mixture to give granulates. A 4.5 g portion of magnesium stearate is added to the obtained granulates and mixed. The obtained mixture is subjected to a tablet making machine equipped with a die/punch biconcave system of 6.5 mm in diameter, thereby obtaining 3,000 tablets, each having 150 mg in weight.

Separately, a coating solution is prepared by suspending 6.9 g of hydroxypropylmethyl-cellulose 2910, 1.2 g of polyethylene glycol 6000, 3.3 g of titanium dioxide and 2.1 g of purified talc in 72.6 g of water. Using a High Coated, the 3,000 tablets prepared above are coated with the coating solution to give film-coated tablets, each having 154.5 mg in weight.

Composition Example 3

Preparation of capsules

Formulation:

| | |
|---|---|
| Compound of the present invention | 5.0 mg |
| Lactose monohydrate | 200 mg |
| Colloidal silicon dioxide | 2 mg |
| Corn starch | 20 mg |
| Magnesium stearate | 4 mg |

25 g of active compound, 1 Kg of lactose monohydrate, 10 g of colloidal silicon dioxide, 100 g of corn starch and 20 g of magnesium stearate are mixed. The mixture is sieved through a 60 mesh sieve, and then filled into 5,000 gelatine capsules.

Composition Example 4

Preparation of a cream

Formulation:

| | |
|---|---|
| Compound of the present invention | 1% |
| Cetyl alcohol | 3% |
| Stearyl alcohol | 4% |
| Gliceryl monostearate | 4% |
| Sorbitan monostearate | 0.8% |
| Sorbitan monostearate POE | 0.8% |
| Liquid vaseline | 5% |
| Methylparaben | 0.18% |
| Propylparaben | 0.02% |
| Glycerine | 15% |
| Purified water csp. | 100% |

An oil-in-water emulsion cream is prepared with the ingredients listed above, using conventional methods.

The invention claimed is:
1. A pyridazinone derivative of formula (I)

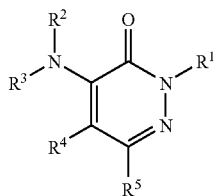

(I)

wherein
$R^1$ represents:
a hydrogen atom;
a group chosen from acyl, alkoxycarbonyl, carbamoyl, monoalkylcarbamoyl and dialkylcarbamoyl;
an alkyl, alkenyl or alkynyl group, wherein the alkyl, alkenyl or alkynyl group is optionally substituted by one or more substituents chosen from halogen atoms, hydroxy, alkoxy, aryloxy, alkylthio, arylthio, oxo, amino, mono- and di-alkylamino, acylamino, hydroxycarbonyl, alkoxycarbonyl, carbamoyl and mono- and di-alkylcarbamoyl groups;
an aryl or heteroaryl group, wherein the aryl or heteroaryl group is optionally substituted by one or more substituents chosen from halogen atoms, hydroxy, hydroxyalkyl, hydroxycarbonyl, alkoxy, alkylenedioxy, alkoxycarbonyl, aryloxy, acyl, acyloxy, alkylthio, arylthio, amino, nitro, cyano, mono- and di-alkylamino, acylamino, carbamoyl, mono- and di-alkylcarbamoyl, difluoromethyl, trifluoromethyl, difluoromethoxy, and trifluoromethoxy groups;
a saturated or unsaturated heterocyclic group, wherein the saturated or unsaturated heterocyclic group is optionally substituted by one or more substituents chosen from halogen atoms, hydroxy, hydroxyalkyl, hydroxycarbonyl, alkoxy, alkylenedioxy, alkoxycarbonyl, aryloxy, acyl, acyloxy, alkylthio, arylthio, oxo, amino, nitro, cyano, mono- and di-alkylamino, acylamino, carbamoyl, mono- and di-alkylcarbamoyl, difluoromethyl, trifluoromethyl, difluoromethoxy, and trifluoromethoxy groups; or
a group of formula —$(CH_2)_n$—$R^6$ wherein n is an integer from 0 to 4 and $R^6$ represents:
a cycloalkyl or cycloalkenyl group;
an aryl group, which is optionally substituted by one or more substituents chosen from halogen atoms, alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy, and trifluoromethoxy groups;
or a 3- to 7-membered ring comprising from 1 to 4 heteroatoms chosen from nitrogen, oxygen and sulphur, which ring is optionally substituted by one or more substituents chosen from halogen atoms, alkyl, hydroxy, alkoxy, alkylenedioxy, amino, mono- and di-alkylamino, nitro, cyano and trifluoromethyl groups;
$R^2$ represents:
a hydrogen atom;
a group chosen from acyl, alkoxycarbonyl, carbamoyl, monoalkylcarbamoyl and dialkylcarbamoyl;
an alkyl, alkenyl or alkynyl group, wherein the alkyl, alkenyl or alkynyl group is optionally substituted by one or more substituents chosen from halogen atoms, hydroxy, alkoxy, hydroxycarbonyl, alkoxycarbonyl, aryloxy, alkylthio, arylthio, oxo, amino, mono- and di-alkylamino, acylamino, carbamoyl, and mono- and di-alkylcarbamoyl groups;
an aryl or heteroaryl group, wherein the aryl or heteroaryl group is optionally substituted by one or more substituents chosen from halogen atoms, hydroxy, hydroxyalkyl, hydroxycarbonyl, alkoxy, alkylenedioxy, alkoxycarbonyl, aryloxy, acyl, acyloxy, alkylthio, arylthio, amino, nitro, cyano, mono- and di-alkylamino, acylamino, carbamoyl, mono- and di-alkylcarbamoyl, difluoromethyl, trifluoromethyl, difluoromethoxy, and trifluoromethoxy groups;
a saturated or unsaturated heterocyclic group, wherein the saturated or unsaturated heterocyclic group is optionally substituted by one or more substituents chosen from halogen atoms, hydroxy, hydroxyalkyl, hydroxycarbonyl, alkoxy, alkylenedioxy, alkoxycarbonyl, aryloxy, acyl, acyloxy, alkylthio, arylthio, oxo, amino, nitro, cyano, mono- and di-alkylamino, acylamino, carbamoyl, mono- and di-alkylcarbamoyl, difluoromethyl, trifluoromethyl, difluoromethoxy and trifluoromethoxy groups; or a group of formula

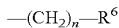

—(CH$_2$)$_n$—R$^6$ wherein n is an integer from 0 to 4 and R$^6$ represents:
a cycloalkyl or cycloalkenyl group;
an aryl group, which is optionally substituted by one or more substituents chosen from halogen atoms and alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy, and trifluoromethoxy groups;
or a 3- to 7-membered ring comprising from 1 to 4 heteroatoms chosen from nitrogen, oxygen and sulphur, which ring is optionally substituted by one or more substituents chosen from halogen atoms, alkyl, hydroxy, alkoxy, alkylenedioxy, amino, mono- and di-alkylamino, nitro, cyano, and trifluoromethyl groups;

R$^3$ represents a monocyclic or polycyclic aryl or a monocyclic or polycyclic heteroaryl group, wherein the monocyclic or polycyclic aryl or the monocyclic or polycyclic heteroaryl group are optionally substituted by one or more substituents chosen from:
halogen atoms;
alkyl and alkylene groups, wherein the alkyl and alkylene groups are optionally substituted by one or more substituents chosen from halogen atoms, phenyl, hydroxy, alkoxy, aryloxy, alkylthio, arylthio, oxo, amino, mono- and di-alkylamino, acylamino, hydroxycarbonyl, alkoxycarbonyl, carbamoyl, and mono- and di-alkylcarbamoyl groups; and
phenyl, hydroxy, hydroxyalkyl, alkoxy, cycloalkoxy, nitro, cyano, aryloxy, alkylthio, arylthio, alkylsulfinyl, alkylsulfonyl, alkylsulfamoyl, acyl, amino, mono- and di-alkylamino, acylamino, hydroxycarbonyl, alkoxycarbonyl, carbamoyl, mono- and di-alkylcarbamoyl, ureido, N'-alkylureido, N', N'-dialkylureido, alkylsulfamido, aminosulfonyl, mono- and di-alkylaminosulfonyl, difluoromethoxy, and trifluoromethoxy groups;

R$^4$ represents:
a hydrogen atom;
a hydroxy, alkoxy, amino, monoalkylamino, dialkylamino or cyano group;
an alkyl, alkenyl or alkynyl group, wherein the alkyl, alkenyl or alkynyl group is optionally substituted by one or more substituents chosen from halogen atoms, hydroxy, acyloxy, alkoxy, aryloxy, alkylthio, arylthio, amino, mono- and di-alkylamino, acylamino, hydroxycarbonyl, alkoxycarbonyl, alkoxyimino, carbamoyl, and mono- and di-alkylcarbamoyl groups;
or a group of formula

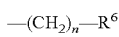

—(CH$_2$)$_n$—R$^6$ wherein n is an integer from 0 to 4 and R$^6$ represents:
a cycloalkyl or cycloalkenyl group;
an aryl group, which is optionally substituted by one or more substituents chosen from halogen atoms, alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy, and trifluoromethoxy groups;
or a 3- to 7-membered ring comprising from 1 to 4 heteroatoms chosen from nitrogen, oxygen and sulphur, which ring is optionally substituted by one or more substituents chosen from halogen atoms, alkyl, phenyl, alkoxyphenyl, halophenyl, pyridyl, alkoxycarbonyl, hydroxy, alkoxy, alkylenedioxy, amino, mono- and di-alkylamino, nitro, cyano, and trifluoromethyl groups;

R$^5$ represents a group —COOR$^7$ or a monocyclic or polycyclic aryl or a monocyclic or polycyclic heteroaryl group, wherein the monocyclic or polycyclic aryl or the monocyclic or polycyclic heteroaryl group are optionally substituted by one or more substituents chosen from:
halogen atoms;
alkyl and alkenyl groups, wherein the alkyl and alkenyl groups are optionally substituted by one or more substituents chosen from halogen atoms, phenyl, hydroxy, hydroxyalkyl, alkoxy, aryloxy, alkylthio, arylthio, oxo, amino, mono- and di-alkylamino, acylamino, hydroxycarbonyl, alkoxycarbonyl, carbamoyl, mono- and di-alkylcarbamoyl groups; and
phenyl, hydroxy, alkylenedioxy, alkoxy, cycloalkyloxy, alkylthio, alkylsulfinyl, alkylsulfonyl, alkylsulfamoyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulfamido, aminosulfonyl, mono- and di-alkylaminosulfonyl, cyano, difluoromethoxy, and trifluoromethoxy groups;
wherein R$^7$ represents
an alkyl, which is optionally substituted by one or more substituents chosen from halogen atoms, hydroxy, alkoxy, aryloxy, alkylthio, arylthio, oxo, amino, mono- and di-alkylamino, acylamino, hydroxycarbonyl, alkoxycarbonyl, carbamoyl, and mono- and di-alkylcarbamoyl groups,
or a group of formula

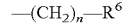

—(CH$_2$)$_n$—R$^6$ wherein n is an integer from 0 to 4 and R$^6$ represents:
a cycloalkyl or cycloalkenyl group;
an aryl group, which is optionally substituted by one or mote substituents chosen from halogen atoms, alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy, and trifluoromethoxy groups;
or a 3- to 7-membered ring comprising from 1 to 4 heteroatoms chosen from nitrogen, oxygen and sulphur, which ring is optionally substituted by one or more substituents chosen from halogen atoms, alkyl, phenyl, alkoxyphenyl, halophenyl, pyridyl, alkoxycarbonyl, hydroxy, alkoxy, alkylenedioxy, amino, mono- and di-alkylamino, nitro, cyano, and trifluoromethyl groups;

or a salt thereof, or a N-oxide thereof
with the proviso that when R$^1$ is methyl, R$^2$ is H, and both R$^3$ and R$^5$ are phenyl then R$^4$ is not a 1-hydroxyethyl group.

2. A compound according to claim 1, wherein R$^1$ is chosen from hydrogen atoms and alkyl groups, wherein the alkyl groups are optionally substituted by one or more substituents chosen from halogen atoms, hydroxy, alkoxy, alkylthio, hydroxycarbonyl and alkoxycarbonyl groups.

3. A compound according to claim 2 wherein R$^1$ is chosen from unsubstituted C$_{1-4}$ alkyl groups.

4. A compound according to claim 1, wherein R$^2$ is chosen from:
hydrogen atoms,
an acyl group, an alkyl group, which is optionally substituted by one or more substituents chosen from halogen atoms, hydroxy, alkoxy, and alkylthio groups; and aryl and heteroaryl groups, wherein the aryl and heteroaryl groups are optionally substituted by one or more substituents chosen from halogen atoms, hydroxy, hydroxyalkyl, hydroxycarbonyl, alkoxy, alkylenedioxy, alkoxycarbonyl, aryloxy, acyl, acyloxy, alkylthio, arylthio, amino, nitro, cyano, mono- and di-alkylamino, acyiamino, carbamoyl, mono- and di-alkylcarbamoyl, difluoromethyl, trifluoromethyl, difluoromethoxy, and trifluoromethoxy groups.

5. A compound according to claim 4 wherein $R^2$ is a hydrogen atom.

6. A compound according to claim 1, wherein $R^3$ represents a monocyclic or polycyclic aryl or a monocyctic or polycyclic heteroaryl group, wherein the monocyclic or polycyclic, aryl or the monocyclic or polycyclic heteroaryl group are optionally substituted by one or more substituents chosen from:
halogen atoms;
alkyl and alkylene groups, wherein the alkyl and alkylene groups are optionally substituted by one or more substituents chosen from halogen atoms, phenyl, hydroxy, alkoxy, aryloxy, alkylthio, arylthio, oxo, amino, mono- or di-alkylamino, acylamino, hydroxycarbonyl, alkoxycarbonyl, carbamoyl and mono- and di-alkylcarbamoyl groups; and
phenyl, hydroxy, hydroxyalkyl, alkoxycarbonyl, alkoxy, cycloalkoxy, nitro, cyano, aryloxy, alkylthio, arylthio, alkylsuifinyl, alkylsulfonyl, alkylsulfamoyl, acyl, amino, mono- and di-alkylamino, acylamino, hydroxycarbonyl, carbamoyl, mono- and di-alkylcarbamoyl, ureido, N'-alkylureido, N',N'-dialkylureido, alkylsulfamido, aminosulfonyl, mono- and di-alkylaminosulfonyl, difluoromethoxy, and trifluoromethoxy groups.

7. A compound according to claim 6, wherein $R^3$ represents a monocyclic or polycyclic aryl or a monocyclic or polycyclic heteroaryl group, wherein the monocyclic or polycyclic, aryl or the monocyclic or polycyclic heteroaryl group are optionally substituted by one substituent chosen from halogen atoms, alkyl groups and hydroxycarbonyl groups.

8. A compound according to claim 7, wherein $R^3$ represents a phenyl group or a monocyclic or polycyclic N-containing heteroaryl group, wherein the phenyl group or the monocyclic or polycyclic N-containing heteroaryl group may be substituted by one substituent chosen from halogen atoms, alkyl groups and hydroxycarbonyl groups.

9. A compound according to claim 1, wherein $R^4$ represents:
a hydrogen atom;
a cyano group;
an alkyl, alkenyl or alkynyl group, wherein the alkyl, alkenyl or alkynyl group is optionally substituted by one or more substituents chosen from halogen atoms, hydroxy, acyloxy, alkoxy, aryloxy, alkylthio, arylthio, amino, mono- and di-alkylamino, acylamino, hydroxycarbonyl, alkoxycarbonyl, carbamoyl, and mono- and di-alkylcarbamoyl groups;
or a group of formula —(CH$_2$)$_n$—R$^6$ wherein n is an integer from 0 to 4 and $R^6$ represents a 3- to 7-membered ring comprising from 1 to 4 heteroatoms chosen from nitrogen, oxygen and sulphur, which ring is optionally substituted by one or more substituents chosen from halogen atoms, alkyl, phenyl, alkoxyphenyl, halophenyl, pyridyl, alkoxycarbonyl, hydroxy, alkoxy, alkylenedioxy, amino, mono- and di-alkylamino, nitro, cyano, and trifluoromethyl groups.

10. A compound according to claim 9 wherein $R^4$ represents a hydrogen atom or a cyano group.

11. A compound according to claim 1, wherein $R^5$ represents a group —COOR$^7$, a monocyclic or polycyclic aryl or a monocyclic or polycyclic heteroaryl group, wherein the monocyclic or polycyclic aryl or the monocyclic or polycyclic heteroaryl group are optionally substituted by one or more substituents chosen from:
halogen atoms;
alkyl groups, which are optionally substituted by one or more substituents chosen from halogen atoms, hydroxy, hydroxyalkyl, alkoxy, alkylthio, mono- or di-alkylamino, acylamino, hydroxycarbonyl, alkoxycarbonyl, carbamoyl, and mono- and di-alkylcarbamoyl groups; and
hydroxy, alkylenedioxy, alkoxy, cycloalkyloxy, alkylthio, alkylsulfinyl, alkylsulfonyl, alkylsulfamoyl, amino, mono- and di-alkylamino, acylamino, nitro, acyl, hydroxycarbonyl, alkoxycarbonyl, carbamoyl, mono- and di-alkylcarbamoyl, ureido, N'-alkylureido, N',N'-dialkylureido, alkylsulfamido, aminosuphonyl, mono- and di-alkylaminosulfonyl, cyano, difluoromethoxy, and trifluoromethoxy groups;
wherein $R^7$ represents
an alkyl group, which is optionally substituted by one or more substituents chosen from halogen atoms, hydroxy, alkoxy, aryloxy, alkylthio, arylthio, oxo, amino, mono- and di-alkylamino, acylamino, hydroxycarbonyl, alkoxycarbonyl, carbamoyl, and mono- and di-alkylcarbamoyl groups
or a group of formula —(CH$_2$)$_n$—R$^6$ wherein n Is an integer from 0 to 4 and $R^6$ represents:
a cycloalkyl or cycloalkenyl group;
an aryl group, which is optionally substituted by one or more substituents chosen from halogen atoms, alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluorornethyl, difluoromethoxy, and trifluoromethoxy groups;
or a 3- to 7-membered ring comprising from 1 to 4 heteroatoms chosen from nitrogen, oxygen and sulphur, which ring is optionally substituted by one or more substituents chosen from halogen atoms, alkyl, phenyl, hydroxy, alkoxy, alkylenedioxy, amino, mono- and di-alkylamino, nitro, cyano, and trifluoromethyl groups.

12. A compound according to claim 11, wherein $R^5$ represents a monocyclic aryl or heteroaryl group, wherein the monocyclic aryl or heteroaryl group is optionally substituted by one or more substituents chosen from halogen atoms and alkyl groups.

13. A compound according to claim 1, wherein $R^1$ is chosen from hydrogen atoms and alkyl groups, which are optionally substituted by one or more substituents chosen from halogen atoms, hydroxy, alkoxy, alkylthio, arylthio, hydroxycarbonyl and alkoxycarbonyl groups; and
$R^2$ is chosen from:
hydrogen atoms,
an acyl group
an alkyl group, which is optionally substituted by one or more substituents chosen from halogen atoms, hydroxy, alkoxy and alkylthio groups; and aryl and heteroaryl groups, wherein the aryl and heteroaryl groups are optionally substituted by one or more halogen atoms.

14. A compound according to claim 13, wherein $R^1$ is chosen from unsubstituted $C_{1-4}$ alkyl groups and $R^2$ is a hydrogen atom.

15. A compound according to claim 14, wherein $R^3$ represents a monocyclic or polycyclic aryl or a monocyclic or polycyclic heteroaryl group, wherein the monocyclic or polycyclic aryl or the monocyclic or polycyclic heteroaryl group are optionally substituted by one or more substituents chosen from:
halogen atoms;
alkyl groups, which are optionally substituted by one or more substituents chosen from halogen atoms and hydroxy groups; and
cyano, and hydroxycarbonyl groups.

16. A compound according to claim 15, wherein $R^3$ represents a phenyl group or a monocyclic or polycyclic N-containing heteroaryl group, wherein the phenyl group or the monocyclic or polycyclic N-containing heteroaryl group may be substituted by one substituent chosen from halogen atoms, alkyl groups and hydroxycarbonyl groups.

17. A compound according to claim 13, wherein $R^4$ represents:
a hydrogen atom;
a cyano group;
an alkyl, alkenyl or alkynyl group, wherein the alkyl, alkenyl or alkynyl group is optionally substituted by one or more substituents chosen from halogen atoms, hydroxyl and alkoxy groups;
or a group of formula —(CH$_2$)$_n$—R$^6$ wherein n is 0 and $R^6$ represents a 3- to 7-membered ring comprising from 1 to 4 heteroatoms chosen from nitrogen, oxygen and sulphur, which ring is optionally substituted by one or more substituents chosen from halogen atoms, alkyl and phenyl groups.

18. A compound according to claim 17 wherein $R^4$ represents a hydrogen atom or a cyano group.

19. A compound according to claim 13, wherein $R^5$ represents a group —COOR$^7$, a monocyclic or polycyclic aryl or a monocyclic or polycyclic heteroaryl group, wherein the monocyclic or polycyclic aryl or the monocyclic or polycyclic heteroaryl group are optionally substituted by one or more substituents chosen from:
halogen atoms;
alkyl groups, which are optionally substituted by one or more substituents chosen from halogen atoms, hydroxyl and alkoxy groups; and
alkoxy, alkoxycarbonyl and hydroxycarbonyl groups;
wherein $R^7$ represents
an alkyl group, which is optionally substituted by one or more substituents chosen from halogen atoms, hydroxyl and alkoxy groups
or a group of formula —(CH$_2$)$_n$—R$^6$ wherein n is an integer from 0 to 4 and $R^6$ represents:
a cycloalkyl or cycloalkenyl group;
an aryl group, which is optionally substituted by one or more substituents chosen from halogen atoms, alkyl, hydroxy, alkoxy, alkylenedioxy, alkylthio, amino, mono- and di-alkylamino, nitro, acyl, hydroxycarbonyl, alkoxycarbonyl, carbamoyl, mono- and di-alkylcarbamoyl, cyano, trifluoromethyl, difluoromethoxy and trifluoromethoxy groups;
or a 3- to 7-membered ring comprising from 1 to 4 heteroatoms chosen from nitrogen, oxygen and sulphur, which ring is optionally substituted by one or more substituents chosen from halogen atoms, alkyl, phenyl, hydroxy, alkoxy, alkylenedioxy, amino, mono- and di-alkylamino, nitro, cyano and trifluoromethyl groups.

20. A compound according to claim 19, wherein $R^5$ represents a monocyclic or polycyclic aryl or a monocyclic or polycyclic heteroaryl group, wherein the monocyclic or polycyclic aryl or the monocyclic or polycyclic heteroaryl group are optionally substituted by one or more substituents chosen from:
halogen atoms;
alkyl groups, which are optionally substituted by one or more substituents chosen from halogen atoms, hydroxyl and alkoxy groups; and
alkoxy groups.

21. A compound according to claim 20, wherein $R^5$ represents a monocyclic aryl or heteroaryl group, which is optionally substituted by one or more substituents chosen from halogen atoms and alkyl groups.

22. A compound according to claim 1, wherein $R^1$ represents an alkyl group, $R^2$ represents a hydrogen atom or a group chosen from acyl, alkyl, aryl and heteroaryl groups, wherein the acyl, alkyl, aryl and heteroaryl groups are optionally substituted by one or more halogen atoms, $R^3$ represents a monocyclic or polycyclic aryl or a monocyclic or polycyclic heteroaryl group, wherein the monocyclic or polycyclic aryl or the monocyclic or polycyclic heteroaryl group are optionally substituted by one or more substituents chosen from halogen atoms, cyano, hydroxycarbonyl and alkyl groups, which are optionally substituted by one or more hydroxy groups, $R^4$ represents a hydrogen atom, a cyano group, an alkyl or alkenyl group, wherein the alkyl or alkenyl groups are optionally substituted by one substituent chosen from hydroxyl and alkoxy groups or $R^4$ represents a group of formula (—R$^6$) wherein $R^6$ represents a 4- to 6-membered ring comprising from 1 to 3 heteroatoms chosen from nitrogen, oxygen and sulphur, which ring is optionally substituted by one substituent chosen from alkyl and phenyl groups and $R^5$ represents a monocyclic aryl or monocyclic heteroaryl group, wherein the monocyclic aryl or the monocyclic heteroaryl group are optionally substituted by one substituent chosen from halogen atoms, alkyl and alkoxy groups.

23. A compound according to claim 1, wherein $R^1$ is chosen from unsubstituted $C_{1-4}$ alkyl groups; $R^2$ is a hydrogen atom; $R^3$ represents a phenyl group or a monocyclic or polycyclic N-containing heteroaryl group, wherein the phenyl group or the monocyclic or polycyclic N-containing heteroaryl group may be substituted by one substituent chosen from halogen atoms, alkyl groups and hydroxycarbonyl groups; $R^4$ represents a hydrogen atom or a cyano group and $R^5$ represents a monocyclic aryl or monocyclic heteroaryl group, wherein the monocyclic aryl or the monocyclic heteroaryl group are optionally substituted by one or more substituents chosen from halogen atoms and alkyl groups.

24. A compound according to claim 1, chosen from:
4-[(3-chlorophenyl)amino]-2-ethyl-5-(1-hydroxyethyl)-6-phenylpyridazin-3(2H)-one
4-[(3-chlorophenyl )amino]-2-ethyl-5-(1-methoxyethyl)-6-phenylpyridazin-3(2H)-one
4-[(3-chlorophenyl)amino]-2-ethyl-6-phenyl-5-vinylpyridazin-3(2H)-one
4-anilino-2,5-diethyl-6-phenylpyridazin-3(2H)-one 5-[(3-chlorophenyl)amino]-1-ethyl-6-oxo-3-phenyl-1,6-dihydropyridazine-4-carbaldehyde O-methyloxime
5-[(3-chlorophenyl)amino]-1-ethyl-6-oxo-3-phenyl-1,6-dihydropyridazine-4-carbonitrile
1-ethyl-5-{[4-(hydroxymethyl)phenyl]amino}-6-oxo-3-phenyl-1,6-dihydropyridazine-4-carbonitrile
1-ethyl-6-oxo-3-phenyl-5-[(3,4,5-trifluorophenyl)amino]-1,6-dihydropyridazine-4-carbonitrile
5-[(4-cyanophenyl)amino]-1-ethyl-6-oxo-3-phenyl-1,6-dihydropyridazine-4-carbonitrile
1-ethyl-3-(4-fluorophenyl)-5-{[4-(hydroxymethyl)phenyl]amino}-6-oxo-1,6-dihydropyridazine-4-carbonitrile
5-[(4-cyanophenyl)amino]-1-ethyl-3-(4-fluorophenyl)-6-oxo-1,6-dihydropyridazine-4-carbonitrile
1-ethyl-3-(4-fluorophenyl)-6-oxo-5-[(3,4,5-trifluorophenyl)amino]-1,6-dihydropyridazine-4-carbonitrile
1-ethyl-3-(4-fluorophenyl)-6-oxo-5-(pyridin-3-ylamino)-1,6-dihydropyridazine-4-carbonitrile
1-ethyl-3-(3-fluorophenyl)-5-{[4-(hydroxymethyl)phenyl]amino}-6-oxo-1,6-dihydropyridazine-4-carbonitrile
5-[(4-cyanophenyl)amino]-1-ethyl-3-(3-fluorophenyl)-6-oxo-1,6-dihydropyridazine-4-carbonitrile
1-ethyl-3-(3-fluorophenyl)-6-oxo-5-[(3,4,5-trifluorophenyl)amino]-1,6-dihydropyridazine-4-carbonitrile
4-[(3-chlorophenyl)amino]-2-ethyl-5-(2-methyl-1,3-thiazol-4-yl)-6-phenylpyridazin-3(2H)-one
4-[(3-chlorophenyl)amino]-2-ethyl-6-phenyl-5-(2-phenyl-1,3-thiazol-4-yl)pyridazin-3(2H)-one
4-[(3-chlorophenyl)amino]-2-ethyl-5-(1-methyl-1H-pyrazol-5-yl)-6-phenylpyddazin-3(2H)-one
4-{[2-ethyl-5-(5-methyl-1,3,4-oxadiazol-2-yl)-3-oxo-6-phenyl-2,3-dlhydropyridazin-4-yl]amino}benzonltrile
2-ethyl-5-(5-methyl-1,3,4-oxadiazol-2-yl)-6-phenyl-4-[(3,4,5-trifluorophenyl) amino]pyridazin-3(2H)-one
4-[(3-chlorophenyl)amino]-2-ethyl-6-phenylpyridazin-3(2H)-one
2-ethyl-4-[(3-fluorophenyl)amino]-6-phenylpyridazin-3(2H)-one
2-ethyl-4-(1-naphthylamino)-6-phenylpyridazin-3(2H)-one
2-ethyl-6-phenyl-4-(pyridin-3-ylamino)pyridazin-3(2H)-one
2-ethyl-6-phenyl-4-(quinolin-5-ylamino)pyridazin-3(2H)-one
4-(diquinolin-5-ylamino)-2-ethyl-6-phenylpyridazin-3(2H)-one
4-[bis(3,4,5-trifluorophenyl)amino]-2-ethyl-6-phenylpyridazin-3(2H)-one
4-[bis(3,4-difluorophenyl)amino]-2-ethyl-6-phenylpyridazin-3(2H)-one
4-[(3,4-difluorophenyl)amino]-2-ethyl-6-phenylpyridazin-3(2H)-one
4-[(3-chloro-4-fluorophenyl)amino]-2-ethyl-6-phenylpyridazin-3(2H)-one
4-[(2-ethyl-3-oxo-6-phenyl-2,3-dihydropyridazin-4-yl)amino]benzonitrile
2-ethyl-4-[(1-oxidopyridin-3-yl)amino]-6-phenylpyridazin-3(2H)-one
2-ethyl-6-pyridin-3-yl-4-(pyridin-3-ylamino)pyridazin-3(2H)-one
2-ethyl-4-[(1-oxidoquinolin-5-yl)amino]-6-phenylpyridazin-3(2H)-one
2-ethyl-6-pyridin-4-yl-4-(pyridin-3-ylamino)pyridazin-3(2H)-one
2-ethyl-4-(isoquinolin-4-ylamino)-6-phenylpyridazin-3(2H)-one
2-ethyl-6-phenyl-4-[(3,4,5-trifluorophenyl)amino]pyridazin-3(2H)-one
2-ethyl-4-[(4-fluorophenyl)amina]-6-phenylpyridazin-3(2H)-one
2-ethyl-6-pyridin-3-yl-4-(quinolin-5-ylamino)pyridazin-3(2H)-one
2-methyl-6-pyridin-3-yl-4-(quinolin-5-ylamino)pyridazin-3(2H)-one
2-ethyl-6-pyridin-4-yl-4-(quinolin-5-ylamino)pyridazin-3(2H)-one
2-ethyl-4-{[4-(hydroxymethyl)phenyl]amino}-6-phenylpyridazin-3(2H)-one
4-[(2-methyl-3-oxo-6-pyridin-3-yl-2,3-dihydropyridazin-4-yl)amino]benzonitrile
4-[(2-ethyl-3-oxo-6-pyridin-3-yl-2,3-dihydropyridazin-4-yl)amino]benzonitrile methyl 4-[(2-ethyl-3-oxo-6-phenyl-2,3-dihydropyridazin-4-yl)amino]benzoate
4-{[2-ethyl-6-(1-oxidopyridin-3-yl)-3-oxo-2,3-dihydropyridazin-4-yl]amino}benzonitrile
2-ethyl-4-(isoquinolin-4-ylamino)-6-pyridin-3-ylpyridazin-3(2H)-one
2-ethyl-4-[(4-methylpyridin-3-yl)amino]-6-pyridin-3-ylpyridazin-3(2H)-one
2-ethyl-4-(isoquinolin-4-ylamino)-6-pyridin-4-ylpyridazin-3(2H)-one
4-[(2-ethyl-3-oxo-6phenyl-2,3-dihydropyridazin-4-yl)amino]benzoic acid
2-ethyl-4-[(4-methylpyridin-3-yl)amino]-6-pyridin-4-ylpyridazin-3(2H)-one
4-[(2-ethyl-3-oxo-6-pyridin-4-yl-2,3-dihydropyridazin-4-yl)amino]benzonitrile
4-[(2-ethyl-3-oxo-6-phenyl-2,3-dihydropyridazin-4-yl)(methyl)amino]benzonitrile N-(4-cyanophenyl)-N-(2-ethyl-3-oxo-6-phenyl-2,3-dihydropyridazin-4-yl)acetamide
6-(3-chlorophenyl)-2-ethyl-4-(pyridin-3-ylamino)pyridazin-3(2H)-one
2-ethyl-4-[methyl(quinolin-5-yl)amino]-6-phenylpyridazin-3(2H)-one
6-(3-chlorophenyl)-2-ethyl-4-(isoquinolin-4-ylamino)pyridazin-3(2H)-one
N-(2-ethyl-3-oxo-6-phenyl-2,3-dihydropyridazin-4-yl)-N-quinolin-5-yl)acetamide
2-Ethyl-4-(4-hydroxymethyl-phenylamino)-6-pyridin-3-ylpyridazin-3(2H)-one
2-ethyl-4-(isoquinolin-4-ylamino)6-(4-methoxyphenyl)pyridazin-3(2H)-one
2-ethyl-6-(4-methoxyphenyl)-4-(quinolin-5-ylamino)pyridazin-3(2H)-one
4-anilino-2-ethyl-6-phenylpyridazin-3(2H)-one
2-ethyl-6-(4-methylphenyl)-4-(quinolin-5-ylamino)pyridazin-3(2H)-one
2-ethyl-6-(4-methylphenyl)-4-[(1-oxidoquinolin-5-yl)amino]pyridazin-3(2H)-one
2-Ethyl-6-phenyl-4-(thieno[2,3-c]pyridin-3-ylamino)pyridazin-3(2H)-one
1-Ethyl-6-oxo-3-phenyl-5-(pyridin-3-ylamino)-1,6-dihydropyridazine-4-carbonitrile
1-Ethyl-3-(3-methylphenyl)-6-oxo-5-(pyridin-3-ylamino)-1,6-dihydropyridazine-4-carbonitrile
2-Ethyl-5-(1-hydroxyethyl)-6-phenyl-4-(quinolin-5-ylamino)pyridazin-3(2H)-one
2-Ethyl-6-(4-methylphenyl)-4-(pyridin-3-ylamino)pyridazin-3(2H)-one 2-Ethyl-4-(isoquinolin-4-ylamino)-6-(4-methylphenyl)pyridazin-3(2H)-one
2-Ethyl-6-(4-methylphenyl)-4-[(4-methylpyridin-3-yl)amino]pyridazin-3(2H)-one
2-Ethyl-6-(3-methylphenyl)-4-(pyridin-3-ylamino)pyridazin-3(2H )-one
2-Ethyl-4-(isoquinolin-4-ylamino)-6-(3-methylphenyl)pyridazin-3(2H)-one
2-Ethyl-6-(3-methylphenyl)-4-[(4-methylpyridin-3-yl)amino]pyridazin-3(2H)-one
4-{[2-Ethyl-6-(3-methylphenyl)-3-oxo-2,3-dihydropyridazin-4-yl]amino}benzoic acid
2-Ethyl-6-(5-methylpyridin-3-yl)-4-(pyridin-3-ylamino)pyridazin-3(2H)-one
2-Ethyl-4-(isoquinolin-4-ylamino)-6-(5-methylpyridin-3-yl)pyridazin-3(2H)-one
2-Ethyl-6-(5-methylpyridin-3-yl)-4-[(4-methylpyridin-3-yl)amino]pyridazin-3(2H)-one
2-Ethyl-4-(1,7-naphthyridin-5-ylamino)-6-phenylpyridazin-3(2H)-one
[1-Ethyl-6-oxo-3-phenyl-5-(pyridin-3-ylamino)-1,6-dihydropyridazin-4-yl]methyl acetate
[1-Ethyl-6-oxo-3-phenyl-5-(pyridin-3-ylamino)-1,6-dihydropyridazin-4-yl]methyl butyrate
2-Ethyl-5-[2-(4-methoxyphenyl)-1,3-thiazol-4-yl]-6-phenyl-4-(pyridin-3-ylamino) pyridazin-3(2H)-one
2-Ethyl-4-(isoquinolin-4-ylamino)-6-(6-methylpyridin-3-yl)pyridazin-3(2H)-one
2-Ethyl-6-(6-methylpyridin-3-yl)-4-(pyridin-3-ylamino)pyridazin-3(2H)-one
2-Ethyl-5-[2-(4-methoxyphenyl)-1,3-thiazol-4-yl]-4-[(4-methylpyridin-3-yl)amino]-6-phenylpyridazin-3(2H)-one
2-Ethyl-6-phenyl-4-(pyridin-3-ylamino)-5-(2-pyridin-4-yl-1,3-thiazol-4-yl)pyridazin-3(2H)-one
Ethyl 4-[1-ethyl-6-oxo-3-phenyl-5-(pyridin-3-ylamino)-1,6-dihydropyridazin-4-yl]-1,3-thiazole-2-carboxylate
2-Ethyl-4-(isoquinolin-4-ylamino)-5-[2-(4-methoxyphenyl)-1,3-thiazol-4-yl]-6-phenylpyridazin-3(2H)-one
2-Ethyl-4-[(4-methylpyridin-3-yl)amino]-6-phenyl-5-(2-pyridin-4-yl-1,3-thiazol-4-yl) pyridazin-3(2H)-one
5-[2-(4-Chlorophenyl)-1,3-thiazol-4-yl]-2-ethyl-4-[(4-methylpyridin-3-yl)amino]-6-phenylpyridazin-3(2H)-one
5-[2-(4-Chlorophenyl)-1,3-thiazol-4-yl]-2-ethyl-6-phenyl-4-(pyridin-3-ylamino)pyridazin-3(2H)-one
5-[2-(4-Chlorophenyl)-1,3-thiazol-4-yl]-2-ethyl-4-(isoquinolin-4-ylamino)-6-phenylpyridazin-3(2H)-one
2-Ethyl-4-[(4-methylpyridin-3-yl)amino]-6-phenylpyridazin-3(2H)-one
2-Ethyl-4-[(4-methyl-1-oxidopyridin-3-yl)amino]-6-phenylpyridazin-3(2H)-one
Ethyl 4-[(2-ethyl-3-oxo-6-phenyl-2,3-dihydropyridazin-4-yl)amino]benzoate.

or a pharmaceutically acceptable salt thereof.

25. A pharmaceutical composition, comprising a compound according to claim 1 and a pharmaceutically acceptable diluent or carrier.

26. A method for treating a subject afflicted with a pathological condition or disease susceptible to amelioration by inhibition of phosphodiesterase 4, comprising administering to said subject an effective amount of a compound according to claim 1, wherein the pathological condition or disease is chosen from asthma, atopic dermatitis and psoriasis.

27. A combination product comprising:
(i) a compound according to claim 1; and
(ii) another compound chosen from (a) steroids, (b) immunosuppressive agents, (c) T-cell receptor blockers and (d) antiinflammatory drugs.

28. A method for treating a subject afflicted with a pathological condition or disease susceptible to amelioration by inhibition of phosphodiesterase 4, comprising administering to said subject an effective amount of a compound according to claim 1, and further comprising the simultaneous, separate or sequential administration to said subject of another compound chosen from (a) steroids, (b) immunosuppressive agents, (c) T-cell receptor blockers and (d) antiinflammatory drugs, wherein the pathological condition or disease is chosen from asthma, atopic dermatitis and psoriasis.

* * * * *